(12) United States Patent
Macphee et al.

(10) Patent No.: US 10,858,402 B2
(45) Date of Patent: Dec. 8, 2020

(54) SYNTHETIC MULTIPHASE SYSTEMS

(71) Applicant: University Court of the University of Edinburgh, Midlothian (GB)

(72) Inventors: Cait Macphee, Edinburgh (GB); Nicola Stanley-Wall, Dundee (GB); Keith Bromley, Edinburgh (GB); Ryan Morris, Edingburgh (GB); Laura Hobley, Dundee (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 16/736,505

(22) Filed: Jan. 7, 2020

(65) Prior Publication Data

US 2020/0207813 A1 Jul. 2, 2020

Related U.S. Application Data

(62) Division of application No. 15/504,925, filed as application No. PCT/GB2015/052396 on Aug. 18, 2015, now Pat. No. 10,570,181.

(30) Foreign Application Priority Data

Aug. 19, 2014 (GB) .................................. 14147632.6
Jul. 3, 2015 (GB) .................................. 1511724.5

(51) Int. Cl.
| | | |
|---|---|---|
| *C07K 14/32* | (2006.01) |
| *A61K 8/64* | (2006.01) |
| *A61K 9/50* | (2006.01) |
| *A61K 8/04* | (2006.01) |
| *A61K 8/06* | (2006.01) |
| *A61K 9/107* | (2006.01) |
| *A61K 9/12* | (2006.01) |
| *A61K 47/42* | (2017.01) |
| *A23G 9/46* | (2006.01) |
| *A23G 9/38* | (2006.01) |
| *A23P 30/40* | (2016.01) |
| *A61K 8/11* | (2006.01) |

(52) U.S. Cl.
CPC ................ *C07K 14/32* (2013.01); *A23G 9/38* (2013.01); *A23G 9/46* (2013.01); *A23P 30/40* (2016.08); *A61K 8/046* (2013.01); *A61K 8/06* (2013.01); *A61K 8/11* (2013.01); *A61K 8/64* (2013.01); *A61K 9/107* (2013.01); *A61K 9/122* (2013.01); *A61K 9/5052* (2013.01); *A61K 47/42* (2013.01); *A23V 2002/00* (2013.01); *A23V 2200/222* (2013.01); *A23V 2200/226* (2013.01); *C07K 2319/23* (2013.01)

(58) Field of Classification Search
None
See application file for complete search history.

(56) References Cited

U.S. PATENT DOCUMENTS 10,570,181 B2 * 2/2020 MacPhee ................. A61K 8/64

* cited by examiner

*Primary Examiner* — Sarvamangala Devi
(74) *Attorney, Agent, or Firm* — Dickison Wright PLLC

(57) ABSTRACT

A synthetic multiphase product including an isolated biofilm surface layer protein A (BslA), wherein the BslA has the amino acid sequence set forth in SEQ ID NO: 28 or a variant thereof that is at least 80% identical to SEQ ID NO: 28.

8 Claims, 38 Drawing Sheets

Specification includes a Sequence Listing.

A  B  C

D  E

F

A

B

SEQUENCE LISTING

```
<160> NUMBER OF SEQ ID NOS: 29

<210> SEQ ID NO 1
<211> LENGTH: 181
<212> TYPE: PRT
<213> ORGANISM: Bacillus subtilis

<400> SEQUENCE: 1

Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu Ser Thr
            20                  25                  30

Ser Thr Lys Ala His Thr Glu Ser Thr Met Arg Thr Gln Ser Thr Ala
        35                  40                  45

Ser Leu Phe Ala Thr Ile Thr Gly Ala Ser Lys Thr Glu Trp Ser Phe
    50                  55                  60

Ser Asp Ile Glu Leu Thr Tyr Arg Pro Asn Thr Leu Leu Ser Leu Gly
65                  70                  75                  80

Val Met Glu Phe Thr Leu Pro Ser Gly Phe Thr Ala Asn Thr Lys Asp
                85                  90                  95

Thr Leu Asn Gly Asn Ala Leu Arg Thr Thr Gln Ile Leu Asn Asn Gly
            100                 105                 110

Lys Thr Val Arg Val Pro Leu Ala Leu Asp Leu Leu Gly Ala Gly Glu
        115                 120                 125

Phe Lys Leu Lys Leu Asn Asn Lys Thr Leu Pro Ala Ala Gly Thr Tyr
    130                 135                 140
```

```
Thr Phe Arg Ala Glu Asn Lys Ser Leu Ser Ile Gly Asn Lys Phe Tyr
145                 150                 155                 160

Ala Glu Ala Ser Ile Asp Val Ala Lys Arg Ser Thr Pro Pro Thr Gln
            165                 170                 175

Pro Cys Gly Cys Asn
            180

<210> SEQ ID NO 2
<211> LENGTH: 140
<212> TYPE: PRT
<213> ORGANISM: Bacillus subtilis

<400> SEQUENCE: 2

Met Arg Thr Gln Ser Thr Ala Ser Leu Phe Ala Thr Ile Thr Gly Ala
1               5                   10                  15

Ser Lys Thr Glu Trp Ser Phe Ser Asp Ile Glu Leu Thr Tyr Arg Pro
                20                  25                  30

Asn Thr Leu Leu Ser Leu Gly Val Met Glu Phe Thr Leu Pro Ser Gly
            35                  40                  45

Phe Thr Ala Asn Thr Lys Asp Thr Leu Asn Gly Asn Ala Leu Arg Thr
    50                  55                  60

Thr Gln Ile Leu Asn Asn Gly Lys Thr Val Arg Val Pro Leu Ala Leu
65                  70                  75                  80

Asp Leu Leu Gly Ala Gly Glu Phe Lys Leu Lys Leu Asn Asn Lys Thr
                85                  90                  95

Leu Pro Ala Ala Gly Thr Tyr Thr Phe Arg Ala Glu Asn Lys Ser Leu
            100                 105                 110

Ser Ile Gly Asn Lys Phe Tyr Ala Glu Ala Ser Ile Asp Val Ala Lys
        115                 120                 125

Arg Ser Thr Pro Pro Thr Gln Pro Cys Gly Cys Asn
    130                 135                 140

<210> SEQ ID NO 3
<211> LENGTH: 181
<212> TYPE: PRT
<213> ORGANISM: Bacillus subtilis

<400> SEQUENCE: 3

Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu Ser Thr
                20                  25                  30

Ser Thr Lys Ala His Thr Glu Ser Thr Met Arg Thr Gln Ser Thr Ala
            35                  40                  45

Ser Leu Phe Ala Thr Ile Thr Gly Ala Ser Lys Thr Glu Trp Ser Phe
    50                  55                  60

Ser Asp Ile Glu Leu Thr Tyr Arg Pro Asn Thr Leu Lys Ser Leu Gly
65                  70                  75                  80

Val Met Glu Phe Thr Leu Pro Ser Gly Phe Thr Ala Asn Thr Lys Asp
                85                  90                  95

Thr Leu Asn Gly Asn Ala Leu Arg Thr Thr Gln Ile Leu Asn Asn Gly
            100                 105                 110

Lys Thr Val Arg Val Pro Leu Ala Leu Asp Leu Leu Gly Ala Gly Glu
        115                 120                 125

Phe Lys Leu Lys Leu Asn Asn Lys Thr Leu Pro Ala Ala Gly Thr Tyr
    130                 135                 140
```

```
Thr Phe Arg Ala Glu Asn Lys Ser Leu Ser Ile Gly Asn Lys Phe Tyr
145                 150                 155                 160

Ala Glu Ala Ser Ile Asp Val Ala Lys Arg Ser Thr Pro Thr Gln
                165                 170                 175

Pro Cys Gly Cys Asn
            180

<210> SEQ ID NO 4
<211> LENGTH: 140
<212> TYPE: PRT
<213> ORGANISM: Bacillus subtilis

<400> SEQUENCE: 4

Met Arg Thr Gln Ser Thr Ala Ser Leu Phe Ala Thr Ile Thr Gly Ala
1               5                   10                  15

Ser Lys Thr Glu Trp Ser Phe Ser Asp Ile Glu Leu Thr Tyr Arg Pro
                20                  25                  30

Asn Thr Leu Lys Ser Leu Gly Val Met Glu Phe Thr Leu Pro Ser Gly
            35                  40                  45

Phe Thr Ala Asn Thr Lys Asp Thr Leu Asn Gly Asn Ala Leu Arg Thr
    50                  55                  60

Thr Gln Ile Leu Asn Asn Gly Lys Thr Val Arg Val Pro Leu Ala Leu
65                  70                  75                  80

Asp Leu Leu Gly Ala Gly Glu Phe Lys Leu Lys Leu Asn Asn Lys Thr
                85                  90                  95

Leu Pro Ala Ala Gly Thr Tyr Thr Phe Arg Ala Glu Asn Lys Ser Leu
            100                 105                 110

Ser Ile Gly Asn Lys Phe Tyr Ala Glu Ala Ser Ile Asp Val Ala Lys
        115                 120                 125

Arg Ser Thr Pro Pro Thr Gln Pro Cys Gly Cys Asn
    130                 135                 140

<210> SEQ ID NO 5
<211> LENGTH: 546
<212> TYPE: DNA
<213> ORGANISM: Bacillus subtilis

<400> SEQUENCE: 5
atgaaacgca aattattatc ttctttggca attagtgcat taagtctcgg gttactcgtt      60
tctgcaccta cagcttcttt cgcggctgaa tctacatcaa ctaaagctca tactgaatcc     120
actatgagaa cacagtctac agcttcattg ttcgcaacaa tcactggcgc cagcaaaacg     180
gaatggtctt tctcagatat cgaattgact taccgtccaa acacgcttct cagccttggc     240
gttatggagt ttacattgcc aagcggattt actgcaaaca cgaaagacac attgaacgga     300
aatgccttgc gtacaacaca gatcctcaat aacgggaaaa cagtaagagt tcctttggca     360
cttgatttgt taggagctgg cgaattcaaa ttaaaactga ataacaaaac acttcctgcc     420
gctggtacat atactttccg tgcggagaat aaatcattaa gcatcggaaa taaattttac     480
gcagaagcca gcattgacgt ggctaagcgc agcactcctc gactcagcc ttgcggttgc      540 aactaa                                                               546

<210> SEQ ID NO 6
<211> LENGTH: 1137
<212> TYPE: DNA
<213> ORGANISM: Bacillus subtilis

<400> SEQUENCE: 6
```

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ctggaagttc tgttccaggg gcccctggga tccgaaaatt tatattttca aatgagaaca     720
cagtctacag cttcattgtt cgcaacaatc actggcgcca gcaaaacgga atggtctttc     780
tcagatatcg aattgactta ccgtccaaac acgcttctca gccttggcgt tatggagttt     840
acattgccaa gcggatttac tgcaaacacg aaagacacat gaacggaaa tgccttgcgt     900
acaacacaga tcctcaataa cgggaaaaca gtaagagttc ctttggcact tgatttgtta     960
ggagctggcg aattcaaatt aaaactgaat aacaaaacac ttcctgccgc tggtacatat    1020
actttccgtg cggagaataa atcattaagc atcggaaata aattttacgc agaagccagc    1080
attgacgtgg ctaagcgcag cactcctccg actcagcctt gcggttgcaa ctaataa      1137
```

<210> SEQ ID NO 7
<211> LENGTH: 377
<212> TYPE: PRT
<213> ORGANISM: Bacillus subtilis

<400> SEQUENCE: 7

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175
```

```
Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Glu Asn Leu Tyr Phe Gln Met Arg Thr
225                 230                 235                 240

Gln Ser Thr Ala Ser Leu Phe Ala Thr Ile Thr Gly Ala Ser Lys Thr
                245                 250                 255

Glu Trp Ser Phe Ser Asp Ile Glu Leu Thr Tyr Arg Pro Asn Thr Leu
            260                 265                 270

Leu Ser Leu Gly Val Met Glu Phe Thr Leu Pro Ser Gly Phe Thr Ala
        275                 280                 285

Asn Thr Lys Asp Thr Leu Asn Gly Asn Ala Leu Arg Thr Thr Gln Ile
    290                 295                 300

Leu Asn Asn Gly Lys Thr Val Arg Val Pro Leu Ala Leu Asp Leu Leu
305                 310                 315                 320

Gly Ala Gly Glu Phe Lys Leu Lys Leu Asn Asn Lys Thr Leu Pro Ala
                325                 330                 335

Ala Gly Thr Tyr Thr Phe Arg Ala Glu Asn Lys Ser Leu Ser Ile Gly
            340                 345                 350

Asn Lys Phe Tyr Ala Glu Ala Ser Ile Asp Val Ala Lys Arg Ser Thr
        355                 360                 365

Pro Pro Thr Gln Pro Cys Gly Cys Asn
    370                 375

<210> SEQ ID NO 8
<211> LENGTH: 1137
<212> TYPE: DNA
<213> ORGANISM: Bacillus subtilis

<400> SEQUENCE: 8
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt tgtttttaaa     540
aaacgtattg aagctatccc acaaattgat aagtacttga atccagcaa gtatatagca     600 tggcctttgc agggctggca agccacgttt ggtggtggcg accatcctcc aaaatcggat     660
ctggaagttc tgttccaggg gcccctggga tccgaaaatt tatattttca atgagaaca     720 cagtctacag cttcattgtt cgcaacaatc actggcgcca gcaaaacgga atggtctttc     780
tcagatatcg aattgactta ccgtccaaac acgcttaaaa gccttggcgt tatggagttt     840
acattgccaa gcggatttac tgcaaacacg aaagacacat gaacggaaa tgccttgcgt     900 acaacacaga tcctcaataa cgggaaaaca gtaagagttc ctttggcact tgatttgtta     960
```

```
ggagctggcg aattcaaatt aaaactgaat aacaaaacac ttcctgccgc tggtacatat   1020
actttccgtg cggagaataa atcattaagc atcggaaata aattttacgc agaagccagc   1080
attgacgtgg ctaagcgcag cactcctccg actcagcctt gcggttgcaa ctaataa      1137
```

<210> SEQ ID NO 9
<211> LENGTH: 377
<212> TYPE: PRT
<213> ORGANISM: Bacillus subtilis

<400> SEQUENCE: 9

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Glu Asn Leu Tyr Phe Gln Met Arg Thr
225                 230                 235                 240

Gln Ser Thr Ala Ser Leu Phe Ala Thr Ile Thr Gly Ala Ser Lys Thr
                245                 250                 255

Glu Trp Ser Phe Ser Asp Ile Glu Leu Thr Tyr Arg Pro Asn Thr Leu
            260                 265                 270

Lys Ser Leu Gly Val Met Glu Phe Thr Leu Pro Ser Gly Phe Thr Ala
        275                 280                 285

Asn Thr Lys Asp Thr Leu Asn Gly Asn Ala Leu Arg Thr Thr Gln Ile
    290                 295                 300

Leu Asn Asn Gly Lys Thr Val Arg Val Pro Leu Ala Leu Asp Leu Leu
305                 310                 315                 320

Gly Ala Gly Glu Phe Lys Leu Lys Leu Asn Asn Lys Thr Leu Pro Ala
                325                 330                 335

Ala Gly Thr Tyr Thr Phe Arg Ala Glu Asn Lys Ser Leu Ser Ile Gly
```

```
                340                 345                 350
Asn Lys Phe Tyr Ala Glu Ala Ser Ile Asp Val Ala Lys Arg Ser Thr
            355                 360                 365

Pro Pro Thr Gln Pro Cys Gly Cys Asn
    370                 375

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
ccgtccaaac acgcttaaaa gccttggcgt tatgg                              35

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
ccataacgcc aaggctttta agcgtgtttg gacgg                              35

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
tcctccgact cagcctgcag gttgcaacta ataac                              35

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
gttattagtt gcaacctgca ggctgagtcg gagga                              35

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
gactcagcct tgcggtgcaa actaataact cgagc                              35

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
gctcgagtta ttagtttgca ccgcaaggct gagtc                              35
```

-continued

<210> SEQ ID NO 16
<211> LENGTH: 35
<212> TYPE: DNA
<213> ORGANISM: Artificial Sequence
<220> FEATURE:
<223> OTHER INFORMATION: Primer

<400> SEQUENCE: 16
tccgactcag cctgcaggtg caaactaata actcg                              35

<210> SEQ ID NO 17
<211> LENGTH: 35
<212> TYPE: DNA
<213> ORGANISM: Artificial Sequence
<220> FEATURE:
<223> OTHER INFORMATION: Primer

<400> SEQUENCE: 17
cgagttatta gtttgcacct gcaggctgag tcgga                              35

<210> SEQ ID NO 18
<211> LENGTH: 181
<212> TYPE: PRT
<213> ORGANISM: Bacillus subtilis
<220> FEATURE:
<221> NAME/KEY: Xaa
<222> LOCATION: (178)..(180)
<223> OTHER INFORMATION: Xaa is any amino acid that is not cysteine or
      methionine

<400> SEQUENCE: 18

Met Lys Arg Lys Leu Leu Ser Ser Leu Ala Ile Ser Ala Leu Ser Leu
1               5                   10                  15

Gly Leu Leu Val Ser Ala Pro Thr Ala Ser Phe Ala Ala Glu Ser Thr
            20                  25                  30

Ser Thr Lys Ala His Thr Glu Ser Thr Met Arg Thr Gln Ser Thr Ala
        35                  40                  45

Ser Leu Phe Ala Thr Ile Thr Gly Ala Ser Lys Thr Glu Trp Ser Phe
    50                  55                  60

Ser Asp Ile Glu Leu Thr Tyr Arg Pro Asn Thr Leu Leu Ser Leu Gly
65                  70                  75                  80

Val Met Glu Phe Thr Leu Pro Ser Gly Phe Thr Ala Asn Thr Lys Asp
                85                  90                  95

Thr Leu Asn Gly Asn Ala Leu Arg Thr Thr Gln Ile Leu Asn Asn Gly
            100                 105                 110

Lys Thr Val Arg Val Pro Leu Ala Leu Asp Leu Leu Gly Ala Gly Glu
        115                 120                 125

Phe Lys Leu Lys Leu Asn Asn Lys Thr Leu Pro Ala Ala Gly Thr Tyr
    130                 135                 140

Thr Phe Arg Ala Glu Asn Lys Ser Leu Ser Ile Gly Asn Lys Phe Tyr
145                 150                 155                 160

Ala Glu Ala Ser Ile Asp Val Ala Lys Arg Ser Thr Pro Pro Thr Gln
                165                 170                 175

Pro Xaa Gly Xaa Asn
        180

<210> SEQ ID NO 19
<211> LENGTH: 140
<212> TYPE: PRT
<213> ORGANISM: Bacillus subtilis

```
<220> FEATURE:
<221> NAME/KEY: Xaa
<222> LOCATION: (137)..(139)
<223> OTHER INFORMATION: Xaa is any amino acid that is not cysteine or
      methionine

<400> SEQUENCE: 19
```

| | | | | | | | | | | | | | | | |
|---|---|---|---|---|---|---|---|---|---|---|---|---|---|---|---|
| Met | Arg | Thr | Gln | Ser | Thr | Ala | Ser | Leu | Phe | Ala | Thr | Ile | Thr | Gly | Ala |
| 1 | | | | 5 | | | | | 10 | | | | | 15 | |
| Ser | Lys | Thr | Glu | Trp | Ser | Phe | Ser | Asp | Ile | Glu | Leu | Thr | Tyr | Arg | Pro |
| | | | 20 | | | | | 25 | | | | | 30 | | |
| Asn | Thr | Leu | Leu | Ser | Leu | Gly | Val | Met | Glu | Phe | Thr | Leu | Pro | Ser | Gly |
| | | | 35 | | | | | 40 | | | | | 45 | | |
| Phe | Thr | Ala | Asn | Thr | Lys | Asp | Thr | Leu | Asn | Gly | Asn | Ala | Leu | Arg | Thr |
| 50 | | | | | 55 | | | | | 60 | | | | | |
| Thr | Gln | Ile | Leu | Asn | Asn | Gly | Lys | Thr | Val | Arg | Val | Pro | Leu | Ala | Leu |
| 65 | | | | | 70 | | | | | 75 | | | | | 80 |
| Asp | Leu | Leu | Gly | Ala | Gly | Glu | Phe | Lys | Leu | Lys | Leu | Asn | Asn | Lys | Thr |
| | | | | 85 | | | | | 90 | | | | | 95 | |
| Leu | Pro | Ala | Ala | Gly | Thr | Tyr | Thr | Phe | Arg | Ala | Glu | Asn | Lys | Ser | Leu |
| | | | 100 | | | | | 105 | | | | | 110 | | |
| Ser | Ile | Gly | Asn | Lys | Phe | Tyr | Ala | Glu | Ala | Ser | Ile | Asp | Val | Ala | Lys |
| | | | 115 | | | | | 120 | | | | | 125 | | |
| Arg | Ser | Thr | Pro | Pro | Thr | Gln | Pro | Xaa | Gly | Xaa | Asn | | | | |
| 130 | | | | | 135 | | | | | 140 | | | | | |

```
<210> SEQ ID NO 20
<211> LENGTH: 181
<212> TYPE: PRT
<213> ORGANISM: Bacillus subtilis

<400> SEQUENCE: 20
```

| | | | | | | | | | | | | | | | |
|---|---|---|---|---|---|---|---|---|---|---|---|---|---|---|---|
| Met | Lys | Arg | Lys | Leu | Leu | Ser | Ser | Leu | Ala | Ile | Ser | Ala | Leu | Ser | Leu |
| 1 | | | | 5 | | | | | 10 | | | | | 15 | |
| Gly | Leu | Leu | Val | Ser | Ala | Pro | Thr | Ala | Ser | Phe | Ala | Ala | Glu | Ser | Thr |
| | | | 20 | | | | | 25 | | | | | 30 | | |
| Ser | Thr | Lys | Ala | His | Thr | Glu | Ser | Thr | Met | Arg | Thr | Gln | Ser | Thr | Ala |
| | | | 35 | | | | | 40 | | | | | 45 | | |
| Ser | Leu | Phe | Ala | Thr | Ile | Thr | Gly | Ala | Ser | Lys | Thr | Glu | Trp | Ser | Phe |
| 50 | | | | | 55 | | | | | 60 | | | | | |
| Ser | Asp | Ile | Glu | Leu | Thr | Tyr | Arg | Pro | Asn | Thr | Leu | Leu | Ser | Leu | Gly |
| 65 | | | | | 70 | | | | | 75 | | | | | 80 |
| Val | Met | Glu | Phe | Thr | Leu | Pro | Ser | Gly | Phe | Thr | Ala | Asn | Thr | Lys | Asp |
| | | | | 85 | | | | | 90 | | | | | 95 | |
| Thr | Leu | Asn | Gly | Asn | Ala | Leu | Arg | Thr | Thr | Gln | Ile | Leu | Asn | Asn | Gly |
| | | | 100 | | | | | 105 | | | | | 110 | | |
| Lys | Thr | Val | Arg | Val | Pro | Leu | Ala | Leu | Asp | Leu | Leu | Gly | Ala | Gly | Glu |
| | | | 115 | | | | | 120 | | | | | 125 | | |
| Phe | Lys | Leu | Lys | Leu | Asn | Asn | Lys | Thr | Leu | Pro | Ala | Ala | Gly | Thr | Tyr |
| 130 | | | | | 135 | | | | | 140 | | | | | |
| Thr | Phe | Arg | Ala | Glu | Asn | Lys | Ser | Leu | Ser | Ile | Gly | Asn | Lys | Phe | Tyr |
| 145 | | | | | 150 | | | | | 155 | | | | | 160 |
| Ala | Glu | Ala | Ser | Ile | Asp | Val | Ala | Lys | Arg | Ser | Thr | Pro | Thr | Gln | |
| | | | | 165 | | | | | 170 | | | | | 175 | |
| Pro | Ala | Gly | Ala | Asn | | | | | | | | | | | |
| | | | | 180 | | | | | | | | | | | |

<210> SEQ ID NO 21
<211> LENGTH: 140
<212> TYPE: PRT
<213> ORGANISM: Bacillus subtilis

<400> SEQUENCE: 21

Met Arg Thr Gln Ser Thr Ala Ser Leu Phe Ala Thr Ile Thr Gly Ala
1               5                   10                  15

Ser Lys Thr Glu Trp Ser Phe Ser Asp Ile Glu Leu Thr Tyr Arg Pro
                20                  25                  30

Asn Thr Leu Leu Ser Leu Gly Val Met Glu Phe Thr Leu Pro Ser Gly
            35                  40                  45

Phe Thr Ala Asn Thr Lys Asp Thr Leu Asn Gly Asn Ala Leu Arg Thr
50                  55                  60

Thr Gln Ile Leu Asn Asn Gly Lys Thr Val Arg Val Pro Leu Ala Leu
65                  70                  75                  80

Asp Leu Leu Gly Ala Gly Glu Phe Lys Leu Lys Leu Asn Asn Lys Thr
                85                  90                  95

Leu Pro Ala Ala Gly Thr Tyr Thr Phe Arg Ala Glu Asn Lys Ser Leu
            100                 105                 110

Ser Ile Gly Asn Lys Phe Tyr Ala Glu Ala Ser Ile Asp Val Ala Lys
        115                 120                 125

Arg Ser Thr Pro Pro Thr Gln Pro Ala Gly Ala Asn
    130                 135                 140

<210> SEQ ID NO 22
<211> LENGTH: 140
<212> TYPE: PRT
<213> ORGANISM: Bacillus licheniformis

<400> SEQUENCE: 22

Tyr Arg Pro Ala Ala Ser Ala Ser Leu Tyr Ser Val Ile Thr Gly Ala
1               5                   10                  15

Ser Lys Gln Glu Trp Ser Phe Ser Asp Ile Glu Leu Thr Tyr Arg Pro
                20                  25                  30

Asn Ser Ile Leu Ala Leu Gly Thr Val Glu Phe Thr Leu Pro Ser Gly
            35                  40                  45

Phe Ser Ala Thr Thr Lys Asp Thr Val Asn Gly Arg Ala Leu Thr Thr
50                  55                  60

Gly Gln Ile Leu Asn Asn Gly Lys Thr Val Arg Leu Pro Leu Thr Ile
65                  70                  75                  80

Asp Leu Leu Gly Ile Ala Glu Phe Lys Leu Val Leu Ala Asn Lys Thr
                85                  90                  95

Leu Pro Ala Ala Gly Lys Tyr Thr Phe Arg Ala Glu Asn Arg Val Leu
            100                 105                 110

Gly Leu Gly Ser Thr Phe Tyr Ala Glu Ser Ser Ile Glu Val Gln Lys
        115                 120                 125

Arg Ala Thr Pro Pro Thr Gln Pro Cys Asn Cys Lys
    130                 135                 140

<210> SEQ ID NO 23
<211> LENGTH: 140
<212> TYPE: PRT
<213> ORGANISM: Bacillus amyloliquefaciens

<400> SEQUENCE: 23

Met Ser Thr Lys Ala Thr Ala Thr Leu Phe Ala Lys Tyr Thr Gly Ala
1               5                   10                  15

```
               1               5                  10                  15
            Ser Gln Gln Glu Trp Ser Phe Ser Asp Ile Glu Leu Thr Tyr Arg Pro
                            20                  25                  30

Asn Thr Ile Leu Ser Leu Gly Val Met Glu Phe Thr Leu Pro Ser Gly
                            35                  40                  45

Phe Ala Thr Thr Lys Asp Thr Val Asn Gly His Ala Leu Arg Glu
                50                  55                  60

Arg Gln Ile Leu Asn Asn Gly Lys Thr Val Arg Leu Pro Leu Asn Ile
             65                 70                  75                  80

Asp Leu Leu Gly Ala Ala Glu Phe Lys Leu Ser Leu Asn Asn Lys Thr
                            85                  90                  95

Leu Pro Ala Ala Gly Thr Tyr Lys Phe Arg Ala Glu Asn Lys Ser Leu
                            100                 105                 110

Ser Ile Gly Ser Lys Phe Tyr Ala Glu Asp Thr Ile Val Val Gln Lys
                            115                 120                 125

Arg Ser Thr Pro Pro Thr Gln Pro Cys Asn Cys Lys
                            130                 135                 140
```

<210> SEQ ID NO 24
<211> LENGTH: 141
<212> TYPE: PRT
<213> ORGANISM: Bacillus pumilus

<400> SEQUENCE: 24

```
            Ser Thr Asn Ala Arg Pro Ala Glu Leu Tyr Ala Lys Ile Thr Gly Thr
             1                 5                  10                  15

Ser Lys Gln Glu Trp Ser Phe Ser Asp Ile Glu Leu Thr Tyr Arg Pro
                            20                  25                  30

Asn Ser Val Leu Ser Leu Gly Ala Ile Glu Phe Thr Leu Pro Ala Gly
                            35                  40                  45

Phe Gln Ala Thr Thr Lys Asp Ile Phe Asn Gly Lys Ala Leu Lys Asp
                50                  55                  60

Ser Tyr Ile Leu Asn Ser Gly Lys Thr Val Arg Ile Pro Ala Arg Leu
             65                 70                  75                  80

Asp Leu Leu Gly Ile Ser Gln Phe Lys Leu Gln Leu Ser His Lys Val
                            85                  90                  95

Leu Pro Ala Ala Gly Thr Tyr Thr Phe Arg Ala Glu Asn Arg Ala Leu
                            100                 105                 110

Ser Ile Gly Ser Lys Phe Tyr Ala Glu Asp Thr Leu Asp Ile Gln Thr
                            115                 120                 125

Arg Pro Val Val Val Thr Pro Pro Asp Pro Cys Gly Cys
                            130                 135                 140
```

<210> SEQ ID NO 25
<211> LENGTH: 181
<212> TYPE: PRT
<213> ORGANISM: Bacillus licheniformis

<400> SEQUENCE: 25

```
            Met Lys Met Lys His Lys Phe Phe Ser Thr Val Met Ala Ser Leu Phe
             1                 5                  10                  15

Gly Leu Val Leu Leu Leu Ser Leu Pro Thr Ala Ser Phe Ala Ala Glu
                            20                  25                  30

Ser Ser Ser Thr Val His Glu Pro Glu Met Ser Thr Lys Ala Thr Ala
                            35                  40                  45

Thr Leu Phe Ala Lys Tyr Thr Gly Ala Ser Gln Gln Glu Trp Ser Phe
```

```
            50                  55                  60
Ser Asp Ile Glu Leu Thr Tyr Arg Pro Asn Thr Ile Leu Ser Leu Gly
 65                  70                  75                  80

Val Met Glu Phe Thr Leu Pro Ser Gly Phe Thr Ala Thr Lys Asp
                 85                  90                  95

Thr Val Asn Gly His Ala Leu Arg Glu Arg Gln Ile Leu Asn Asn Gly
                100                 105                 110

Lys Thr Val Arg Leu Pro Leu Asn Ile Asp Leu Ile Gly Ala Ala Glu
                115                 120                 125

Phe Lys Leu Ser Leu Asn Asn Lys Thr Leu Pro Ala Ala Gly Thr Tyr
130                 135                 140

Lys Phe Arg Ala Glu Asn Lys Ser Leu Ser Ile Gly Ser Lys Phe Tyr
145                 150                 155                 160

Ala Glu Asp Thr Ile Val Val Gln Lys Arg Ser Thr Pro Pro Thr Gln
                165                 170                 175

Pro Cys Asn Cys Lys
                180

<210> SEQ ID NO 26
<211> LENGTH: 180
<212> TYPE: PRT
<213> ORGANISM: Bacillus amyloliquefaciens

<400> SEQUENCE: 26

Met Leu Lys Arg Met Tyr Arg Ser Lys Leu Ser Ile Leu Ala Val Ser
 1               5                  10                  15

Leu Val Met Met Val Ser Ile Phe Leu Pro Ser Phe Gln Ala Ser Ala
                 20                  25                  30

Gln Thr Thr Lys Thr Glu Ser Val Tyr Arg Pro Ala Ala Asn Ala Ser
                 35                  40                  45

Leu Tyr Ala Thr Ile Thr Gly Ala Ser Lys Gln Glu Trp Ser Phe Ser
 50                  55                  60

Asp Ile Glu Leu Thr Tyr Arg Pro Asn Ser Ile Leu Ala Leu Gly Thr
 65                  70                  75                  80

Val Glu Phe Thr Leu Pro Ser Gly Phe Ser Ala Thr Thr Lys Asp Thr
                 85                  90                  95

Val Asn Gly Arg Ala Leu Thr Thr Gly Gln Ile Leu Asn Asn Gly Lys
                100                 105                 110

Thr Val Arg Leu Pro Leu Thr Ile Asp Leu Leu Gly Ile Ala Glu Phe
                115                 120                 125

Lys Leu Val Leu Ala Asn Lys Thr Leu Pro Ala Ala Gly Lys Tyr Thr
130                 135                 140

Phe Arg Ala Glu Asn Arg Val Leu Gly Leu Gly Ser Thr Phe Tyr Ala
145                 150                 155                 160

Glu Ser Ser Ile Glu Val Gln Lys Arg Ala Thr Pro Pro Thr Gln Pro
                165                 170                 175

Cys Asn Cys Lys
                180

<210> SEQ ID NO 27
<211> LENGTH: 177
<212> TYPE: PRT
<213> ORGANISM: Bacillus pumilus

<400> SEQUENCE: 27

Met Lys Lys Thr Trp Thr Met Ile Met Met Gly Met Leu Thr Leu Val
```

-continued

```
                1               5                      10                     15
        Met Ala Leu Ser Val Pro Ile Ala Ala Ser Ala Glu Gly Ala Thr Gln
                        20                      25                     30
        Glu Gly Lys Ala Ser Thr Asn Ala Arg Pro Ala Glu Leu Tyr Ala Lys
                        35                      40                     45
        Ile Thr Gly Thr Ser Lys Gln Glu Trp Ser Phe Ser Asp Ile Glu Leu
                        50                      55                     60
        Thr Tyr Arg Pro Asn Ser Val Leu Ser Leu Gly Ala Ile Glu Phe Thr
        65                      70                      75                     80
        Leu Pro Ala Gly Phe Gln Ala Thr Thr Lys Asp Ile Phe Asn Gly Lys
                        85                      90                     95
        Ala Leu Lys Asp Ser Tyr Ile Leu Asn Ser Gly Lys Thr Val Arg Ile
                        100                     105                    110
        Pro Ala Arg Leu Asp Leu Leu Gly Ile Ser Gln Phe Lys Leu Gln Leu
                        115                     120                    125
        Ser His Lys Val Leu Pro Ala Ala Gly Thr Tyr Thr Phe Arg Ala Glu
                        130                     135                    140
        Asn Arg Ala Leu Ser Ile Gly Ser Lys Phe Tyr Ala Glu Asp Thr Leu
        145                     150                     155                    160
        Asp Ile Gln Thr Arg Pro Val Val Val Thr Pro Asp Pro Cys Gly
                        165                     170                    175
        Cys
```

<210> SEQ ID NO 28
<211> LENGTH: 154
<212> TYPE: PRT
<213> ORGANISM: Bacillus subtilis

<400> SEQUENCE: 28

```
        Met Leu Lys Arg Thr Ser Phe Val Ser Ser Leu Phe Ile Ser Ser Ala
        1                       5                       10                     15
        Val Leu Leu Ser Ile Leu Leu Pro Ser Gly Gln Ala His Ala Gln Ser
                        20                      25                     30
        Ala Ser Ile Glu Ala Lys Thr Val Asn Ser Thr Lys Glu Trp Thr Ile
                        35                      40                     45
        Ser Asp Ile Glu Val Thr Tyr Lys Pro Asn Ala Val Leu Ser Leu Gly
                        50                      55                     60
        Ala Val Glu Phe Gln Phe Pro Asp Gly Phe His Ala Thr Thr Arg Asp
        65                      70                      75                     80
        Ser Val Asn Gly Arg Thr Leu Lys Glu Thr Gln Ile Leu Asn Asp Gly
                        85                      90                     95
        Lys Thr Val Arg Leu Pro Leu Thr Leu Asp Leu Leu Gly Ala Ser Glu
                        100                     105                    110
        Phe Asp Leu Val Met Val Arg Lys Thr Leu Pro Arg Ala Gly Thr Tyr
                        115                     120                    125
        Thr Ile Lys Gly Asp Val Val Asn Gly Leu Gly Ile Gly Ser Phe Tyr
                        130                     135                    140
        Ala Glu Thr Gln Leu Val Ile Asp Pro Arg
        145                     150
```

<210> SEQ ID NO 29
<211> LENGTH: 124
<212> TYPE: PRT
<213> ORGANISM: Bacillus subtilis

<400> SEQUENCE: 29

```
Gln Ser Ala Ser Ile Glu Ala Lys Thr Val Asn Ser Thr Lys Glu Trp
1               5                   10                  15

Thr Ile Ser Asp Ile Glu Val Thr Tyr Lys Pro Asn Ala Val Leu Ser
            20                  25                  30

Leu Gly Ala Val Glu Phe Gln Phe Pro Asp Gly Phe His Ala Thr Thr
        35                  40                  45

Arg Asp Ser Val Asn Gly Arg Thr Leu Lys Glu Thr Gln Ile Leu Asn
    50                  55                  60

Asp Gly Lys Thr Val Arg Leu Pro Leu Thr Leu Asp Leu Leu Gly Ala
65                  70                  75                  80

Ser Glu Phe Asp Leu Val Met Val Arg Lys Thr Leu Pro Arg Ala Gly
            85                  90                  95

Thr Tyr Thr Ile Lys Gly Asp Val Val Asn Gly Leu Gly Ile Gly Ser
            100                 105                 110

Phe Tyr Ala Glu Thr Gln Leu Val Ile Asp Pro Arg
        115                 120
```

SYNTHETIC MULTIPHASE SYSTEMS

CROSS-REFERENCE TO RELATED APPLICATIONS

The present application is a Divisional of U.S. patent application Ser. No. 15/504,925, filed 17 Feb. 2017, now U.S. Pat. No. 10,570,181, which application is a 35 U.S.C. section 371 national stage filing of International Patent Application No. PCT/GB2015/052396, filed 18 Aug. 2015, and through which priority is claimed to United Kingdom Patent Application 14147632.6, filed 19 Aug. 2014, and United Kingdom Patent Application 1511724.5, filed 3 Jul. 2015. The disclosures of U.S. patent application Ser. No. 15/504,925 and International Patent Application No. PCT/GB2015/052396 are incorporated herein by reference in their entireties.

The invention relates to the field of synthetic multiphase systems such as emulsions and foams, and uses of BslA (including variants or fragments thereof) in the stabilisation of synthetic multiphase systems.

SEQUENCE LISTING

This disclosure incorporates by reference in its entirety the material in the accompanying ASCI text file designated Sequence listing_ST25 P218845US.txt, created 18 Aug. 2015, and having a file size of 34,300 bytes

BACKGROUND OF THE INVENTION

Synthetic multiphase products, such as emulsions and foams, are unstable and will separate out into their separate phases unless they are stabilised in some way. Typically, synthetic multiphase products are stabilised by the addition of surfactants that adsorb to the interface between the phases and stabilise those interfaces by lowering the interfacial tension. The life-time of these stabilised synthetic multiphase products is greatly increased, resulting in a greater shelf-life.

Synthetic multiphase products that comprise foams, and foamable products, also require a foaming agent that will increase the extent of foaming of the liquid component of the synthetic multiphase product (i.e. an agent that will increase the amount of gas that can be incorporated into the synthetic multiphase product).

Surfactants used to stabilise multiphase food products, such as mousses, creams, and ice cream, for example, must be safe to eat and therefore, natural protein surfactants, such as sodium caseinate and whey protein isolate are often used.

However, many surfactants may perform well in isolation, but in the presence of co-surfactants, their performance may degrade dramatically. For example, the group of fungal protein surfactants, hydrophobins, stabilise multiphase systems but perform poorly when co-surfactants are present.

Accordingly, it is an object of the present invention to provide a synthetic multiphase product comprising a surfactant that stabilises synthetic multiphase products in the presence of co-surfactants.

It is a further object of the invention to provide an improved method of stabilising multiphase systems, such as synthetic multiphase products.

STATEMENTS OF THE INVENTION

According to a first aspect of the invention, there is provided a synthetic multiphase product comprising BslA.

By the term "synthetic multiphase product" we refer to a manufactured product comprising two or more intimately mixed immiscible phases of matter. Each of the two or more intimately mixed phases of matter may be phases of matter occurring in nature, may be phases of matter that are modified phases of matter occurring in nature, or may artificial phases of matter that do not occur in nature. For example, the synthetic multiphase product may comprise an emulsion comprising two or more immiscible liquid phases, such as an aqueous phase and an oil phase, the synthetic multiphase product may be a foam comprising a gas phase within a liquid phase, or the multiphase may be a sol or suspension comprising solid particles suspended within a liquid phase. The synthetic multiphase product may comprise bubbles.

The synthetic multiphase product may be a multiphase food product. The multiphase food product may be an aerated food product. That is, the multiphase food product may be a food product through which a gas, such as nitrogen, carbon dioxide, nitrous oxide, or air, has been passed to produce a foamed food product. For example, the foamed food product may be a mousse, ice cream or whipped cream. The multiphase food product may be a foamable food product, such that the foamable food product is typically a liquid and when a neutral gas is passed through the liquid by injection into the liquid, or agitation of the liquid, a foam is produced. For example, whipped cream can be made by passing nitrous oxide through the cream mixture in a whipping syphon. The multiphase food product may be an emulsified food product, such as mayonnaise, a vinaigrette, or cream, for example.

The multiphase food product may be a frozen multiphase food product. The multiphase food product may be a frozen emulsified food product, such as ice cream. The multiphase food product may be an aerated frozen multiphase product. That is, the multiphase food product may be a frozen food product through which, during preparation, a gas, such as nitrogen, carbon dioxide, nitrous oxide or air, has been passed to produce a foamed food product that has then been frozen. For example, the frozen multiphase food product may be a foamed ice cream.

The synthetic multiphase product may be a personal care product. The multiphase personal care product may be an aerated personal care product, such as shaving foam, for example. The multiphase personal care product may be a foamable personal care product, such that the foamable personal care product is a liquid and when a gas is passed through the liquid, such as by agitation or by forcing a neutral gas through the liquid, a foam or lather is produced. For example, the foamable personal care product may be a shampoo, soap, or shower gel. The multiphase personal care product may be an emulsified personal care product, such as hand cream, or moisturiser, for example.

In embodiments where the synthetic multiphase product is a foam, the gas may be nitrogen, carbon dioxide, or, preferably, air.

Typically, multiphase systems, such as synthetic multiphase products, are inherently unstable, and the multiple phases within the synthetic multiphase product will tend to separate out from one another over time. For example, two liquids that have been mixed to form an emulsion will tend to separate out into the two liquids. Accordingly, synthetic multiphased products in the art are often stabilised using surfactants that stabilise the interface between the multiple phases by lowering the interfacial tension, thereby increasing the stability of the multiphase system within the synthetic multiphase product, and thereby increasing the lifetime of the synthetic multiphase product.

Surfactants used in the art include small molecule ionic surfactants such as cetrimonium bromide ("CTAB") and sodium dodecyl sulfate ("SDS"), for example, and large molecule non-ionic surfactants, such as block copolymers (for example, PLURONIC F-127 (registered trademark of BASF SE, Germany) and polyethylene glycols (PEG) and polysorbate surfactants such as TWEEN-20 (registered trademark of Croda International PLC)), and protein surfactants commonly used in food products, such as sodium caseinate, those surfactants within whey protein isolate (a protein mixture) that are contained within milk products, and hydrophobins.

Some known protein surfactants in the art such as sodium caseinate and those within whey protein isolate, are typically added to increase the foaming properties of the liquids that are foamed to produce foamed synthetic multiphase products. In particular, proteins such as sodium caseinate and those within whey protein isolate are present or added to milk-based synthetic multiphase products, such as creams and ice creams, for example. However, these protein surfactants often do not stabilise synthetic multiphase products well once the foam has been formed, and additional surfactants are required to increase the stability of the foam, once it is produced.

Those protein surfactants that do stabilise multiphase systems, such as the fungal hydrophobins, for example, can be difficult to handle due to their poor solubility (or deactivation) in aqueous phases typically used in the preparation of synthetic multiphase products, and their interfacial stabilising properties may be severely reduced by the introduction of co-surfactants, such as foaming agents, for example.

Whilst BslA has been referred to in the art as a "bacterial hydrophobin"[1], BslA is a bacterial protein with very little sequence or structural similarity to hydrophobins, and is therefore a very different protein to hydrophobins. As such, there is little reason for the skilled person to look to BslA to have similar properties to protein surfactants, such as hydrophobins. However, the inventors have surprisingly found that BslA greatly increases the stability of multiphase systems, such as those that are present in synthetic multiphase products. BslA is a protein identified in *Bacillus subtilis*, and has previously been referred to in the literature as YuaB; another name, SivB, has been coined in the literature.

Accordingly, synthetic multiphase products comprising BslA may be stable or more stable than synthetic multiphase products that do not comprise BslA.

Furthermore, the inventors have found that BslA adopts a first conformation that is soluble in water, and that BslA changes to a second conformation when adsorbed at an interface to expose hydrophobic residues to form a "hydrophobic cap". The hydrophobic cap anchors the BslA at the interface by extending into the non-aqueous or non-polar phase. In addition, BslA in the second configuration self-assembles to form a highly structured two dimensional lattice at the interface. This two dimensional lattice forms a viscoelastic film at the interface increases the stability of the interface, and resists rearrangement or relaxation of the interface after compression or deformation. It would appear that a L77K mutant does not retain the same ability as WT-BslA to form the highly structured two dimensional lattice at the interface, presumably as the mutation destabilises the hydrophobic cap; it has significant interfacial activity, but does not form the same large-scale 2D lattice as observed with the WT-BslA protein in which the hydrophobic cap is unaltered.

Therefore, synthetic multiphase products comprising BslA are more readily made and the process of manufacturing such products is more efficient due to the soluble first configuration of BslA, and the formation of a viscoelastic film at the interface between phases further increases the stability of the synthetic multiphase products.

Without wishing to be bound by theory, it is suggested that BslA may form dimers and higher oligomers in the aqueous phase, via covalent bonds, such as between cysteine residues of neighbouring BslA molecules, or via hydrogen bonding, for example. The inventors speculate that the formation of these BslA dimers and/or higher oligomers may slow the kinetics of adsorption via a decreased diffusion coefficient and may effectively lower the concentration of the BslA available to adsorb at an interface as only one end of a BslA dimer or oligomer can adsorb to the interface.

By the term "BslA" we refer to the wild-type biofilm-surface layer protein A (BslA) of *Bacillus subtilis* (SEQ ID NO: 1), known as WT-BslA, and variants (including fragments) thereof.

"Variants" of a protein such as BslA, as used herein, includes a sequence resulting when a protein is modified by, or at, one or more amino acids (for example 1, 2, 5 or 10 amino acids).

The invention includes variants in the form of truncated forms derived from wild type BslA, such as a protein having the sequence of SEQ ID NO:2. SEQ ID NO:2 corresponds to the sequence of full length 'wild type' BslA, but with the N-terminal signal sequence (amino acids 1 to 28) and 13 amino acids of the N-terminal region of mature BslA removed; truncated $BslA_{42-181}$ retains wild type properties in terms of its ability to adsorb at an interface and to stabilise that interface, and thus removal of the signal sequence and extreme N-terminal 13 amino acids of the mature protein does not appear to be in any way deleterious.

It is important that variants of BslA retain the ability of the wild type protein to adsorb at an interface and to stabilise that interface. Methods that can be used to determine adsorption of a protein to an interface and whether the protein lowers the interfacial tension (thereby stabilising the interface) are disclosed herein. Some performance drop in a given property of variants may of course be tolerated, but the variants should retain suitable properties for the relevant application for which they are intended. Screening of variants of SEQ ID NO:1 can be used to identify whether they retain appropriate properties.

The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art.

In one example, one conservative substitution is included in the peptide, such as a conservative substitution in SEQ ID NO:1 or SEQ ID NO:2. In another example, 10 or fewer conservative substitutions are included in the peptide, such as five or fewer. A peptide or protein of the invention may therefore include 1, 2, 3, 4, 5, 6, 7, 8, 9, 10 or more conservative substitutions. A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using peptide synthesis methods, for example, as known in the art.

Examples of amino acids which may be substituted for an original amino acid in a protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

In one embodiment, the substitutions are among Ala, Val, Leu and Ile; among Ser and Thr; among Asp and Glu; among Asn and Gln; among Lys and Arg; and/or among Phe and Tyr.

Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

A variant includes a "modified protein" or "mutated protein" which encompasses proteins having at least one substitution, insertion, and/or deletion of an amino acid. A modified or mutated protein may have 1, 2, 3, 4, 5, 6, 7, 8, 9 or 10 or more amino acid modifications (selected from substitutions, insertions, deletions and combinations thereof).

In one embodiment the BslA may comprise a modified WT-BslA protein, wherein the two cysteine residues at positions 178 and 180 are substituted with non-cysteine residues.

The cysteine residues at positions 178 and 180 of the WT-BslA allow the protein to form multimers (i.e. dimers, tetramers, hexamers and potentially higher order oligomers) in solution due to the formation of disulfide bonds between the cysteine residues of adjacent WT-BslA monomers. These multimers are also surface active, if to a lesser extent than monomeric BslA.

The inventors have found that the introduction of a reducing agent, such as 2-mercaptoethanol or dithiothreitol, for example, increases the surface activity of BslA, observed in a reduction in the surface tension of the interface. Without wishing to be bound by theory, the inventors suggest that the reducing agent reduces the cysteine groups, thereby preventing the formation of disulfide bonds between individual BslA proteins, such that the BslA is monomeric in solution. Accordingly, the reduction of the cysteine groups within WT-BslA with a reducing agent improves the surfactant properties of BslA.

However, such reducing agents are not suitable for many applications. Accordingly, the provision of a modified BslA where the cysteine residues have been substituted with non-cysteine residues ensures that there is no possibility of disulfide bonds forming between BslA monomers due to the lack of sulfur atoms within the protein. Accordingly, the resultant mutant BslA provides increased surface activity over WT-BslA without requiring the application of reducing agents.

The cysteine residues may be substituted for any other amino acid that does not comprise a sulfur atom, and the modified BslA may correspond to SEQ ID NO:18. For example, the substitution may be to replace the cysteine residues with alanine residues (C178A/C180A), valine residues (C178V/C180V), leucine residues (C178L/C180L) or isoleucine residues (C178I/C180I). Suitably, the substitution does not effect the folding of the protein. Typically, the conformation of the modified protein is similar to the WT-BslA monomer. Preferably, the conformation of the modified protein is substantially the same as the WT-BslA monomer in solution.

Preferably, the cysteine residues are substituted with alanine residues and the modified BslA corresponds to SEQ ID NO:20.

The invention also covers any fragment of SEQ ID NO: 1 that can adsorb to an interface and to stabilise that interface. According to the invention, the term "fragment" is intended to mean an amino acid sequence of at least 30, 60, 100, 150 contiguous amino acids of the reference sequences or any integer therebetween. For example, the invention includes truncated forms of the wild type BslA (e.g. $BslA_{42-181}$, SEQ ID NO 2).

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula $CONR^1R^2$ wherein $R^1$ and $R^2$ are each independently H or C1-C6 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C6 alkyl or dialkyl amino or further converted to an amide. Hydroxyl groups of the peptide side chains may be converted to alkoxy or ester groups, for example C1-C6 alkoxy or C1-C6 alkyl ester, using well-recognized techniques. Phenyl and phenolic rings of the peptide side chains may be substituted with one or more halogen atoms, such as F, Cl, Br or I, or with C1-C6 alkyl, C1-C6 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

The sequence of a variant of BslA according to the present invention is preferably at least 50% identical to wild-type BslA ("WT-BslA", SEQ ID NO 1) or truncated $BslA_{42-181}$ (SEQ ID NO 2), more preferably at least 60% identical, yet more preferably 70% identical, 75% identical, 80% identical, 90% identical, 95% identical, or even 99% identical. For the purpose of the present invention, these variant BslA proteins possessing this high level of identity to wild-type BslA are also embraced within the term "BslA". Furthermore, the person skilled in the art will understand that the term BslA includes homologs and orthologues of BslA that have similar amino acid sequences and that stabilise the interface between two phases in a synthetic multiphase product.

The term "sequence identity" refers to the identity between two or more amino acid sequences and is expressed in terms of the identity or similarity between the sequences. Sequence identity can be measured in terms of percentage identity; the higher the percentage, the more identical the sequences are. The percentage identity is calculated over the length of comparison, e.g. in the present invention it is typically calculated over the entire length of a sequence aligned against the entire length of SEQ ID NO 1 or 2. Homologs or orthologues of amino acid sequences typically possess a relatively high degree of sequence identity when aligned using standard methods.

Methods of alignment of sequences for comparison are well known in the art and identity can be calculated by many known methods. Various programs and alignment algorithms are described in the art.[2-10] It should be noted that the terms 'sequence identity' and 'sequence similarity' are often used inconsistently and interchangeably in the art.

Identity, or homology, percentages as mentioned herein in respect of the present invention are those that can be calculated with the GAP program, obtainable from GCG (Genetics Computer Group Inc., Madison, Wis., USA). Alternatively, a manual alignment can be performed.

For polypeptide sequence comparison the following settings can be used:
  Alignment algorithm: Needleman and Wunsch, J. Mol. Biol. 1970, 48: 443-453.
  As a comparison matrix for amino acid similarity the Blosum62 matrix is used (Henikoff S. and Henikoff J. G., P.N.A.S. USA 1992, 89: 10915-10919).
  The following gap scoring parameters are used:
    Gap penalty: 12
    Gap length penalty: 2
    No penalty for end gaps.

A given sequence is typically compared against the full-length sequence of SEQ ID NO 1 or 2 to obtain a score.

The NCBI Basic Local Alignment Search Tool (BLAST)[10] is available from several sources, including the National Center for Biological Information (NCBI, National Library of Medicine, Building 38A, Room 8N805, Bethesda, Md. 20894,US) and on the Internet, for use in connection with the sequence analysis programs blastp, blastn, blastx, tblastn and tblastx. Additional information can be found at the NCBI web site. BLAST can suitably be used for identifying homologs and compare sequences. For comparisons of amino acid sequences of greater than about 30 amino acids, the Blast 2 sequences function can suitably be employed using the default BLOSUM62 matrix set to default parameters (gap existence cost of 12, and a per residue gap cost of 2). Homologs are typically characterised by possession of at least 50% sequence identity counted over the full-length alignment with an amino acid sequence using the NCBI Basic Blast 2.0, gapped blastp with databases such as the nr or swissprot database. Proteins with even greater similarity will show increasing percentage identities when assessed by this method, such as at least 60%, 70%, 75%, 80%, 85%, 90%, 95%, or 99% sequence identity. Queries searched with the blastn program can be filtered with DUST.[11]

Exemplary orthologues identified though sequence identity searches include:
  yuaB from *B. licheniformis* (NCBI Reference Sequence: YP_006715276.1) SEQ ID NO. 22
  yuaB from *B. amyloliquefaciens* (NCBI Reference Sequence: YP_001422381.1) SEQ ID NO. 23
  yuaB from *B. pumilus* (NCBI Reference Sequence: YP_001486852.1) SEQ ID NO. 24.

These proteins, from other *bacillus* species, have a sequence identity within the above ranges. They putatively display similar properties to BslA, and preliminary in vitro results support the supposition that they can perform a similar function at an interface to that observed for BslA. Accordingly these represent exemplary orthologues falling within the scope of the invention, and in some cases may be preferred embodiments of the invention. It will be apparent to the skilled person that there may be, and indeed are likely to be, other orthologues and/or homologues which can be identified through bioinformatics or conventional molecular biology techniques, and that such proteins will likely have conserved functionality. Accordingly, the three orthologues above should not be viewed as limiting examples.

An example of an exemplary homologue is YweA from *B. subtilis* SEQ ID NO. 28 (full length) and SEQ ID NO:29 (truncated). YweA has been found to be surface active and to undergo a similar conformational change at an interface between two phases to that of WT-BslA.

The present invention includes protein variants which include additional sequences (e.g. attached at the N or C terminus of the BslA variant), such as fusion proteins or the like, provided they retain the ability of the wild type protein to adsorb at an interface and to stabilise that interface. Where a protein variant includes additional amino acid sequences then these sequences can be disregarded from the point of view of calculating the relevant sequence identity. One can envisage the incorporation of additional sequences corresponding to, for example, a tag to assist in purification or other processing steps, a fusion protein whereby a protein with desirable properties is fused to the BslA variant, a fluorescent protein domain, or the like. Including such additional sequences in a sequence comparison could result in inappropriate results. Sequence comparison tools, such as BLAST, are adapted to easily address this, e.g. by disregarding sequences beyond the region of comparison and/or by permitting sequence extension with no penalty. Of course, such additional sequences would need to be added with care so as not to harm the desirable surface active properties of the BslA proteins of the present invention.

In some preferred embodiments the BslA protein of the present invention does not include any non-conservative substitutions or other destabilising amino acid changes in the hydrophobic cap. More preferably the BslA protein does not include any sequence changes in the hydrophobic cap. Non-conservative changes in the hydrophobic cap typically interfere with the formation of a large scale 2D lattice, which can be highly desirable.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature.[12-25]

In addition, Hobley et al. (PNAS vol. 110, no. 33, 13600-13605, August 2013)[1] describes methods and materials regarding the expression and quantification of BslA, and substitutions and mutants of BslA used herein, and is hereby incorporated by reference.

Preferably, the synthetic multiphase product comprises isolated BslA. Isolated BslA can be obtained by extraction from native sources, such as *Bacillus subtilis* by any suitable process.

The term "isolated" refers to a biological component (such as a nucleic acid molecule or protein) that has been substantially separated or purified away from other biological components in the cell of the organism in which the component naturally occurs, i.e., other chromosomal and extrachromosomal DNA and RNA, lipids, proteins, and sugars etc. Nucleic acids and proteins that have been "isolated" include nucleic acids and proteins purified by standard purification methods.

Alternatively, isolated BslA can be obtained by the use of recombinant technology. For example, host cells can be modified to express BslA and the BslA can be isolated and used in accordance with the present invention. Recombinant technology can also be used to modify BslA sequences or synthesise novel BslA variants having desired/improved properties. Typically, an appropriate host cell or organism is transformed by a nucleic acid construct that encodes the desired property. The methods required to construct these expression vectors are well known to those skilled in the art.

The BslA used to stabilise a synthetic multiphase product may comprise more than one BslA type. The BslA may comprise a mixture of BslA types. The BslA may comprise a mixture of WT-BslA and one or more variants or mutant BslA. For example, the BslA may comprise a mixture of WT-BslA and BslA-L77K. In an alternative example, the BslA may comprise a mixture of WT-BslA and a modified BslA, as defined below.

The synthetic multiphase product may suitably comprise at least 0.005 wt % BslA. Preferably, the synthetic multiphase product comprises at least 0.01 wt % BslA. More preferably, the synthetic multiphase product comprises at least 0.02 wt % BslA.

The synthetic multiphase product may suitably comprise between 0.005 and 0.2 wt % BslA. Preferably, the synthetic multiphase product comprises between 0.01 and 0.2 wt % BslA. More preferably, the synthetic multiphase product comprises between 0.02 and 0.2 wt % BslA.

In some embodiments, BslA may be primarily acting as a foaming agent or an emulsifier, and it may be that the minimum concentration of BslA required to act as a foaming agent or emulsifier may differ from the minimum concentration of BslA required to stabilise a foam or emulsion. For example, a liquid comprising BslA may require at least 0.02 wt % BslA to foam to produce the synthetic multiphase product, and foam formed using another foaming agent may require at least 0.005 wt % BslA to stabilise the foam.

Alternatively, in some embodiments, BslA may be primarily acting as a stabilising agent, and it may be that the minimum concentration of BslA required to act as a stabilising agent may be different to the minimum concentration of BslA required to foam or emulsify a liquid composition to form a synthetic multiphase product.

Concentrations of BslA outside of the ranges mentioned above may, of course, be useful in various situations, and the invention contemplates uses at such concentrations.

Typically, the BslA is added to the synthetic multiphase product in a form and in an amount such that it is available to adsorb to, and stabilise, the interface between phases within the synthetic multiphase product. By the term "added" we refer to BslA being deliberately introduced to the synthetic multiphase product for the purpose of taking advantage of its interfacial stabilising properties. Accordingly, the term "added" does not include adding components to the synthetic multiphase product that may be contaminated with the bacteria *Bacillus subtilis*, for example.

BslA may be more resistant to displacement from the interface by competing surfactants once BslA has self-assembled to form the viscoelastic film at the interface. Therefore, BslA may stabilise the interface of the synthetic multiphase product in the presence of competing surfactants.

In contrast, some known surfactants, such as protein surfactants may not be able to stabilise the interface between phases of synthetic multiphase products in the presence of competing surfactants. Therefore, synthetic multiphase products comprising BslA may be more stable in the presence of competing surfactants than synthetic multiphase products that comprise alternative protein surfactants.

The synthetic multiphase product may comprise BslA and at least one co-surfactant. Preferably, the co-surfactant is unable to substantially displace BslA from the interfaces of the synthetic multiphase product. Therefore, the BslA may still form a viscoelastic film at the interfaces of the synthetic multiphase product. For example, synthetic multiphase products that are emulsions or foams and comprise BslA and a co-surfactant according to the invention, will form non-spherical droplets or bubbles at a solid interface after shearing due to the viscoelastic film of BslA preventing the interface from relaxing after distortion.

The co-surfactant may be an anionic co-surfactant. The co-surfactant may be a cationic co-surfactant. Preferably, the co-surfactant is a non-ionic co-surfactant.

The co-surfactant may be a polymeric surfactant. For example, the co-surfactant may be a non-ionic polymeric surfactant. The co-surfactant may be an ionic polymeric surfactant.

Preferably, the co-surfactant is a protein surfactant. For example, the co-surfactant may be sodium caseinate, the surfactants within whey protein isolate, or a hydrophobin. More preferably, the co-surfactant is sodium caseinate.

Some surfactants, such as sodium caseinate, are good foaming agents and emulsifiers, but the foams or emulsions they produce are typically not stable over long time periods. The inventors have surprisingly found that a multiphase system comprising a foaming agent or emulsifier, such as sodium caseinate, may be stabilised by the addition of BslA to form a more stable synthetic multiphase product than a synthetic multiphase product with the foaming agent or emulsifier, such as sodium caseinate, alone.

Often, the stabilising action of foam and emulsion stabilising agents is disrupted if a co-surfactant, such as a foaming agent or emulsifier, is present. For example, hydrophobins can be used to provide stability to a foam, but do not typically work when a co-surfactant is present, such as sodium caseinate and/or the surfactants within whey protein isolate.

Without wishing to be bound by theory, the foaming agents or emulsifiers (co-surfactants) may prevent typical foam or emulsion stabilising agents adsorbing to the multiphase interface, and thereby preventing them from providing any stability to that interface.

Surprisingly, the inventors have found that BslA is able to competitively adsorb to the interfaces within a synthetic multiphase product, and to thereby stabilise the synthetic multiphase product.

Therefore, the provision of a synthetic multiphase product that comprises BslA and a co-surfactant foaming agent or emulsifier, ensures that the synthetic multiphase product is highly foamable or forms a finer emulsion (smaller droplets within the emulsion), and the foam or emulsion of the synthetic multiphase product is more stable than would be produced using the co-surfactant foaming agent or emulsifier alone. For example, synthetic multiphase products made using the combination of BslA and sodium caseinate according to the present aspect may be more stable for a given concentration of surfactant used than those comprising sodium caseinate alone known in the art.

It will be understood by the person skilled in the art that whilst BslA may be acting primarily as a stabilising agent in synthetic multiphase products that also comprise a foaming agent or emulsifier, BslA will also be acting as a foaming agent or emulsifier to some degree, if to a lesser extent than the foaming agent or emulsifier.

The synthetic multiphase product may comprise three or more intimately mixed immiscible phases of matter. For example, the synthetic multiphase product may comprise a water-in-oil-in-water emulsion where water droplets are suspended in oil droplets that are themselves suspended in a bulk aqueous phase, or the synthetic multiphase product may comprise an oil-in-water-in-oil emulsion where oil droplets are suspended in water droplets that are themselves suspended in a bulk oil phase. Alternatively, the synthetic multiphase product may comprise an air-in-water-in-air system and as such, the synthetic multiphase product may comprise a plurality of bubbles.

In embodiments of the invention where the synthetic multiphase product comprises a first aqueous phase, an oil phase and a second aqueous phase within the oil phase, the second aqueous phase may comprise an active agent. The active agent may be sensitive to degradation, and may be protected from degradation within the second aqueous phase by the oil phase. For example, the active agent may be hydrophilic and readily oxidised, and retaining the second aqueous phase within the oil phase may reduce the extent or prevent the active agent being oxidised by external oxidising agents.

Alternatively, in embodiments where the synthetic multiphase product comprises a first oil phase, an aqueous phase, and a second oil phase within the aqueous phase, the second oil phase may comprise the active agent. The active agent may be sensitive to degradation, and may be protected from degradation within the second oil phase by the aqueous phase. For example, the active agent may be hydrophobic and readily oxidised, and retaining the second oil phase within the aqueous phase may reduce the extent or prevent the active agent being oxidised by external oxidising agents.

In embodiments where the synthetic multiphase product comprises three or more intimately mixed phases, the BslA may stabilise one or more of the three or more phases. The BslA may stabilise two or more of the three or more phases. The BslA may stabilise the interface between two or more of the three or more phases. The BslA may stabilise each interface between the three or more phases.

The synthetic multiphase product may a pharmaceutical composition or a pharmaceutical product. The active agent may be a pharmaceutical active agent. The synthetic multiphase product may allow the pharmaceutical active agent to more readily reach its target site. The synthetic multiphase product may allow a greater concentration of the pharmaceutical active agent to reach its intended target site. For example, the synthetic multiphase product may allow the pharmaceutical active agent to be protected from degradation within the body of the patient and therefore, allow a greater concentration of the pharmaceutical active agent to reach its target site for a given concentration of pharmaceutical active agent taken by the patient.

Accordingly, a synthetic multiphase product comprising three phases and a pharmaceutical active agent may be a more cost effective method of drug delivery than those known in the art.

In embodiments where the synthetic multiphase product comprises solid particles and a liquid phase, the solid particles may tend to aggregate together and fall out of solution. For example, the particles may be hydrophobic and the liquid phase may be an aqueous phase, or the particles may be hydrophilic and the liquid phase may be an oil phase. The BslA may adsorb to the surface of the particles. In embodiments where the particles are hydrophobic, the hydrophobic cap of the BslA may be adsorbed to the surface of the particle such that the hydrophilic portion of BslA extends away from the surface of the particle into the liquid phase, thereby making the particles more hydrophilic and therefore, more stable in an aqueous phase, for example. Alternatively, in embodiments where the particles are hydrophilic, the hydrophilic portion of BslA may adsorb to the surface of the particles such that the hydrophobic cap extends away from the surface of the particle into the liquid phase, thereby making the particles more hydrophobic and therefore, more stable in an oil phase. The BslA may form a film or layer over the surface of the particle. Accordingly, the addition of BslA to a sol or suspension of particles may stabilise the sol or suspension.

In some embodiments of the invention the BslA may be covalently or non-covalently linked to a solid particle. Means of linking a protein to a solid are well known in the art. For example, the presence of a Cys residue towards either the C terminus of BslA provides a convenient method of attachment to a solid. Known methods for modifying a surface to facilitate protein coating include physical modification, chemical modification, photochemical modification, and plasma treatment; see, for example, Vasita, Rajesh; Shanmugam, I. K.; Katt, D. S. (2008). "Improved biomaterials for tissue engineering applications: surface modification of polymers". *Current Topics in Medicinal Chemistry* 8 (4): 341-353, and Morra, M.; Cassinelli, C. (2006). "Biomaterials surface characterization and modification". *The International Journal of Artificial Organs* 29 (9): 824-833.

Alternatively, the protein can be linked though non-covalent means, e.g. protein/protein interactions, ionic interactions, etc. For example, a surface can be coated with biotin/avidin and the protein of the present invention can be a fusion with the corresponding biotin/avidin molecule to enable it to bind to the surface.

According to a second aspect of the invention, there is provided a method of manufacture of a synthetic multiphase product according to the first aspect of the invention comprising the steps of:
 a providing the one or more components of the synthetic multiphase product;
 b adding BslA to the one or more components of the synthetic multiphase product; and
 c mixing the one or more components to form the synthetic multiphase product.

Typically, the one or more components of the synthetic multiphase product are immiscible phases of matter that may be mixed to form a multiphase system, such as those within the synthetic multiphase products made using the method of the present aspect of the invention. For example, where the synthetic multiphase product is an emulsion, the one or more components of the synthetic multiphase product may be an aqueous phase and an oil phase, and the step of mixing the oil phase and aqueous phase after the addition of BslA may form a stable emulsion, the synthetic multiphase product. In another example, where the synthetic multiphase product is a foam, the one or more components may be a liquid phase and the step of mixing the liquid phase after the addition of BslA may mix air into the liquid phase, thereby forming a foam, the synthetic multiphase product. In a further example, where the synthetic multiphase product is a frozen synthetic multiphase product, the one or more components may be a liquid phase at room temperature and a solid phase when frozen (i.e. below the freezing point for the liquid, typically significantly below room temperature), and the step of mixing the one or more components may be carried out at room temperature and the resulting mixture subsequently frozen. The step of mixing the one or more components after the addition of BslA may mix air into the one or more components, thereby forming a foam that is subsequently frozen.

The synthetic multiphase product may be a multiphase food product. The multiphase food product may be an aerated food product. That is, the multiphase food product may be a food product through which a gas, such as nitrogen, carbon dioxide, nitrous oxide, or air, has been passed to produce a foamed food product. For example, the foamed food product may be a mousse, ice cream or whipped cream. The multiphase food product may be a foamable food product, such that the foamable food product is typically a liquid and when a neutral gas is passed through the liquid by injection into the liquid, or agitation of the liquid, a foam is produced. For example, whipped cream can be made by passing nitrous oxide through the cream mixture in a whipping syphon. The multiphase food product may be an emulsified food product, such as mayonnaise, a vinaigrette, or cream, for example.

The multiphase food product may be a frozen multiphase food product. The multiphase food product may be a frozen emulsified food product, such as ice cream. The multiphase food product may be an aerated frozen multiphase product. That is, the multiphase food product may be a frozen food product through which, during preparation, a gas, such as nitrogen, carbon dioxide, nitrous oxide or air, has been passed to produce a foamed food product that has then been frozen. For example, the frozen multiphase food product may be a foamed ice cream.

The synthetic multiphase product may be a personal care product. The multiphase personal care product may be an aerated personal care product, such as shaving foam, for example. The multiphase personal care product may be a foamable personal care product, such that the foamable personal care product is a liquid and when a gas is passed through the liquid, such as by agitation or by forcing a neutral gas through the liquid, a foam or lather is produced. For example, the foamable personal care product may be a shampoo, soap, or shower gel. The multiphase personal care product may be an emulsified personal care product, such as hand cream, or moisturiser, for example.

In some embodiments of the invention, the addition of BslA to the components of the synthetic multiphase product may increase the foamability of a liquid, wherein the liquid forms a foam multiphase system when mixed with a gas.

In embodiments where the synthetic multiphase product is foamable synthetic multiphase product, such as shampoo or the cream mixture that is whipped into whipped cream, the step of mixing the one or more components to form a foam may be carried out by the user. For example, shampoo is typically sold as a liquid mixture of one or more components and the user agitated the liquid mixture to form a foam or lather during use. In another example, whipped cream is typically sold as a liquid mixture of one or more components and the user agitates the mixture, or injects a gas into the mixture, to form the whipped cream. Accordingly, in these embodiments, BslA is added to increase the foamability of the one or more components to ensure that a good foam is produced when the mixture of the one or more components and BslA is agitated by the user, for example.

Preferably, the BslA added to the one or more components enhances the ability of the one or more components to mix together to form a multiphase system. For example, in embodiments where the synthetic multiphase product is a foam, the step of adding BslA to the one or more components may increase the foamability of the one or more components. In another example, in embodiments where the synthetic multiphase product is an emulsion, the step of adding BslA to the one or more products may increase the ability of the one or more components to form an emulsion during the step of mixing.

Preferably, the BslA added to the one or more components enhances the stability of the synthetic multiphase product formed once the one or more components are mixed together. For example, in embodiments where the synthetic multiphase product is a foam, the step of adding BslA to the one or more components may increase the stability of the foam produced during the step of mixing. In another example, in embodiments where the synthetic multiphase product is an emulsion, the step of adding BslA to the one or more components may increase the stability of the emulsion produced during the step of mixing.

The key role of BslA may vary between synthetic multiphase products manufactured using the method of the present aspect of the invention. For example, in some embodiments, the key role of BslA may be to increase the tendency of the one or more components to form a foam or emulsion during the step of mixing. In another example, in some embodiments, the key role of BslA may be to stabilise the synthetic multiphase product after the step of mixing.

However, the person skilled in the art will appreciate that BslA will be acting as both a stabiliser and a foaming or emulsifying agent in each application to a greater or lesser degree.

The ability of BslA to adopt a first conformation that is soluble in aqueous solution results in BslA being more readily handled and used in methods of manufacture of synthetic multiphase products than alternative protein surfactants in the art, such as sodium caseinate, those present in whey protein isolate, and, especially, hydrophobins, for example.

As discussed above, once BslA has changed from the first conformation to a second conformation, where a hydrophobic cap is formed, BslA adsorbs to the interface between the phases of the synthetic multiphase product and self-assembles to form a two dimensional rectangular lattice. The inventors have found that the formation of a two dimensional rectangular lattice corresponds to the formation of a viscoelastic film at the interface between phases, and provides enhanced stability of that interface.

Typically, in embodiments where the synthetic multiphase product made using the method of the present aspect is a food product or a frozen food product, such food products typically comprise an emulsion or a foam and are required to be stable over a long period of time, such as a week, or a month, or multiple months, for example.

Accordingly, the addition of BslA to the one or more components of the synthetic multiphase product increases the stability of the synthetic multiphase product, and thereby increases the shelf life of the said product.

At least one of the one or more components may comprise one or more co-surfactants. The one or more co-surfactants may be a stabilising agent. The one or more co-surfactants may be a foaming agent or an emulsifier. The one or more co-surfactants may have been added to the at least one component to improve the foaming or emulsifying properties of the one or more components, or to improve the stability of the synthetic multiphase product.

Alternatively, the one or more co-surfactants may be present within the at least one component. For example, at least one or the one or more components may comprise a milk product. The milk product may comprise milk proteins, such as sodium caseinate or whey protein isolate.

The presence of these milk proteins often interferes or prevents some surfactants known in the art from being effective. For example, in embodiments where the synthetic multiphase product comprises a foam, the presence of milk proteins may prevent or inhibit some surfactants from improving the foamability of the at least one component that comprises the milk proteins, or increasing the stability of the foam of the synthetic multiphase product.

However, BslA is able to stabilise synthetic multiphase products that have been made by mixing one or more components, at least one of which comprise milk proteins. Therefore, the provision of the method of manufacturing according to the present aspect allows synthetic multiphase products to be made from at least one component that contains milk proteins without the addition of a further surfactant. Accordingly, the method of the present invention is more efficient and cost effective than those known in the art for synthetic multiphase products comprising milk proteins.

The method of the present aspect of the invention is particularly effective in embodiments where the synthetic multiphase product comprises one or more components containing sodium caseinate.

In embodiments where the synthetic multiphase product is a food product or a frozen food product, the one or more components may comprise milk proteins, sugars, carbohydrates such as flour, egg proteins and/or fats, and these synthetic multiphase products may be stabilised by BslA.

In a third aspect of the invention, there is provided the use of BslA to modify the hydrophilicity of a surface.

Typically, the surface is the surface of a substrate such as a particulate or a macroscopic object. For example, the surface may be the surface of particulates that are to be suspended in a liquid phase. In another example, the surface may be the surface of a glass slide or plastic sheet.

The use of BslA may increase the hydrophilicity of the surface, such that the surface is more readily wetted by an aqueous phase. For example, in embodiments where the surface is the surface of a macroscopic object, the use of BslA to increase the hydrophilicity of the surface may reduce the contact angle of a droplet of water on the surface.

The use of BslA may decrease the hydrophilicity of the surface, such that the surface is more resistant to wetting by an aqueous phase. For example, in embodiments where the surface is the surface of a macroscopic object, the use of BslA to decrease the hydrophilicity of the surface may increase the contact angle of a droplet of water on the surface.

In embodiments where the surface is the surface of a particulate, the use of BslA may allow the particulate to form a more stable suspension in an aqueous medium or phase by increasing the hydrophilicity of the surface of the particulate. Alternatively, the use of BslA may allow the particulate to form a more stable suspension in an oil phase by decreasing the hydrophilicity of the surface of the particulate.

Without wishing to be bound by theory, surfaces that are hydrophobic (that is, have a low hydrophilicity) may bind the hydrophobic cap of BslA such that the hydrophilic portion of the protein extends away from the surface, or such that the hydrophobic surface is shielded from an aqueous phase. In this way, the addition of BslA to the surface may increase the hydrophilicity of the surface. Alternatively, a hydrophilic surface may bind to portion of the hydrophilic part of BslA such that the hydrophobic cap extends away from the surface. In this way, the addition of BslA to the surface may decrease the hydrophilicity of the surface. The BslA may form a film or layer over the surface of the particle. Accordingly, the addition of BslA to a sol or suspension of particles may stabilise the sol or suspension.

According to a fourth aspect of the invention, there is provided a composition of particles of a first material, the particles comprising a coating of BslA over at least a portion of the (preferably substantially the entire) surface of the particles, wherein the particles within the composition of particles are more hydrophilic than particles of the first material that do not comprise a coating of BslA over the surface of the particles.

Suitably, the first material may comprise an intimate mixture of different chemical compounds formulated into particles.

For example, the composition of particles may form a more stable suspension in aqueous media than a composition of particles of the first material, the particles of which do not comprise a coating of BslA over the surface of the particles.

Typically, the first material is hydrophobic.

According to a fifth aspect of the invention, there is provided a pharmaceutical composition comprising particles, each particle comprising an active agent, and the surface of each particle comprises BslA, such that the stability of a suspension of the particles in an aqueous phase is improved.

Preferably, the BslA forms a coating around the surface of each particle. The coating of BslA may form a film around the particle. The film may be a viscoelastic film. Typically, the coating around the surface of each particle comprises sufficient BslA to form a substantially continuous film around the particle.

Pharmaceutical compositions may comprise components or active agents that have a low hydrophilicity, and are therefore, difficult to prepare and deliver to a patient without the use of additional components such as suitable excipients, diluents etc.

Typically, components or active agents that are hydrophobic are milled down to nanoparticles and then stabilised in suspension with a stabilising agent such as a polymer, for example.

The provision of a pharmaceutical composition comprising BslA-coated particulates may allow normally hydrophobic active agents, for example, to be directly suspended in an aqueous medium suitable for delivery to the patient, without requiring the components or active agents to be milled, for example.

In a further aspect the invention provides a solid object having a surface which has been modified by providing, e.g. coating the surface with, BslA according to the present invention to at least a portion of the surface. Some or all of the surfaces of the solid may be at least partially coated with BslA. The object is preferably a synthetic object, and excludes a natural biofilm or an object partially or completely covered by a natural biofilm. The BslA can be adsorbed to the surface or can be linked to the surface in a non-covalent or covalent manner all of these methods are within the term 'coating' as used above. Methods of linking a protein to a surface are well known in the art, and some exemplary methods are discussed above.

According to a seventh aspect of the invention, there is provided a frozen synthetic multiphase product comprising BslA.

The frozen synthetic multiphase product may comprise at least one co-surfactant. Preferably, the co-surfactant is unable to substantially displace BslA from the interfaces of the frozen synthetic multiphase product. Therefore, the BslA may still form a viscoelastic film at the interfaces of the frozen synthetic multiphase product. For example, frozen synthetic multiphase products that are frozen emulsions or foams and comprise BslA and a co-surfactant according to the invention, will form non-spherical droplets or bubbles at a solid interface after shearing due to the viscoelastic film of BslA preventing the interface from relaxing after distortion.

The co-surfactant may be an anionic co-surfactant. The co-surfactant may be a cationic con-surfactant. Preferably, the co-surfactant is a non-ionic co-surfactant.

The co-surfactant may be a polymeric surfactant. For example, the co-surfactant may be a non-ionic polymeric surfactant. The co-surfactant may be an ionic polymeric surfactant.

Preferably, the co-surfactant is a protein surfactant. For example, the co-surfactant may be sodium caseinate, the surfactants within whey protein isolate, or a hydrophobin. More preferably, the co-surfactant is sodium caseinate.

Some surfactants, such as sodium caseinate, are good foaming agents and emulsifiers, but the foams or emulsions they produce are typically not stable over long time periods. The inventors have surprisingly found that a frozen multiphase system comprising a foaming agent or emulsifier, such as sodium caseinate, or casein in a micelle form, may be stabilised by the addition of BslA to form a more stable synthetic multiphase product than a synthetic multiphase product with the foaming agent or emulsifier, such as sodium caseinate or casein in a micelle form, alone.

Often, the stabilising action of foam and emulsion stabilising agents is disrupted if a co-surfactant, such as a foaming agent or emulsifier, is present. For example, hydrophobins can be used to provide stability to a foam, but do not typically work when a co-surfactant is present, such as sodium caseinate and/or the surfactants within whey protein isolate.

It will be understood by the person skilled in the art that whilst BslA may be acting primarily as a stabilising agent in frozen synthetic multiphase products that also comprise a foaming agent or emulsifier, BslA will also be acting as a foaming agent or emulsifier to some degree, if to a lesser extent than the foaming agent or emulsifier.

The frozen synthetic product may comprise a one or more additional components. The one or more additional components may comprise milk proteins, sugars, carbohydrates such as flour, egg proteins and/or fats.

The invention extends in an eighth aspect to a modified BslA, wherein the modified BslA comprises the substitution of the cysteine residues at positions 178 and 180 for non-sulfur containing residues, wherein the modified BslA is monomeric in solution.

Preferably, the modified BslA corresponds to SEQ ID NO:18, wherein the cysteine residues at positions 178 and 180 have been substituted with "X", where X denotes any non-sulfur containing residue.

Residues that are considered to be sulfur containing residues are cysteine and methionine.

Adsorption of wild-type BslA (WT-BslA) to an interface is relatively slow and a proportion of WT-BslA has been shown to form dimers and higher oligomers in solution. WT-BslA comprises cysteine residues at positions 178 and 180. Without wishing to be bound by theory, the inventors suggest that the formation of dimers and higher oligomers is due to the formation of disulfide bonds between cysteine residues of adjacent BslA units, and that adsorption of these dimers at an interface may require the hydrophobic cap of one of the BslA units to project into the aqueous phase.

The modified BslA of the present aspect adsorbs at an interface at a faster rate than dimeric WT-BslA, and is more difficult to displace from the interface once adsorbed, and therefore, the modified BslA act as a more effective foaming agent and as a more effective stabiliser for multiphase systems than WT-BslA.

Preferably, the conformation of the modified BslA in solution is substantially the same as that of monomeric WT-BslA in solution. Accordingly, the substitution of the cysteine residues should not introduce a residue that alters the conformation of the protein.

Suitably, the modified BslA may correspond to SEQ ID NO. 20, wherein the cysteine residues have been substituted by alanine residues, and the resulting modified BslA may be referred to as "AxA-BslA", indicating that the residues that have been substituted into the sequence are alanine residues ("A").

The modified BslA includes AxA-BslA, BslA with other substitutions to replace the cysteine residues, and includes the same with additional variations within the sequence. Accordingly, "modified BslA" includes modified BslA with conservative substitutions as defined for the first aspect of the invention.

"Variants" of a modified BslA, as used herein, includes a sequence resulting when the modified BslA is further modified by, or at, one or more amino acids (for example 1, 2, 5 or 10 amino acids). The invention includes variants in the form of truncated forms derived from full length modified BslA (SEQ ID NO:19), such as a modified BslA having the sequence of SEQ ID NO:21. SEQ ID NO:21 corresponds to the sequence of full length 'wild type' BslA with the cysteine residues at 178 and 180 substituted for alanine residues, an example of a substitution of cysteine for a non-sulfur containing residue, but with the N-terminal signal sequence (amino acids 1 to 28) and amino acids 29-41 removed (BslA$_{42-181}$ C178A/C180A). BslA$_{42-181}$ C178A/C180A retains wild type properties in terms of its ability to adsorb at an interface and to stabilise that interface, and thus removal of the signal sequence does not appear to be in any way deleterious.

It is important that variants of the modified BslA retain the ability of the wild type monomeric BslA to adsorb at an interface and to stabilise that interface. Methods that can be used to determine adsorption of a protein to an interface and whether the protein lowers the interfacial tension (thereby stabilising the interface) are disclosed herein. Some performance drop in a given property of variants may of course be tolerated, but the variants should retain suitable properties for the relevant application for which they are intended. Screening of variants of SEQ ID NO:18 can be used to identify whether they retain appropriate properties.

The variant may have "conservative" substitutions, wherein a substituted amino acid has similar structural or chemical properties to the amino acid that replaces it, for example, replacement of leucine with isoleucine. A variant may have "non-conservative" changes, for example, replacement of a glycine with a tryptophan. Variants may also include sequences with amino acid deletions or insertions, or both. Guidance in determining which amino acid residues may be substituted, inserted, or deleted without abolishing the activity of the protein may be found using computer programs well known in the art.

In one example, one conservative substitution is included in the peptide, such as a conservative substitution in SEQ ID NO:18 or SEQ ID NO:19. In another example, 10 or fewer conservative substitutions are included in the peptide, such as five or fewer. A peptide or protein of the invention may therefore include 1, 2, 3, 4, 5, 6, 7, 8, 9, 10 or more conservative substitutions. A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using peptide synthesis methods, for example, as known in the art.

Examples of amino acids which may be substituted for an original amino acid in a protein and which are regarded as conservative substitutions include: Ser for Ala; Lys for Arg; Gln or His for Asn; Glu for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

In one embodiment, the substitutions are among Ala, Val, Leu and Ile; among Ser and Thr; among Asp and Glu; among Asn and Gln; among Lys and Arg; and/or among Phe and Tyr. Further information about conservative substitutions can be found in, among other locations, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67796 (Curd et al.) and in standard textbooks of genetics and molecular biology.

A variant includes a "further modified protein" or "further mutated protein" which encompasses proteins having at least one additional substitution, an insertion, and/or a deletion of an amino acid. A further modified or mutated protein may have 1, 2, 3, 4, 5, 6, 7, 8, 9 or 10 or more additional amino acid modifications (selected from substitutions, insertions, deletions and combinations thereof).

The invention also covers any fragment of SEQ ID NO: 18 that can adsorb to an interface and to stabilise that interface. According to the invention, the term "fragment" is intended to mean an amino acid sequence of at least 30, 60, 100, 150 contiguous amino acids of the reference sequences or any integer therebetween.

The sequence of a variant of the modified BslA according to the present invention is preferably at least 50% identical to the modified wild-type BslA (SEQ ID NO 18) or modified truncated BslA (SEQ ID NO 19), more preferably at least 60% identical, yet more preferably 70% identical, 75% identical, 80% identical, 90% identical, 95% identical, or even 99% identical. For the purpose of the present invention, these variant BslA proteins possessing this high level of identity to modified wild-type BslA are also embraced within the term "further modified BslA". Furthermore, the person skilled in the art will understand that the term further modified BslA includes homologs and orthologues of modified BslA that have similar amino acid sequences and that stabilise the interface between two phases in a synthetic multiphase product.

The term "sequence identity" refers to the identity between two or more amino acid sequences and is expressed in terms of the identity or similarity between the sequences. Sequence identity can be measured in terms of percentage identity; the higher the percentage, the more identical the sequences are. The percentage identity is calculated over the length of comparison, e.g. in the present invention it is typically calculated over the entire length of a sequence aligned against the entire length of SEQ ID NO 18 or 19. Homologs or orthologues of amino acid sequences typically possess a relatively high degree of sequence identity when aligned using standard methods.

Methods of alignment of sequences for comparison are well known in the art and identity can be calculated by many known methods. Examples of such methods are described above in relation to the first aspect and are incorporated herein by reference.

The present invention includes protein variants which include additional sequences (e.g. attached at the N or C terminus of the modified BslA variant), such as fusion proteins or the like, provided they retain the ability of the wild type protein to adsorb at an interface and to stabilise that interface. Where a protein variant includes additional amino acid sequences then these sequences can be disregarded from the point of view of calculating the relevant sequence identity. One can envisage the incorporation of additional sequences corresponding to, for example, a tag to assist in purification or other processing steps, a fusion protein whereby a protein with desirable properties is fused to the modified BslA variant, a fluorescent protein domain, or the like. Including such additional sequences in a sequence comparison could result in inappropriate results. Sequence comparison tools, such as BLAST, are adapted to easily address this, e.g. by disregarding sequences beyond the region of comparison and/or by permitting sequence extension with no penalty. Of course, such additional sequences would need to be added with care so as not to harm the desirable surface active properties of the modified BslA proteins of the present invention.

In some preferred embodiments the modified BslA protein of the present invention does not include any non-conservative substitutions or other destabilising amino acid changes in the hydrophobic cap. More preferably the BslA protein does not include any sequence changes in the hydrophobic cap. Non-conservative changes in the hydrophobic cap typically interfere with the formation of a large scale 2D lattice, which can be highly desirable.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature.[12-25]

According to a tenth aspect of the invention, there is provided a composition comprising the modified BslA of the ninth aspect.

The composition may be multiphase product. The composition may be a synthetic multiphase product. The modified BslA may stabilise interfaces between phases in the multiphase product or synthetic multiphase product.

The synthetic multiphase product may comprise the modified BslA and at least one co-surfactant. Preferably, the co-surfactant is unable to substantially displace the modified BslA from the interfaces of the synthetic multiphase product. Therefore, the modified BslA may still form a viscoelastic film at the interfaces of the synthetic multiphase product. For example, synthetic multiphase products that are emulsions or foams and comprise the modified BslA and a co-surfactant according to the invention, will form non-spherical droplets or bubbles at a solid interface after shearing due to the viscoelastic film of the modified BslA preventing the interface from relaxing after distortion.

The co-surfactant may be an anionic co-surfactant. The co-surfactant may be a cationic con-surfactant. Preferably, the co-surfactant is a non-ionic co-surfactant.

The co-surfactant may be a polymeric surfactant. For example, the co-surfactant may be a non-ionic polymeric surfactant. The co-surfactant may be an ionic polymeric surfactant.

Preferably, the co-surfactant is a protein surfactant. For example, the co-surfactant may be sodium caseinate, the surfactants within whey protein isolate, or a hydrophobin. More preferably, the co-surfactant is sodium caseinate.

Some surfactants, such as sodium caseinate, are good foaming agents and emulsifiers, but the foams or emulsions they produce are typically not stable over long time periods. The inventors have surprisingly found that a multiphase system comprising a foaming agent or emulsifier, such as sodium caseinate, may be stabilised by the addition of the modified BslA to form a more stable synthetic multiphase product than a synthetic multiphase product with the foaming agent or emulsifier, such as sodium caseinate, alone.

Often, the stabilising action of foam and emulsion stabilising agents is disrupted if a co-surfactant, such as a foaming agent or emulsifier, is present. For example, hydrophobins can be used to provide stability to a foam, but do not typically work when a co-surfactant is present, such as sodium caseinate and/or the surfactants within whey protein isolate.

Without wishing to be bound by theory, the foaming agents or emulsifiers (co-surfactants) may prevent typical foam or emulsion stabilising agents adsorbing to the multiphase interface, and thereby preventing them from providing any stability to that interface.

Surprisingly, the inventors have found that modified BslA is able to competitively adsorb to the interfaces within a synthetic multiphase product, and to thereby stabilise the synthetic multiphase product.

Therefore, the provision of a synthetic multiphase product that comprises the modified BslA and a co-surfactant foaming agent or emulsifier, ensures that the synthetic multiphase product is highly foamable or forms a finer emulsion (smaller droplets within the emulsion), and the foam or emulsion of the synthetic multiphase product is more stable than would be produced using the co-surfactant foaming agent or emulsifier alone. For example, synthetic multiphase products made using the combination of the modified BslA and sodium caseinate according to the present aspect may be more stable for a given concentration of surfactant used than those comprising sodium caseinate alone known in the art.

The synthetic multiphase product may suitably comprise at least 0.005 wt % modified BslA. Preferably, the synthetic multiphase product comprises at least 0.01 wt % modified BslA. More preferably, the synthetic multiphase product comprises at least 0.02 wt % modified BslA.

The synthetic multiphase product may suitably comprise between 0.005 and 0.2 wt % modified BslA. Preferably, the synthetic multiphase product comprises between 0.01 and 0.2 wt % modified BslA. More preferably, the synthetic multiphase product comprises between 0.02 and 0.2 wt % modified BslA.

It will be understood by the person skilled in the art that whilst the modified BslA may be acting primarily as a stabilising agent in synthetic multiphase products that also comprise a foaming agent or emulsifier, the modified BslA will also be acting as a foaming agent or emulsifier to some degree, if to a lesser extent than the foaming agent or emulsifier.

The synthetic multiphase product may be a food product as described in the first aspect. The synthetic multiphase product may be a frozen food product as described in the first aspect or seventh aspect. The synthetic multiphase product may be an aerated food product as described in the first aspect.

The synthetic multiphase product may be a personal care product as described in the first aspect.

The composition may be applied to a surface to form a coating or film to the surface. The coating or film may change the properties of the surface. For example, the coating or film may adjust the hydrophobicity of the surface.

According to an eleventh aspect of the invention there is provided a method of producing a synthetic multiphase product comprising one or more components and the modified BslA according to the tenth aspect, the method comprising the steps:
  a providing the one or more components of the synthetic multiphase product;
  b adding BslA to the one or more components of the synthetic multiphase product; and
  c mixing the one or more components to form the synthetic multiphase product.

Typically, the one or more components of the synthetic multiphase product are immiscible phases of matter that may be mixed to form a multiphase system, such as those within the synthetic multiphase products made using the method of the present aspect of the invention. For example, where the synthetic multiphase product is an emulsion, the one or more components of the synthetic multiphase product may be an aqueous phase and an oil phase, and the step of mixing the oil phase and aqueous phase after the addition of BslA may form a stable emulsion, the synthetic multiphase product. In another example, where the synthetic multiphase product is a foam, the one or more components may be a liquid phase and the step of mixing the liquid phase after the addition of BslA may mix air into the liquid phase, thereby forming a foam, the synthetic multiphase product. In a further example, where the synthetic multiphase product is a frozen synthetic multiphase product, the one or more components may be a liquid phase at room temperature and a solid phase when frozen (i.e. below the freezing point for the liquid, typically significantly below room temperature), and the step of mixing the one or more components may be carried out at room temperature and the resulting mixture subsequently frozen. The step of mixing the one or more components after the addition of BslA may mix air into the one or more components, thereby forming a foam that is subsequently frozen.

The person skilled in the art will appreciate that the preferred and optional features of the second aspect of the invention are preferred and optional features of the eleventh aspect of the invention.

Embodiments of the present invention will now be described, by way of non-limiting example, with reference to the accompanying drawings.

Figure 5:
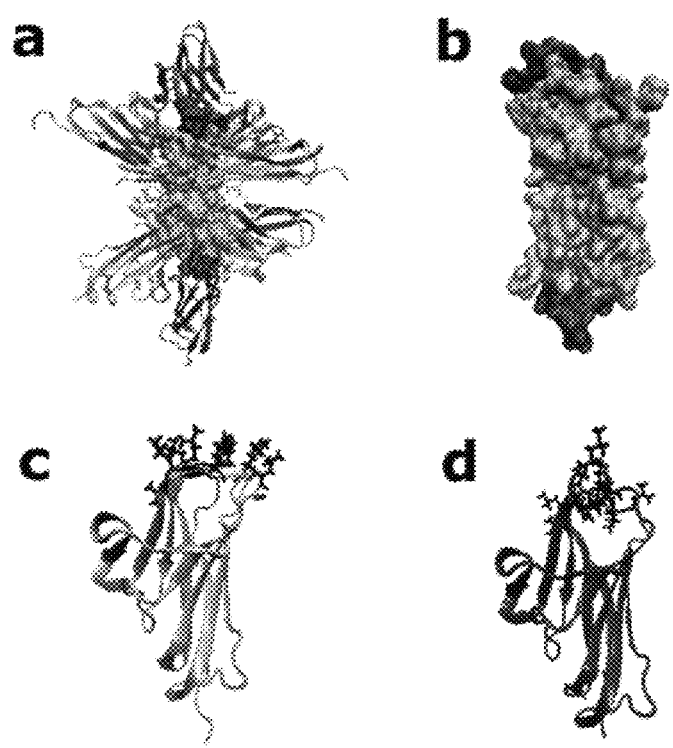
Figure 6:
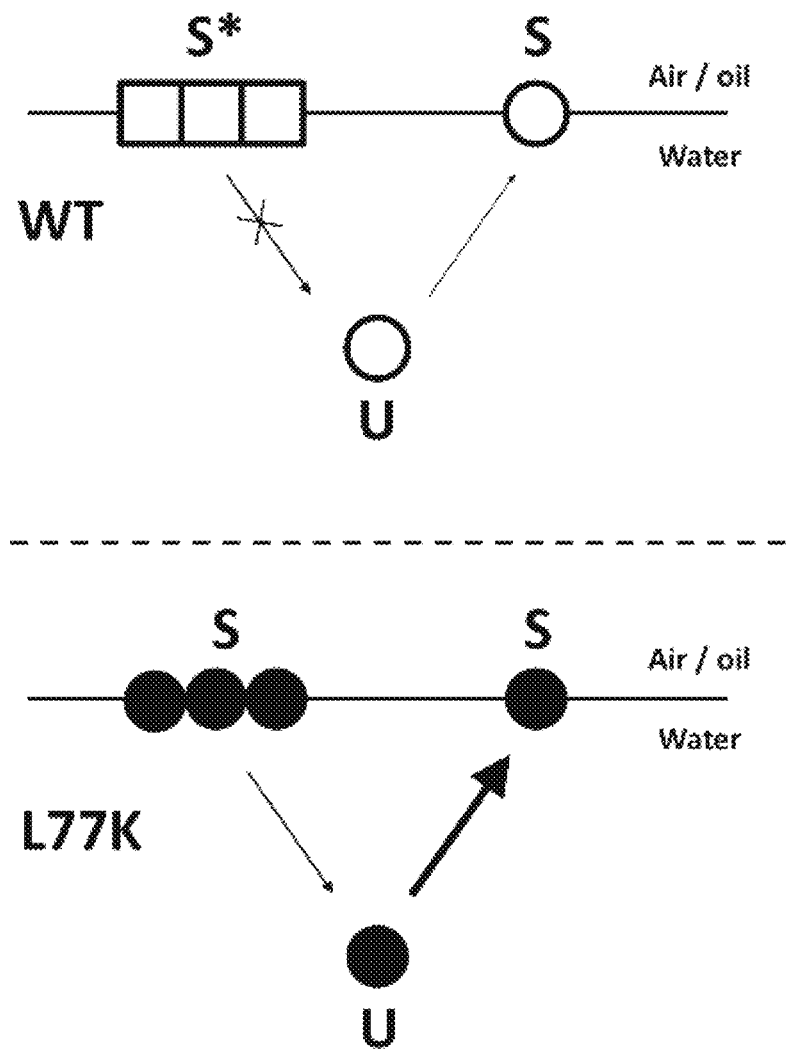
Figure 7:
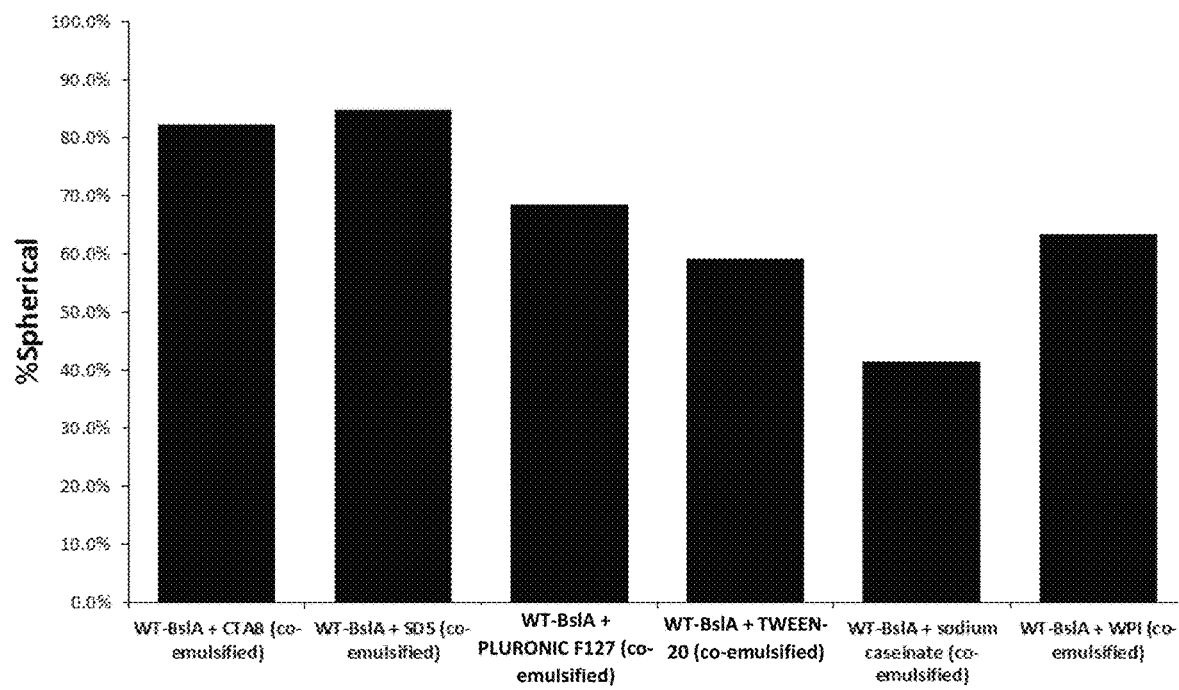
Figure 8:
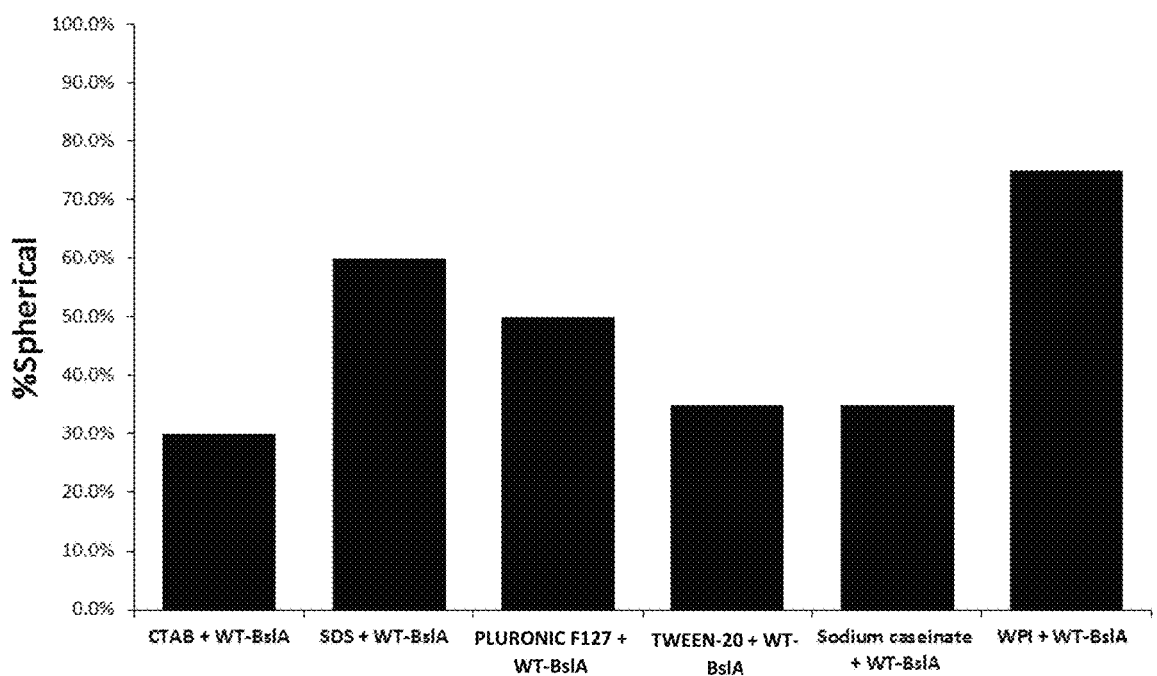
Figure 9:
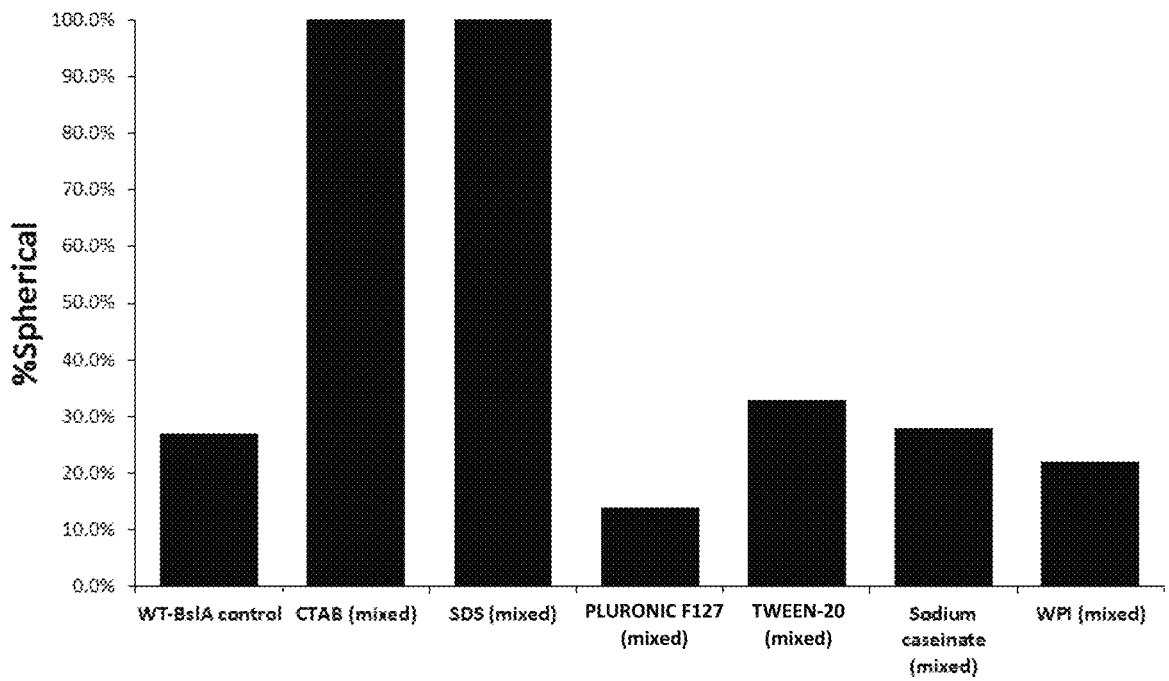
Figure 10:
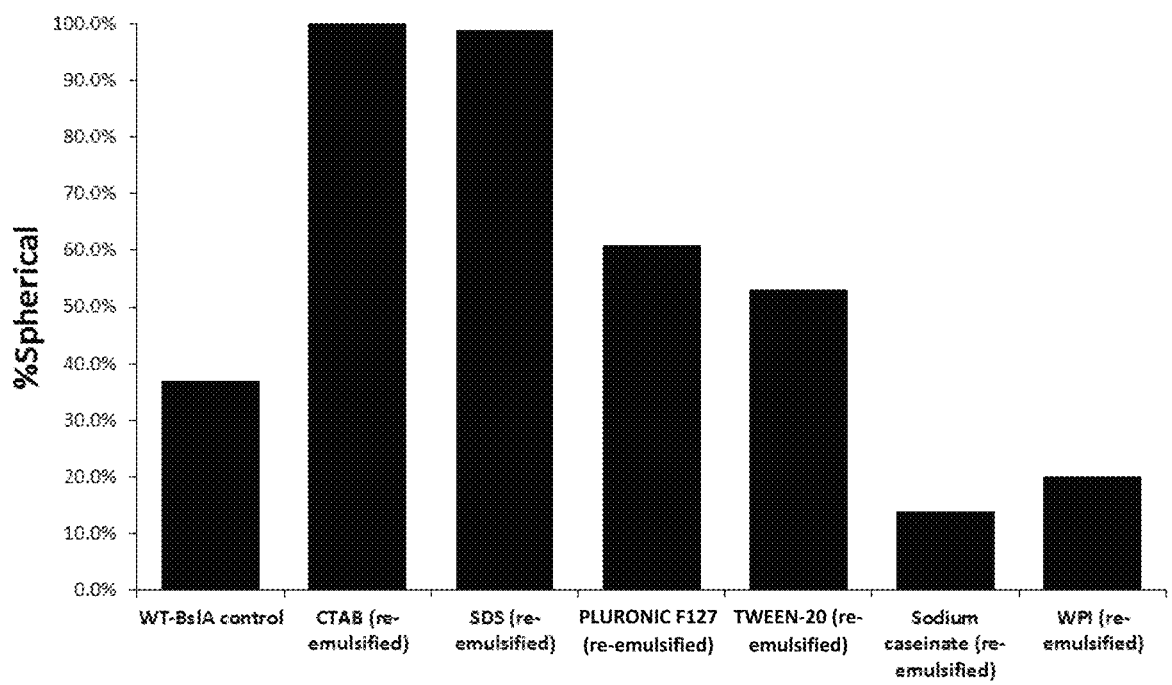
Figure 11:
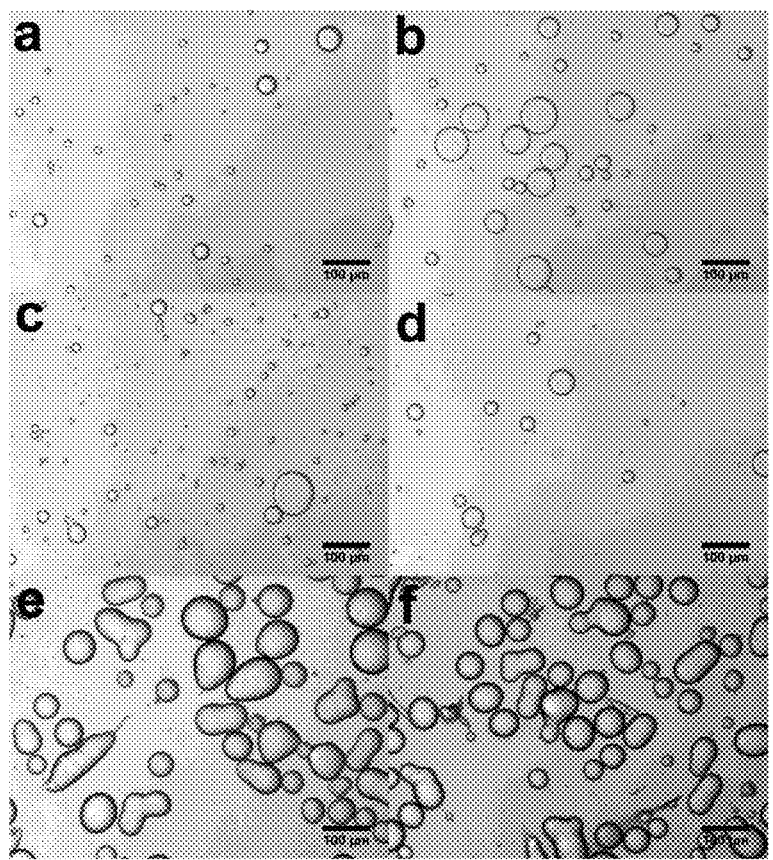
Figure 12:
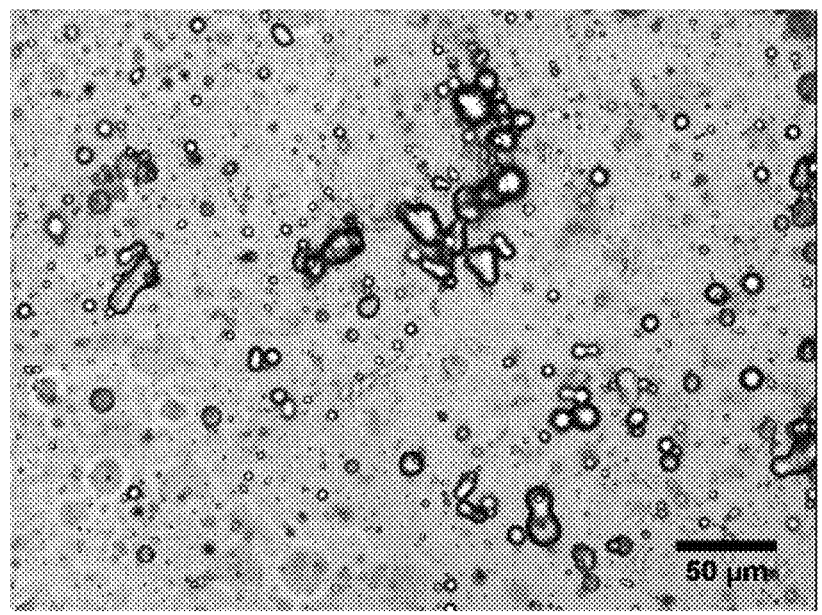
Figure 13:
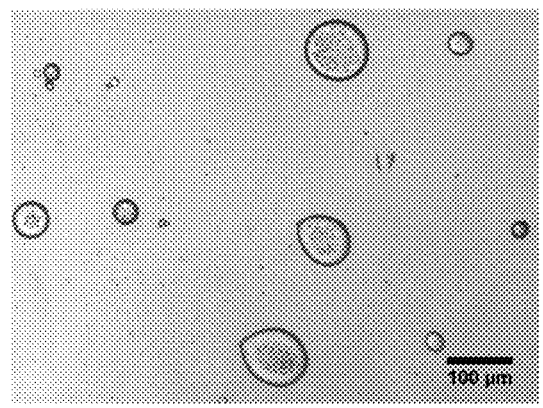
Figure 14:
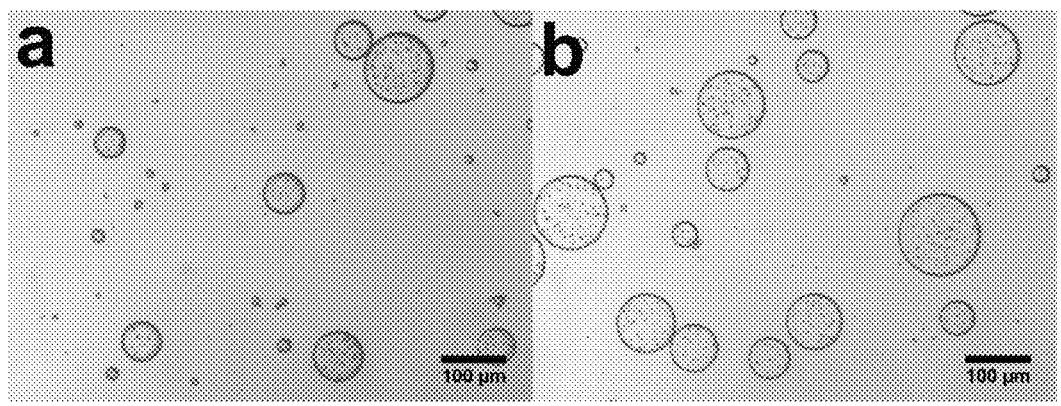
Figure 15:
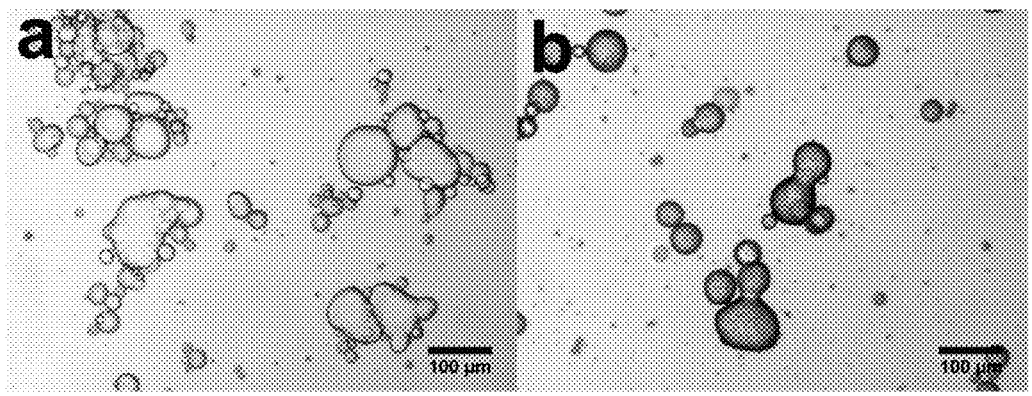
Figure 16:
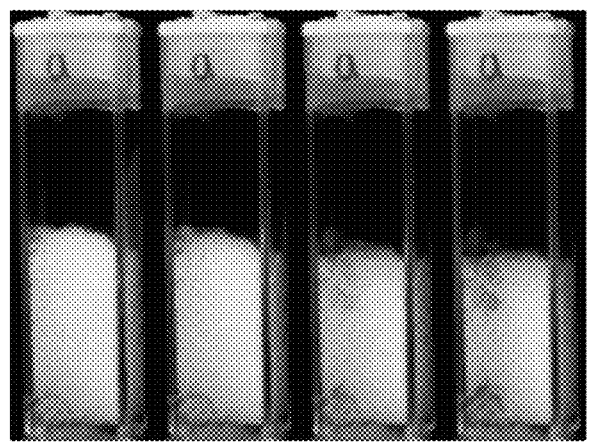
Figure 17:
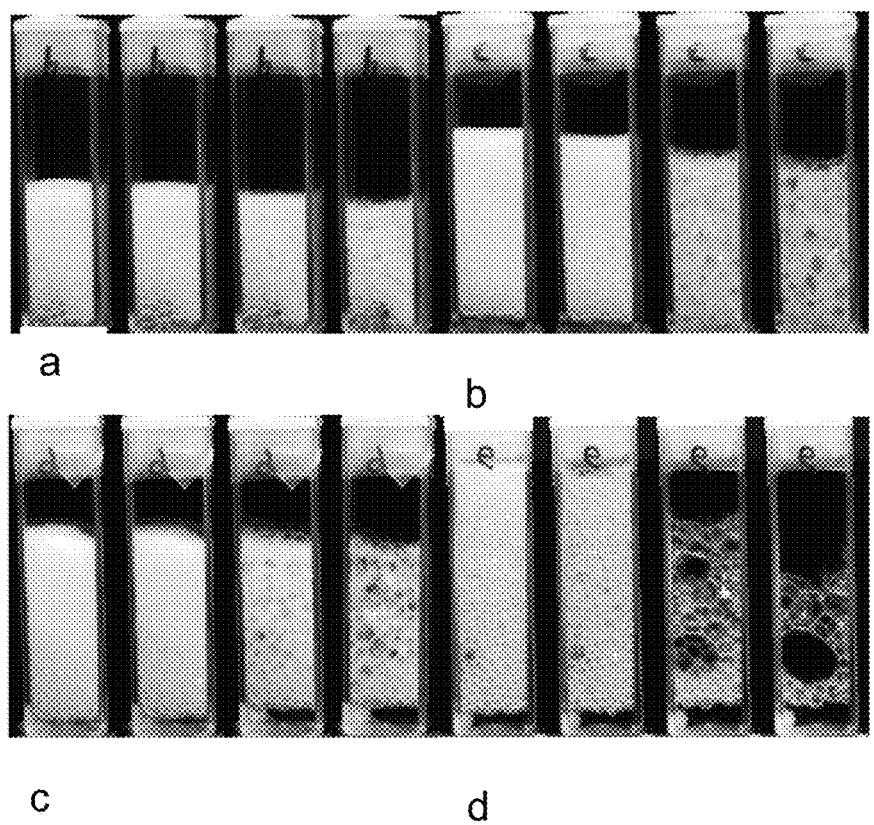
Figure 18:
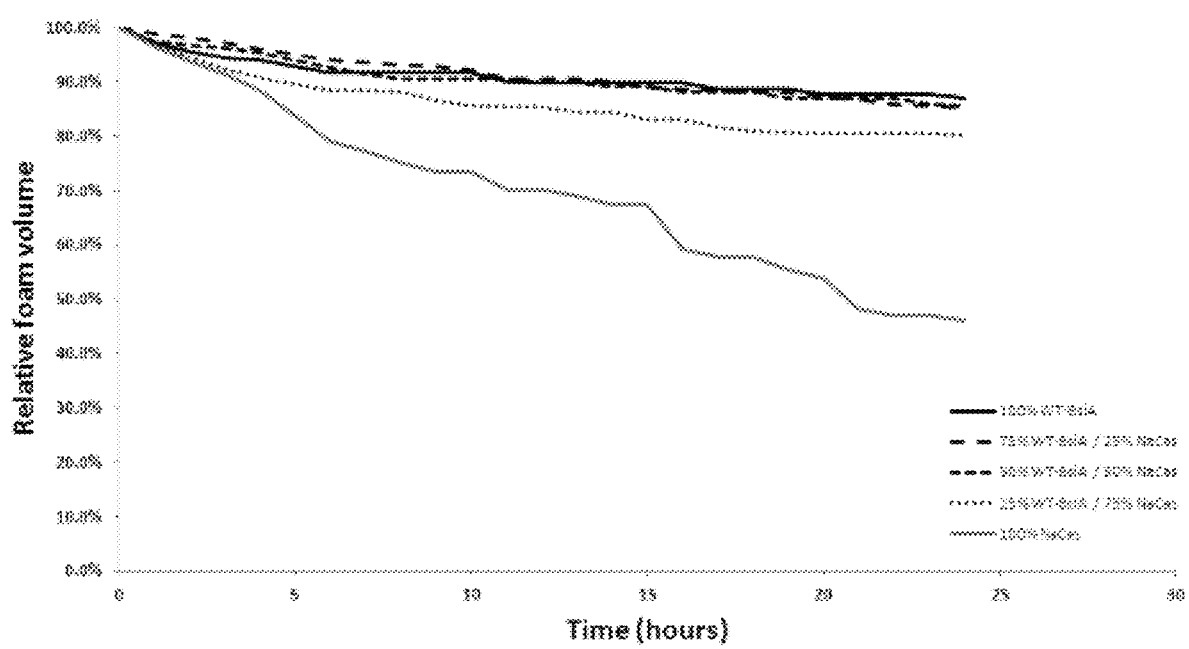
Figure 19:
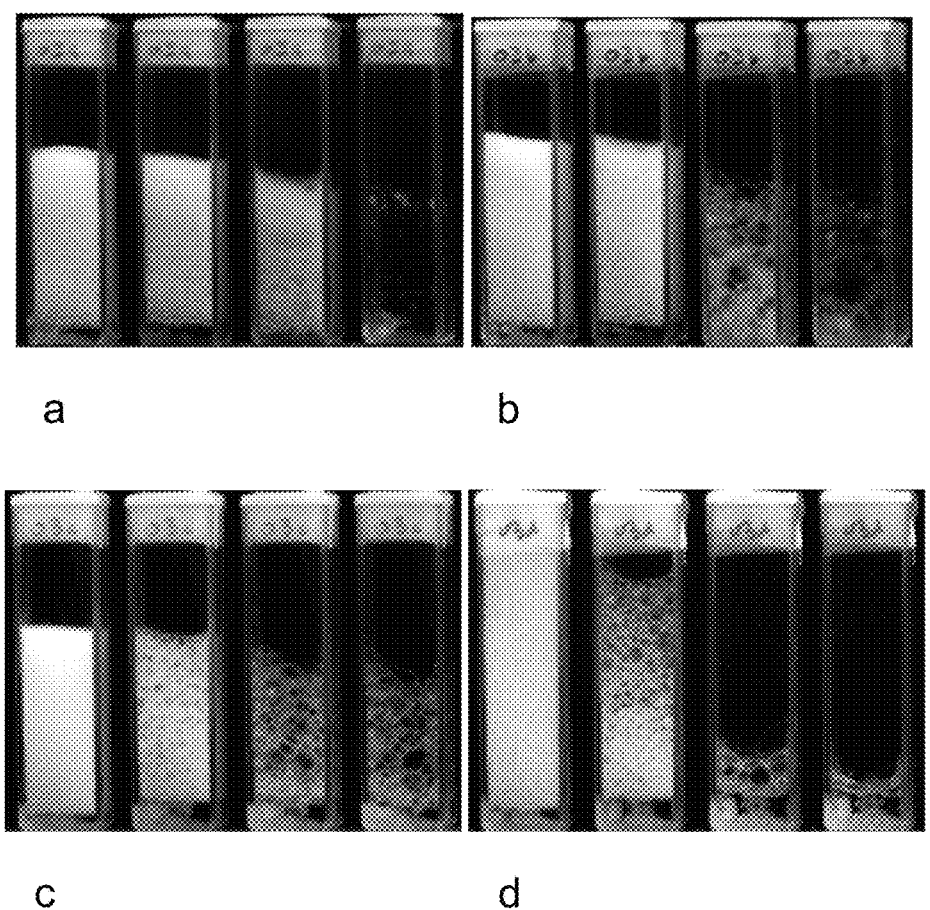
Figure 20:
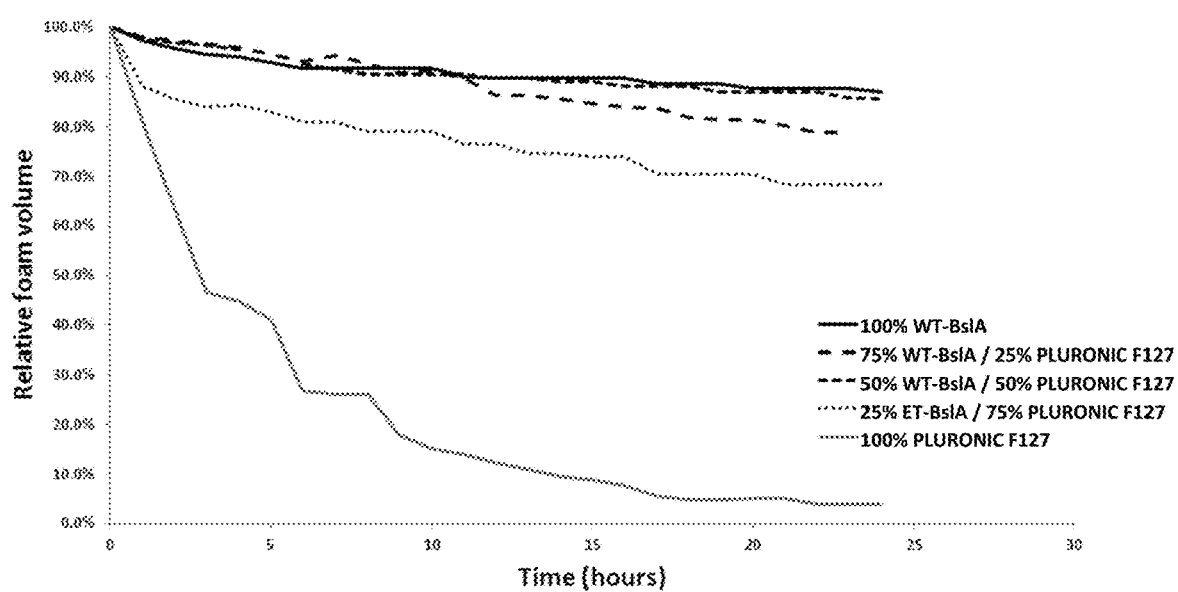
Figure 21:
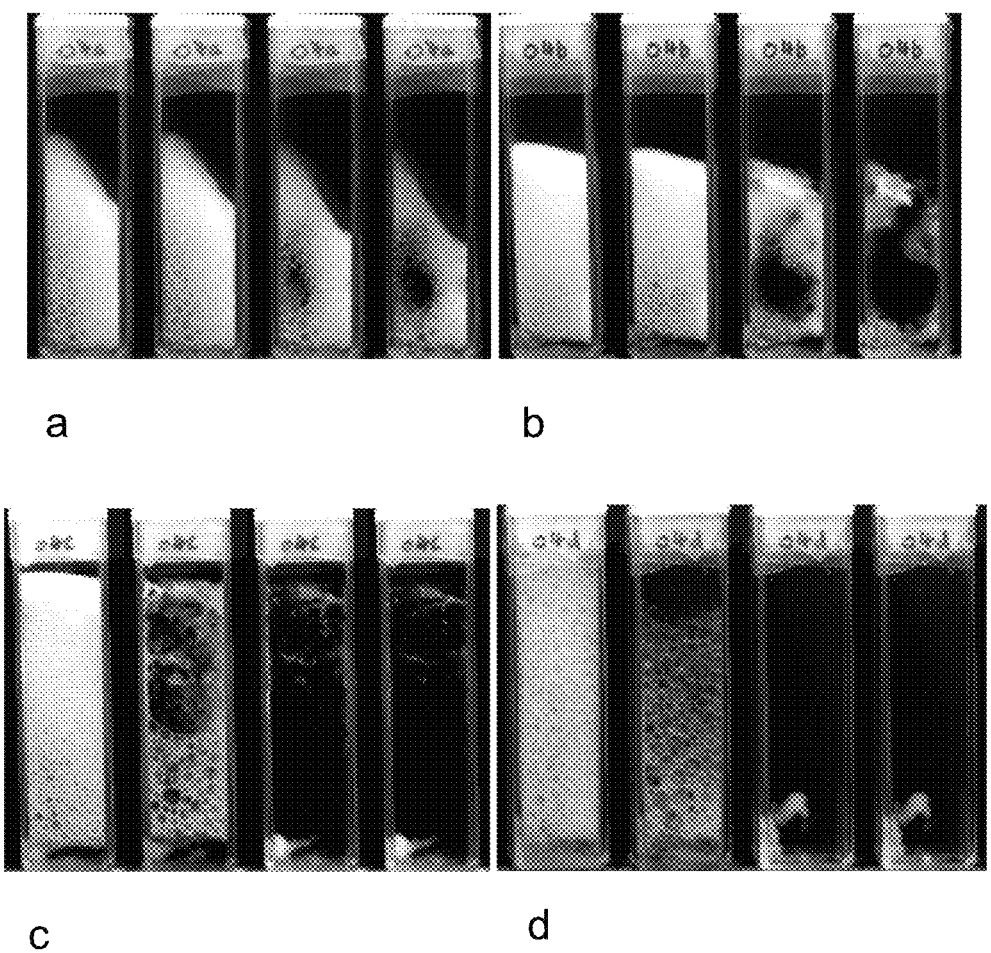
Figure 22:
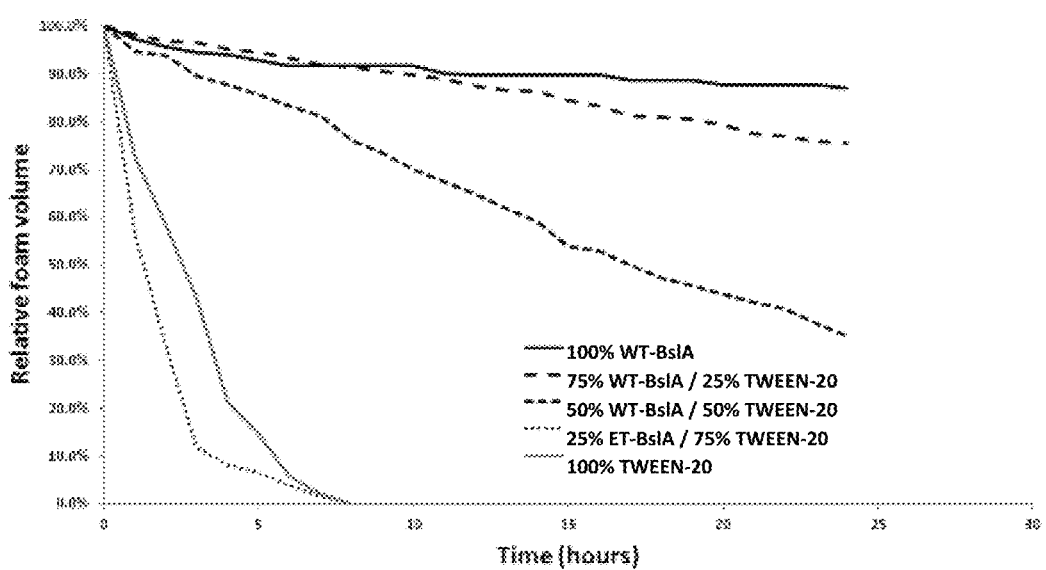
Figure 23:
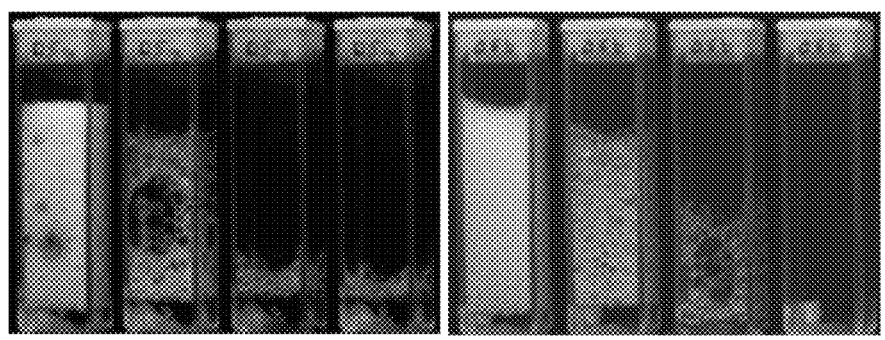
Figure 23:
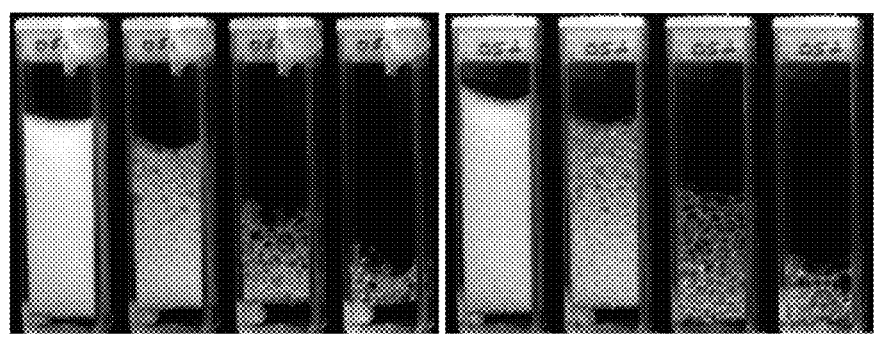
Figure 24:
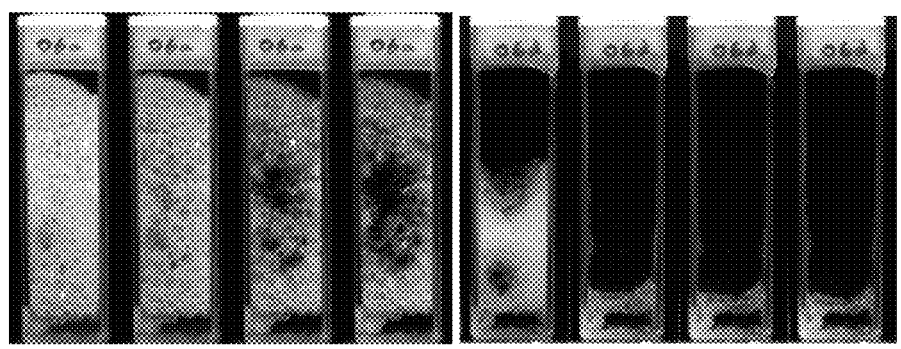
Figure 25:
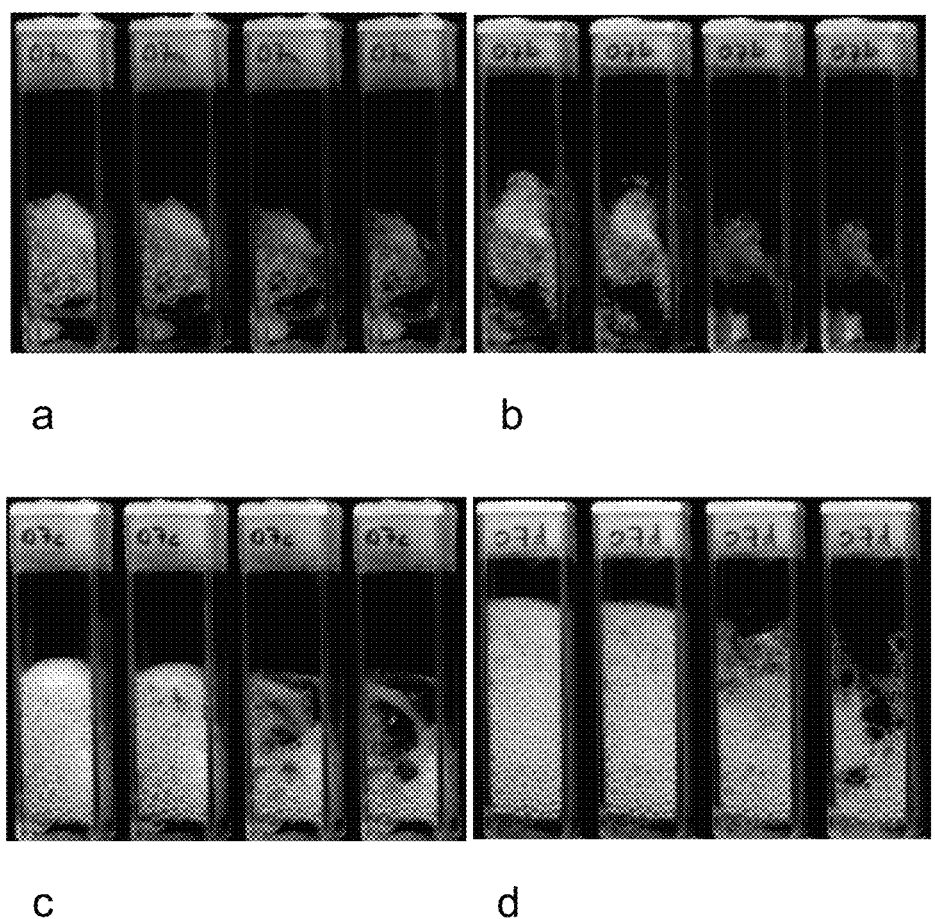
Figure 26:
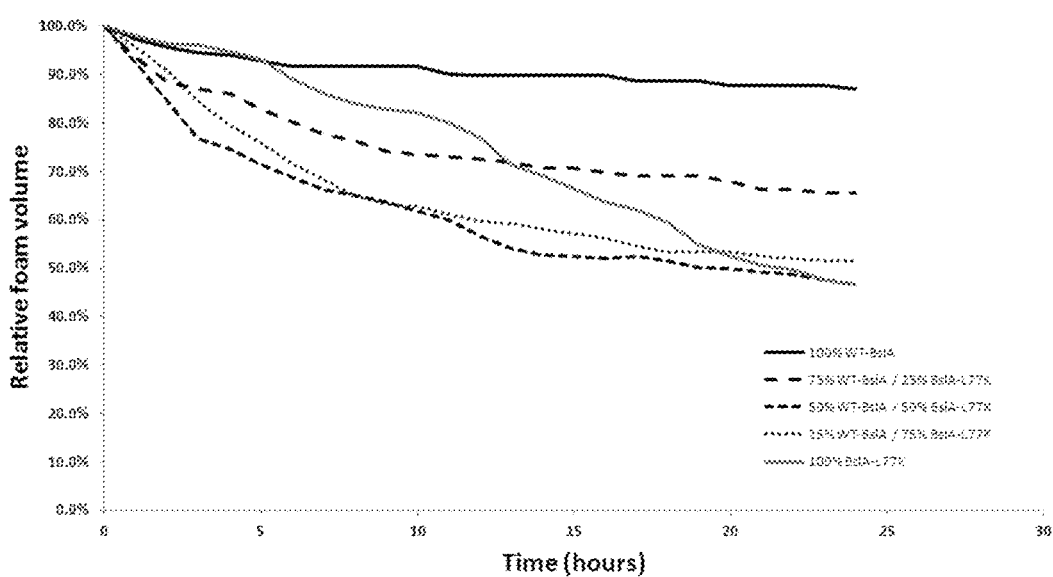
Figure 27:
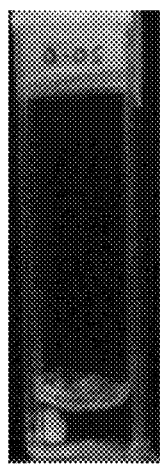
Figure 27:
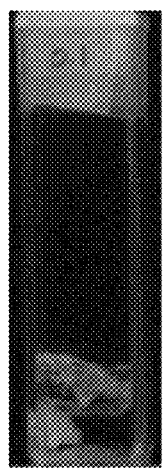
Figure 27:
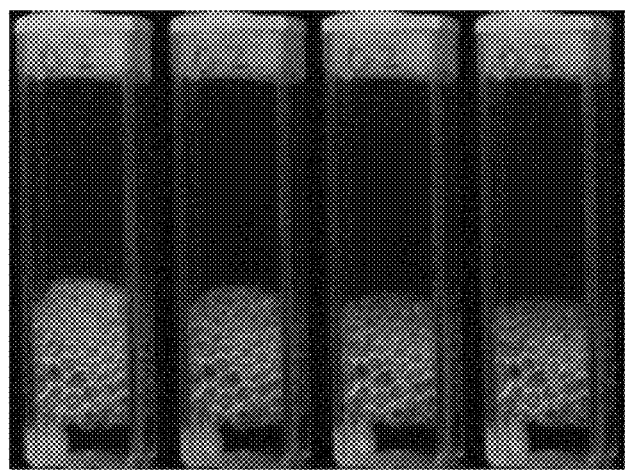
Figure 27:
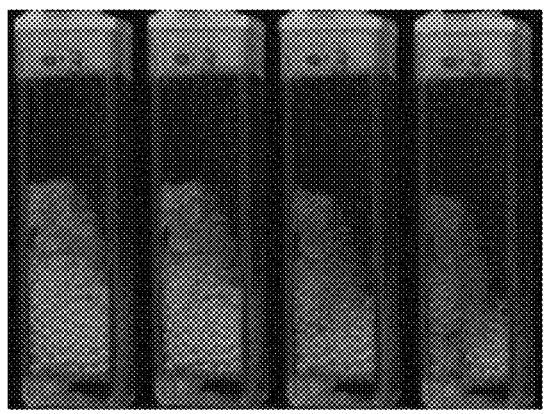
Figure 27:
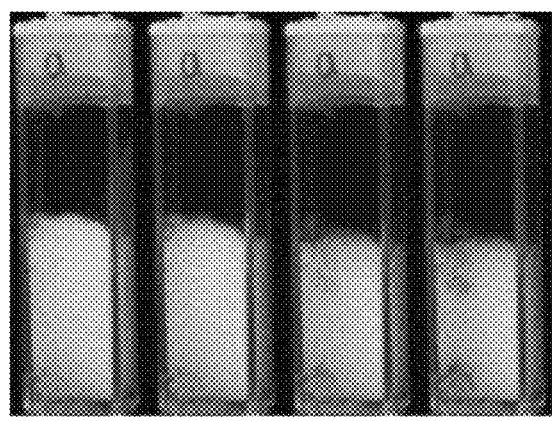
Figure 27:
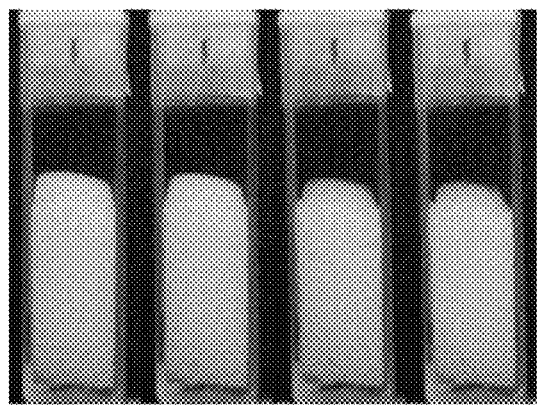
Figure 27:
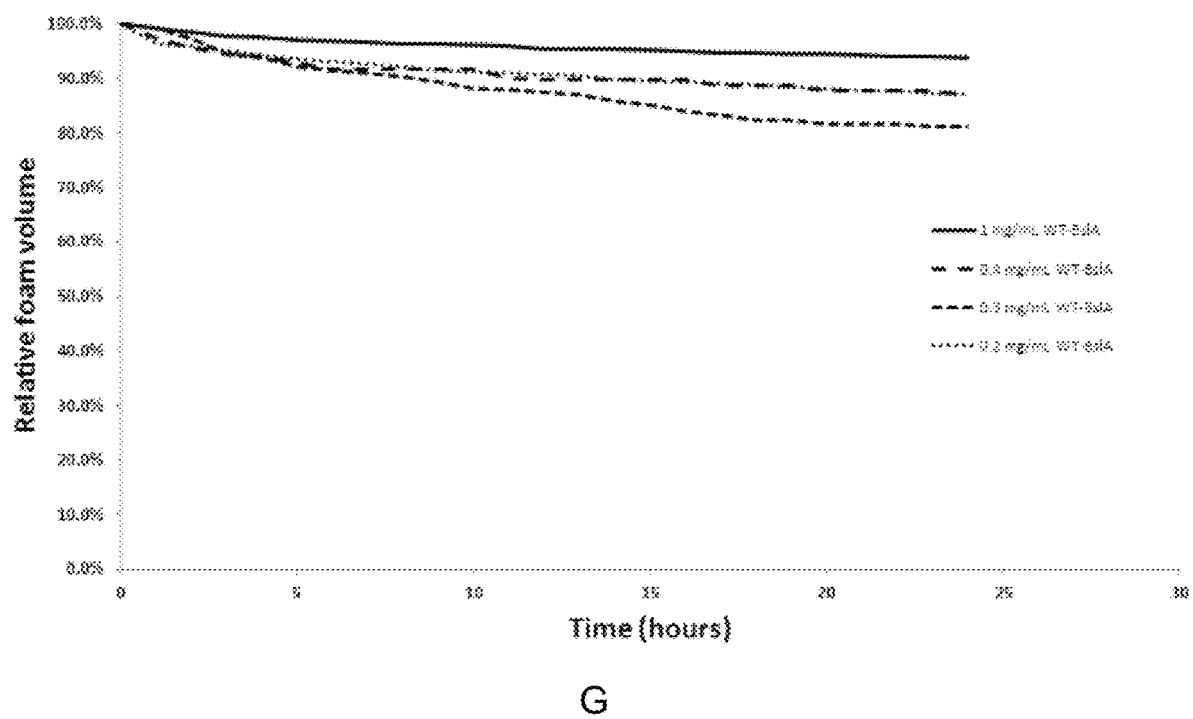
Figure 28:
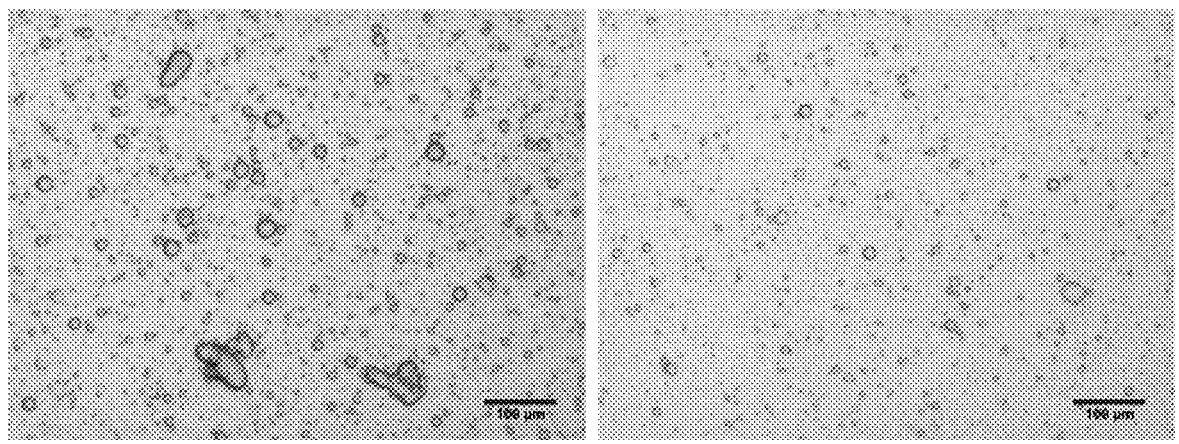
Figure 29:
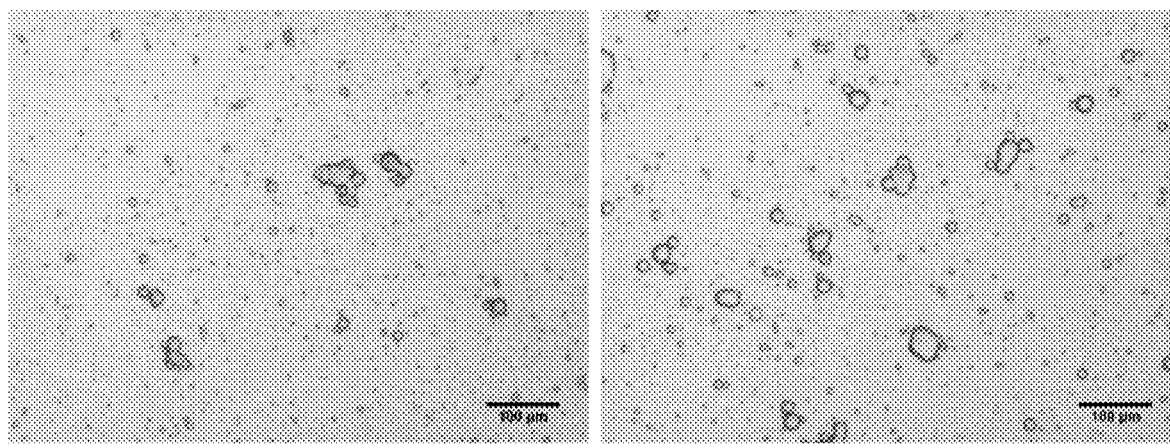
Figure 30:
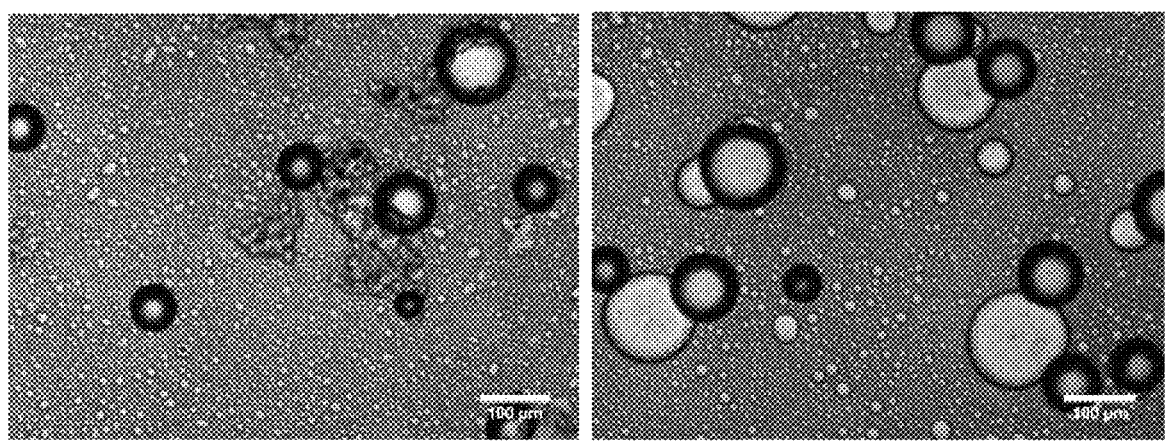
Figure 31:
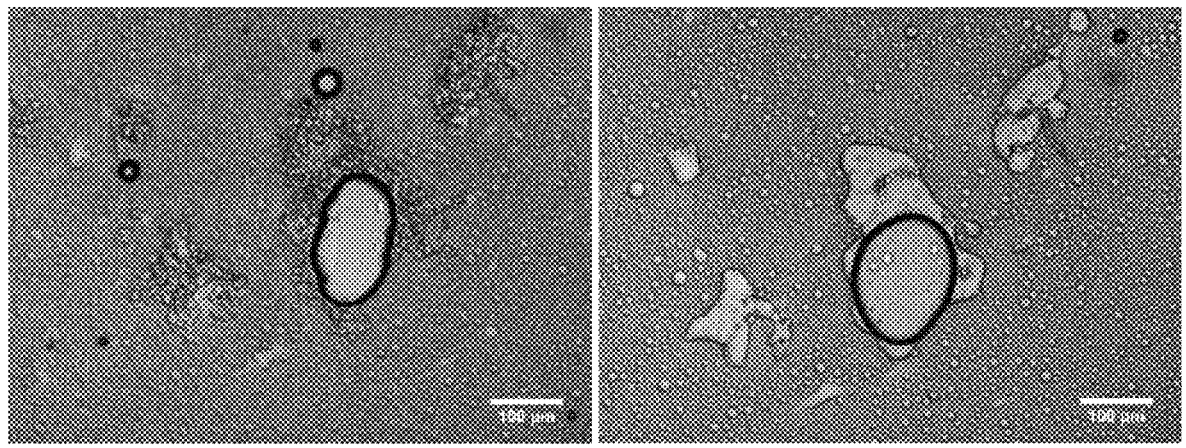
Figure 32:
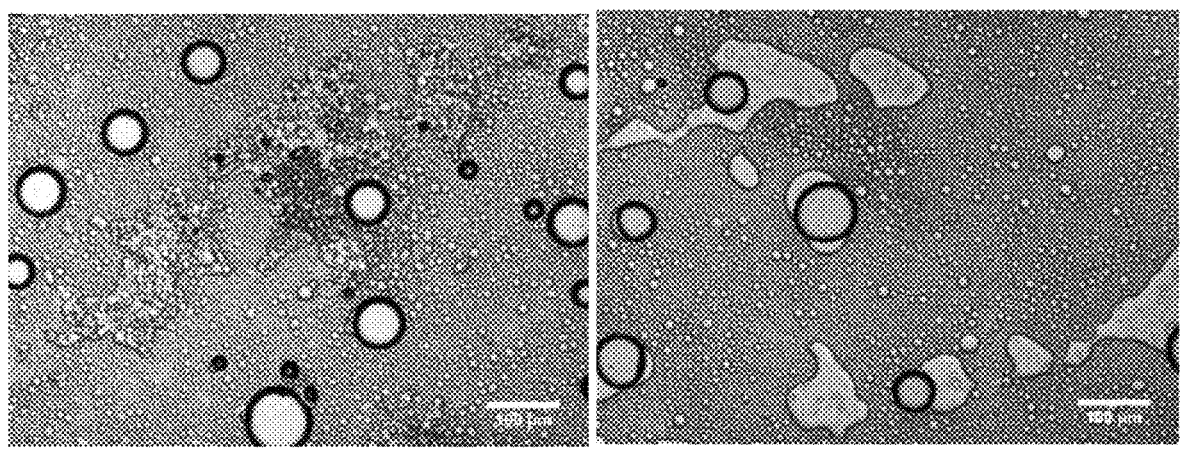
Figure 33:
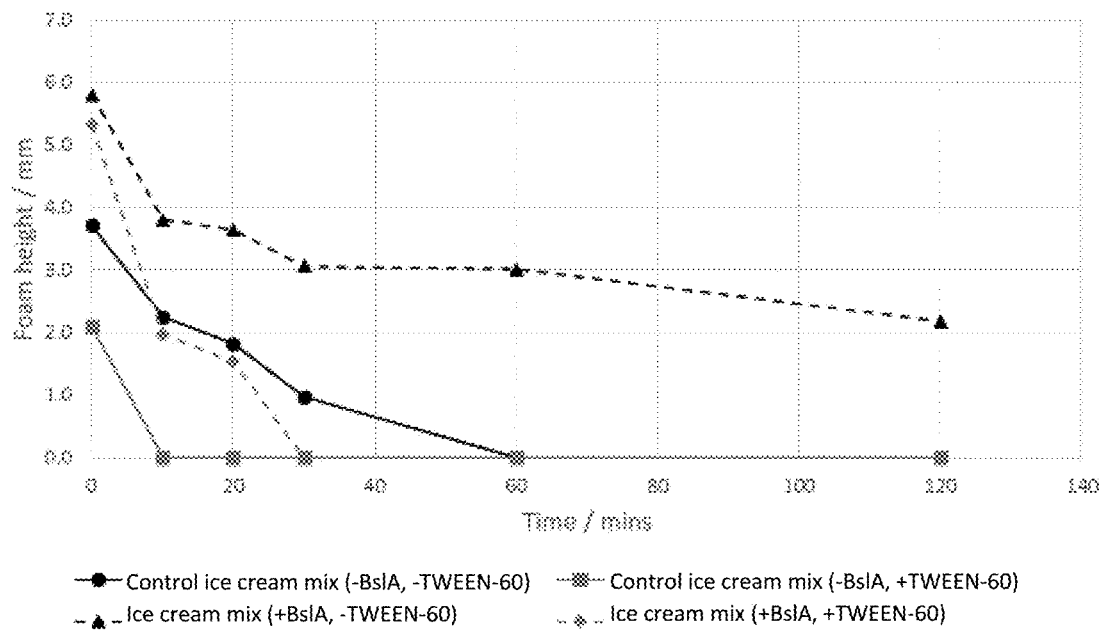
Figure 34:
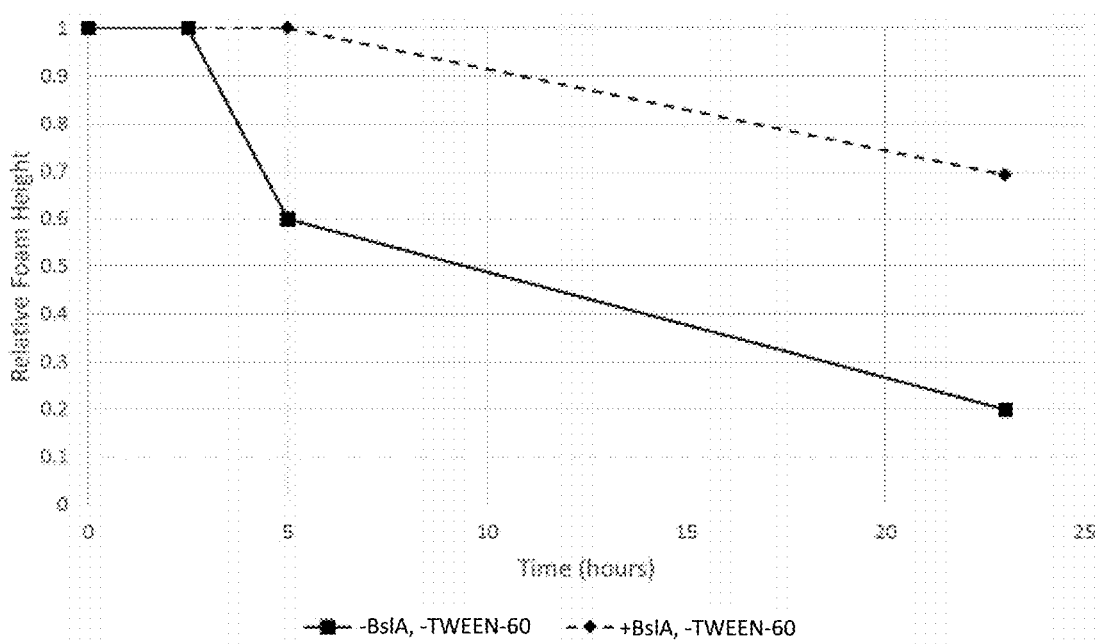
Figure 35:
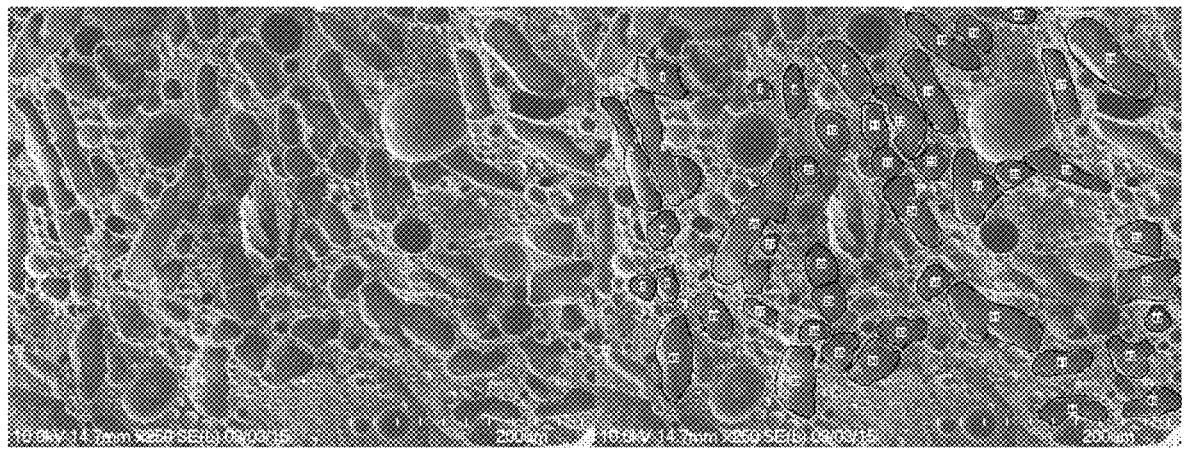
Figure 36:
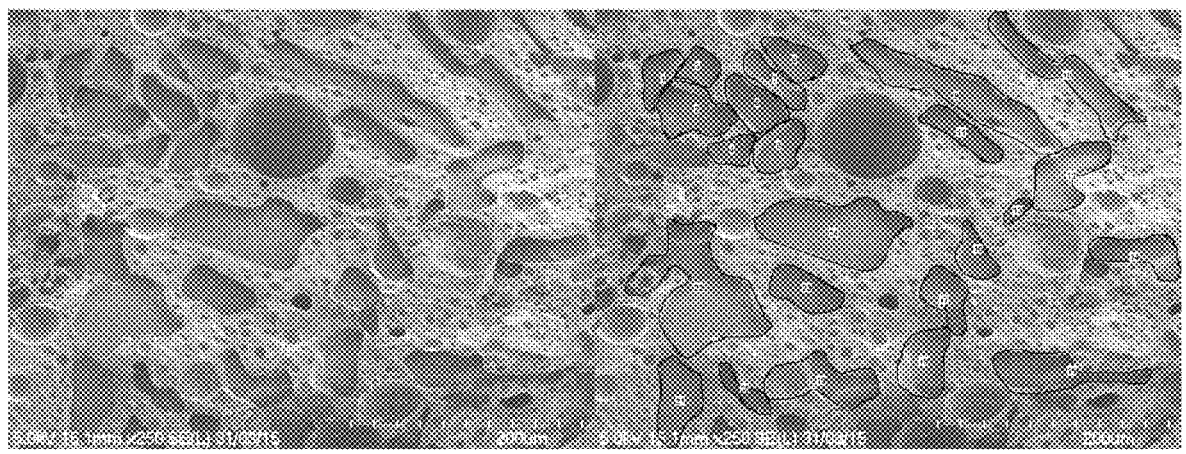
Figure 37:
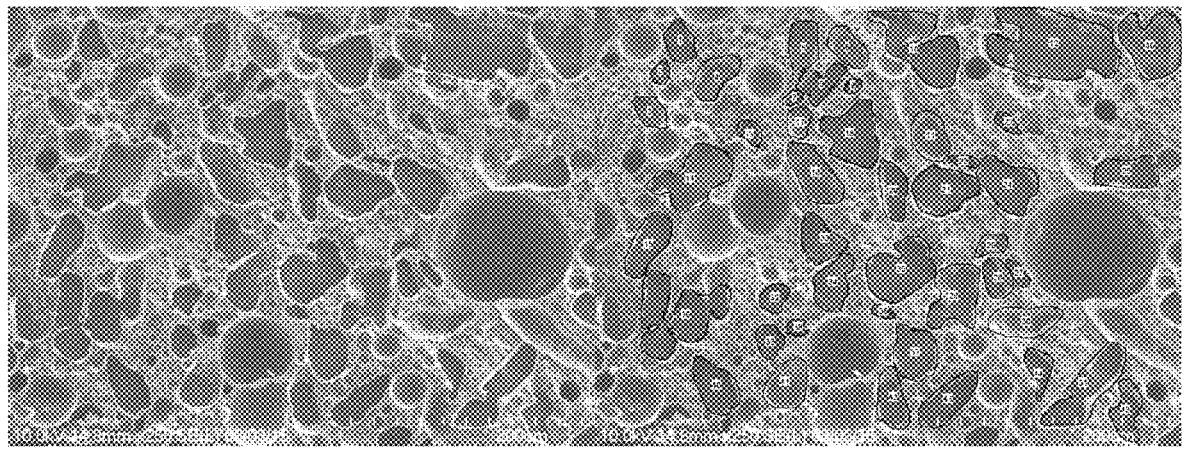
Figure 38:
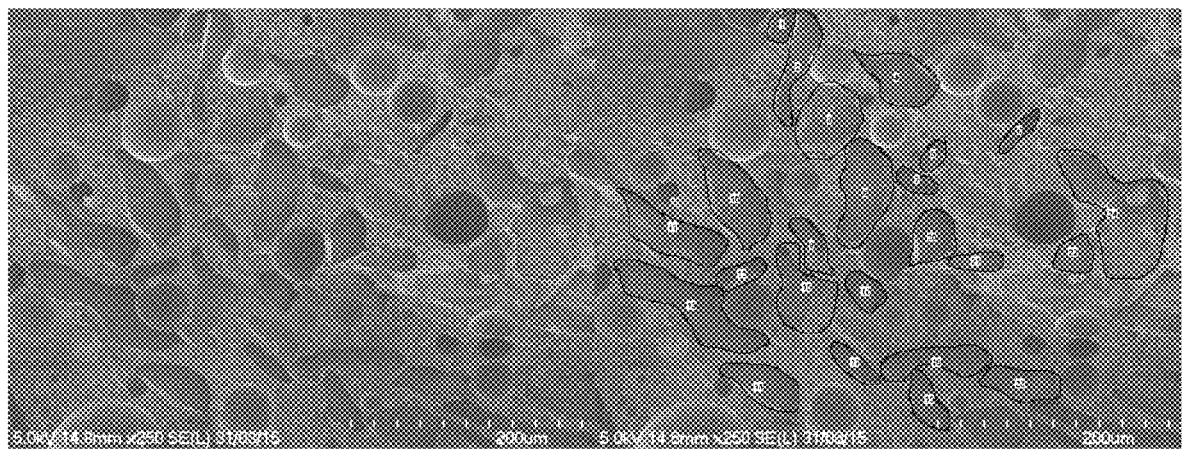
Figure 39:
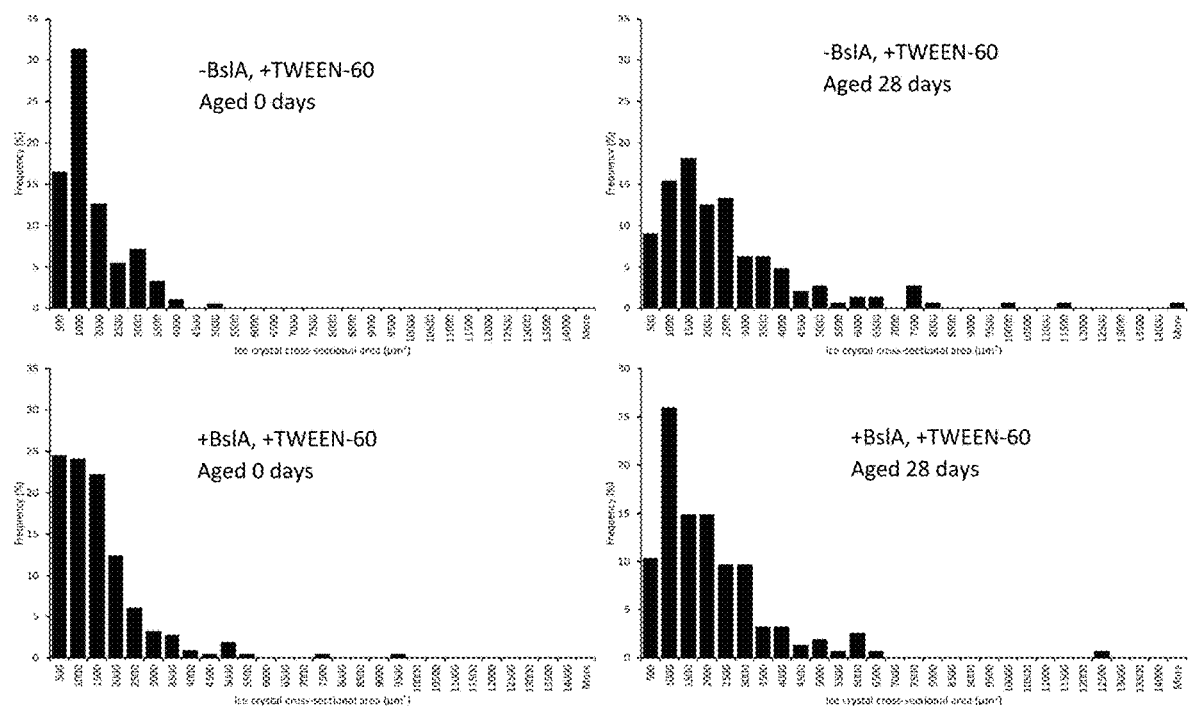
Figure 40:
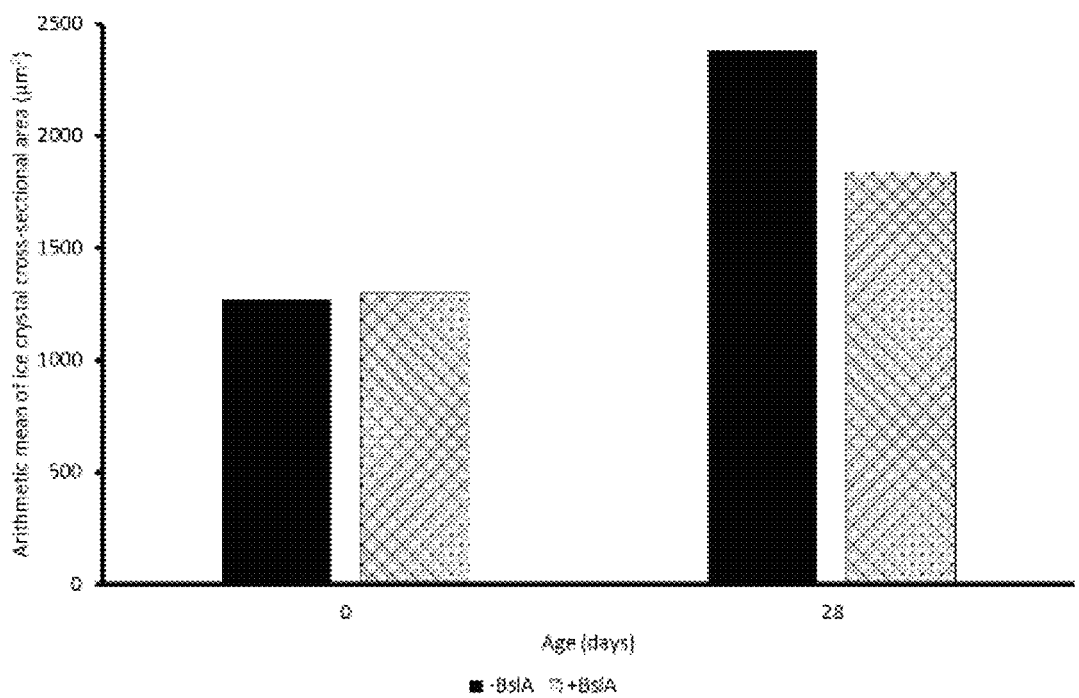
Figure 40:
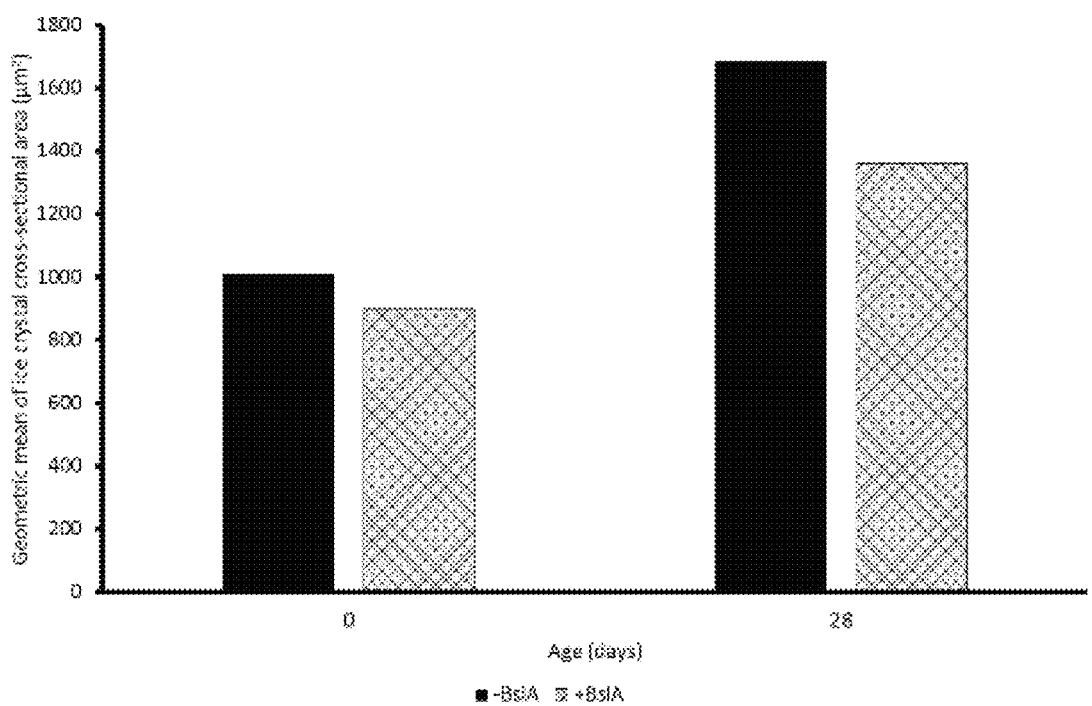
Figure 41:
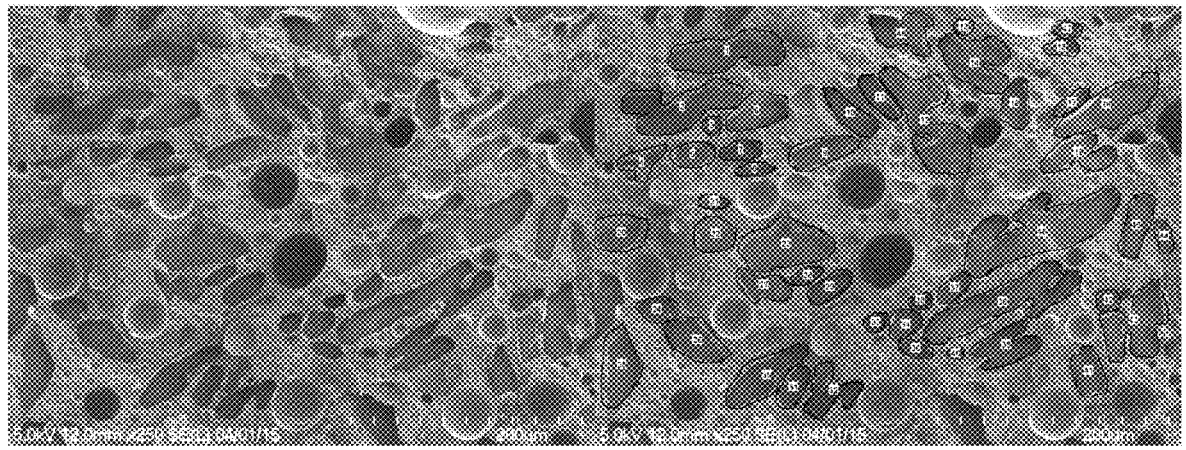
Figure 42:
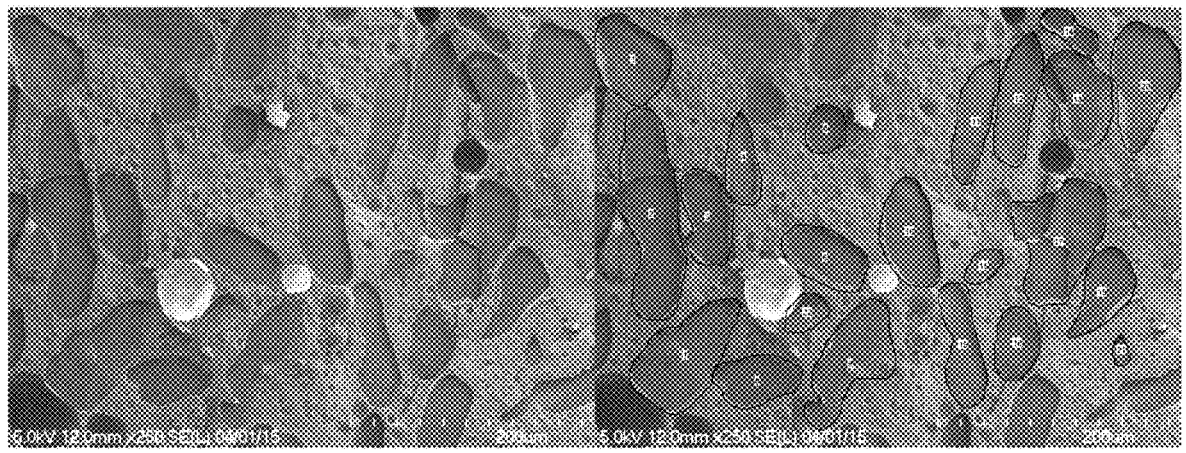
Figure 43:
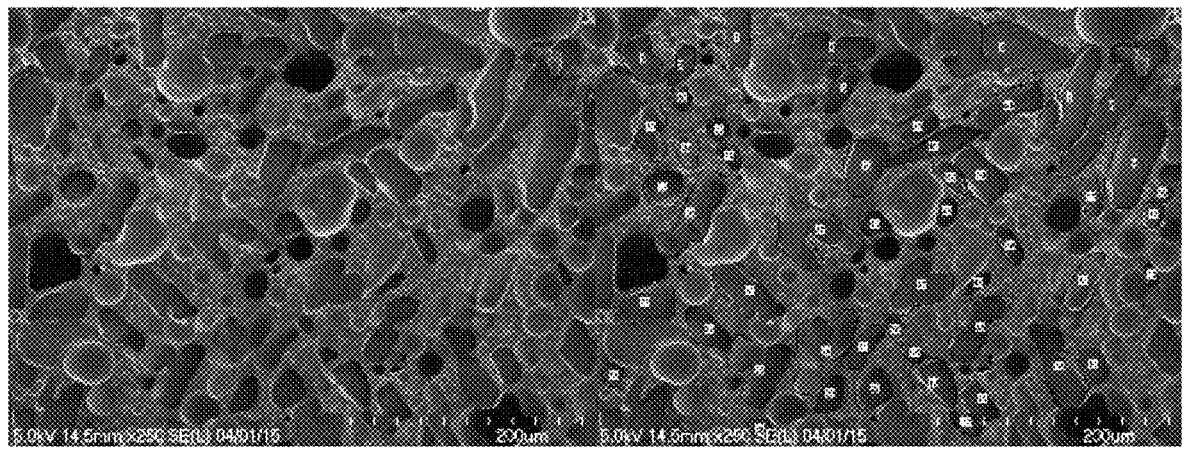
Figure 44:
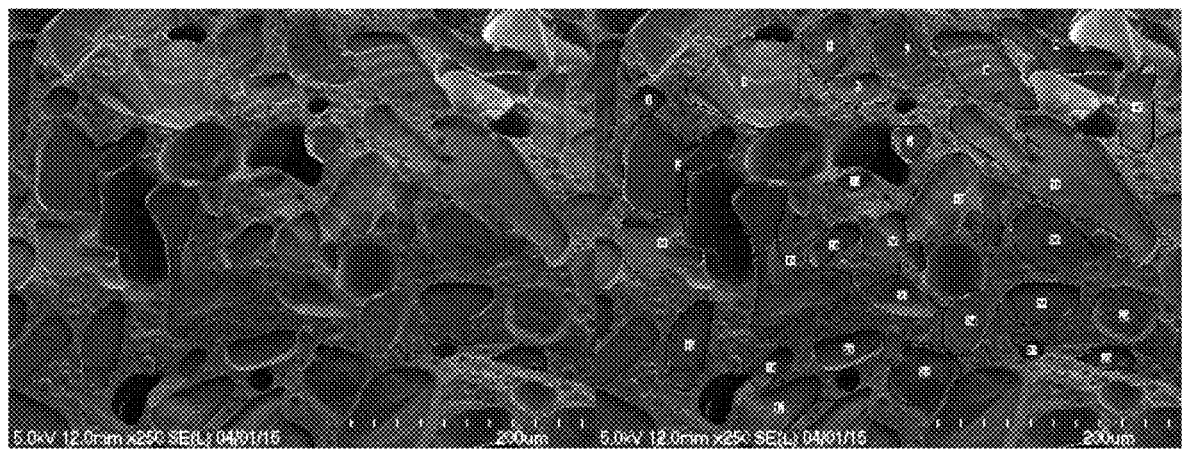
Figure 45:
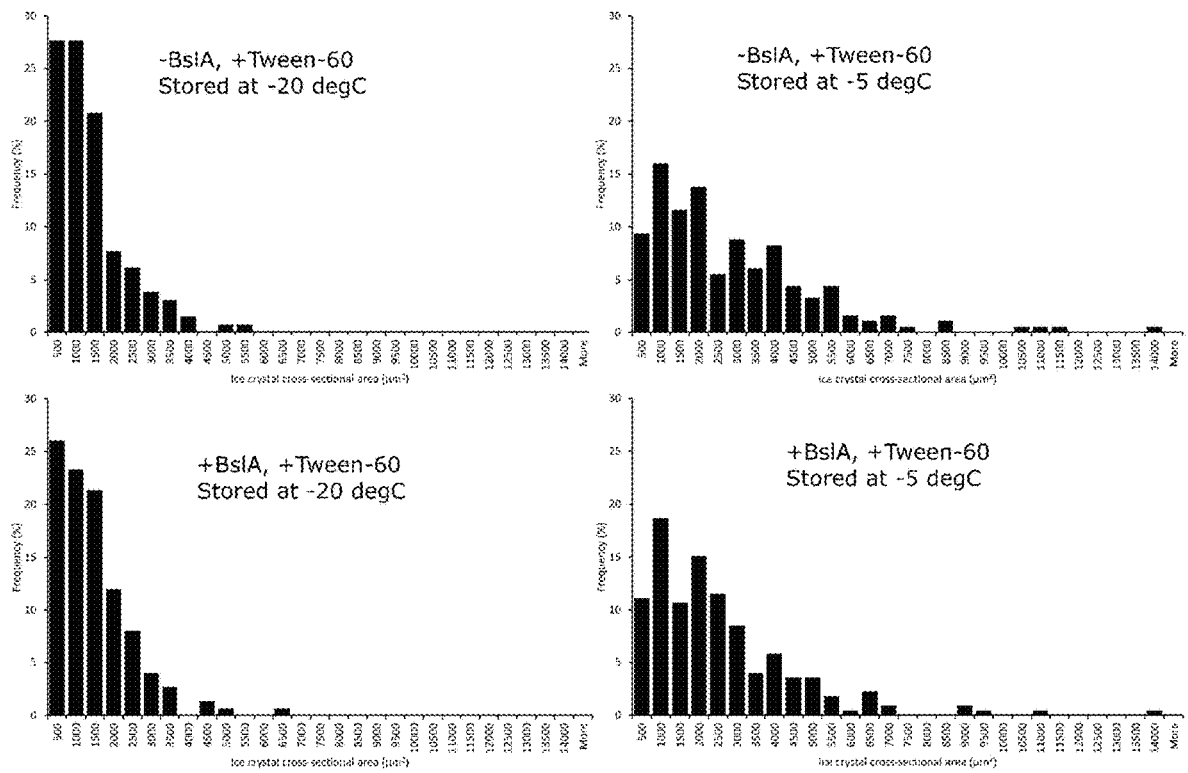
Figure 46:
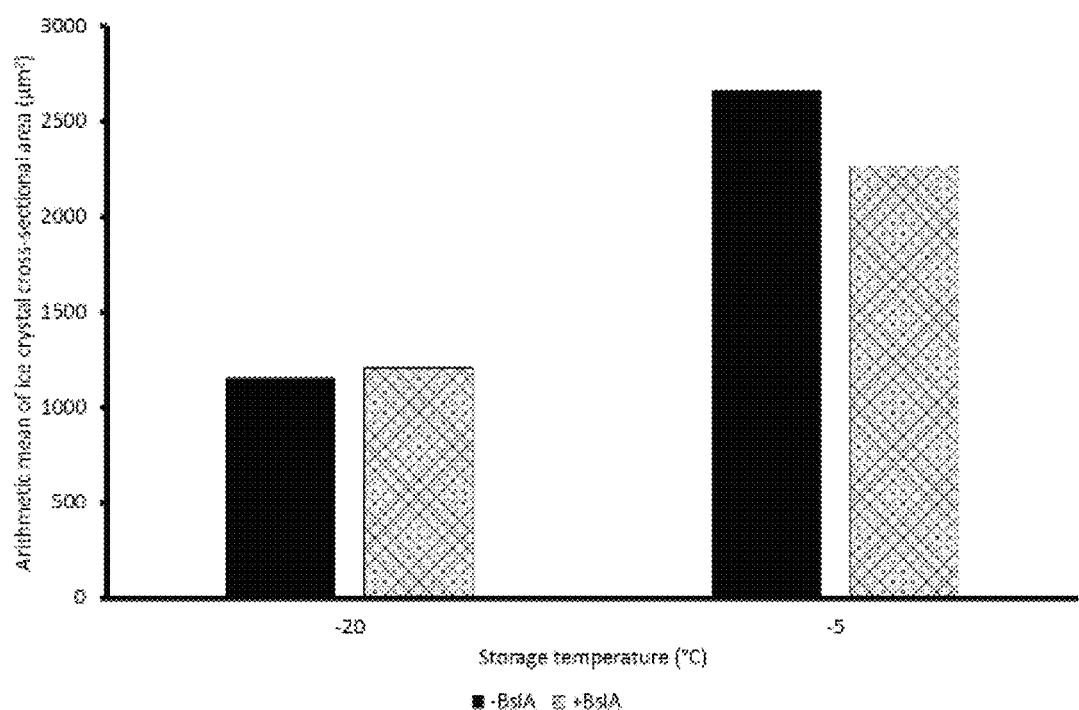
Figure 46:
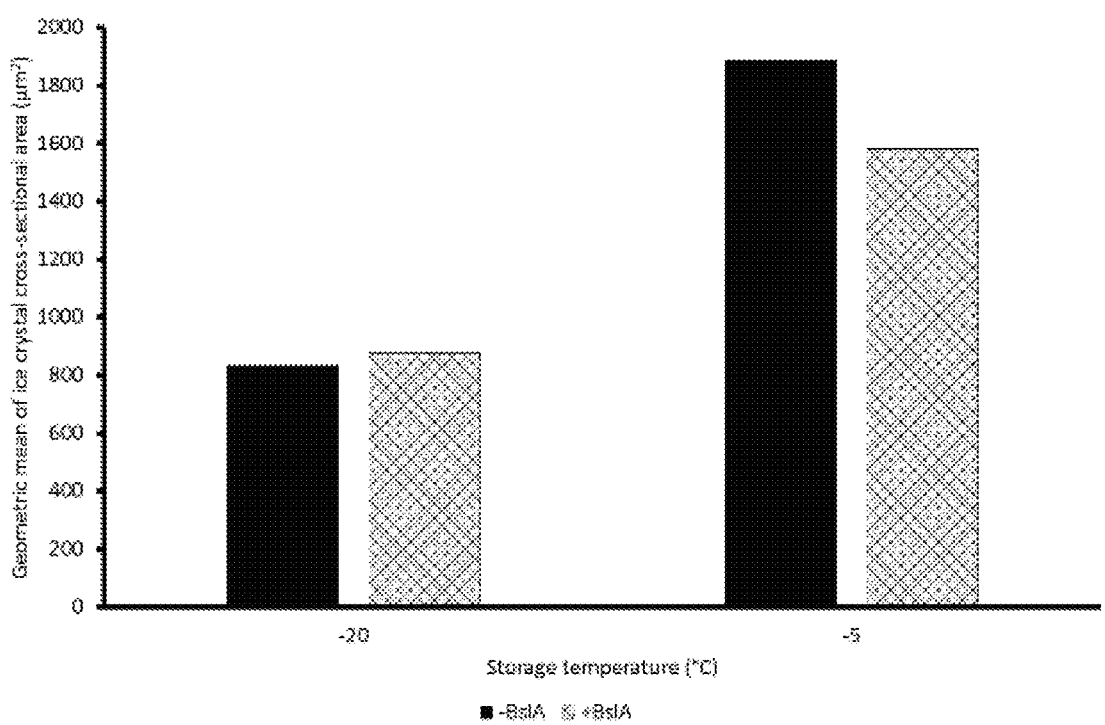
Figure 47:
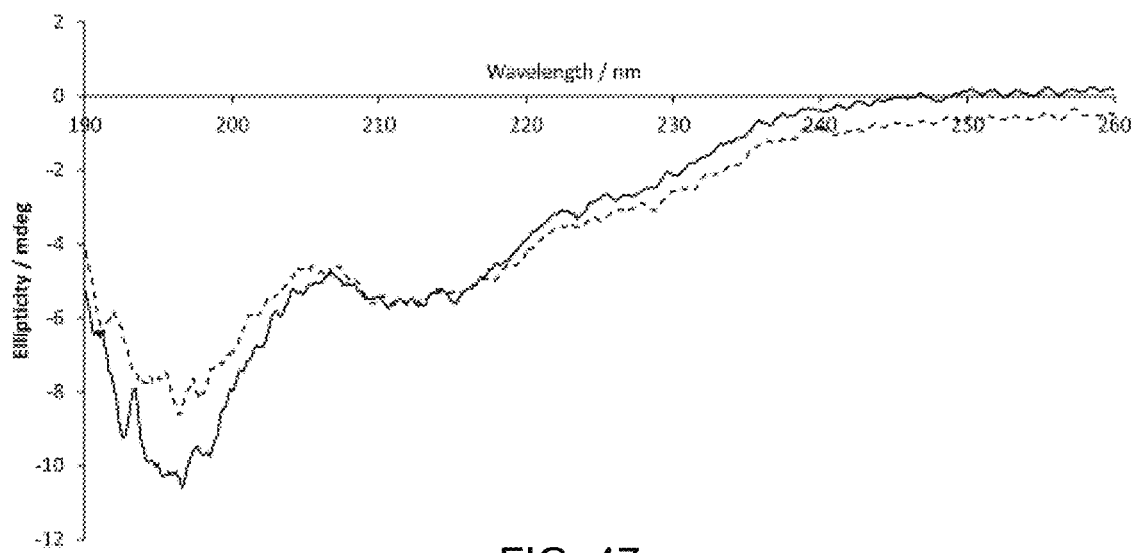
Figure 48:
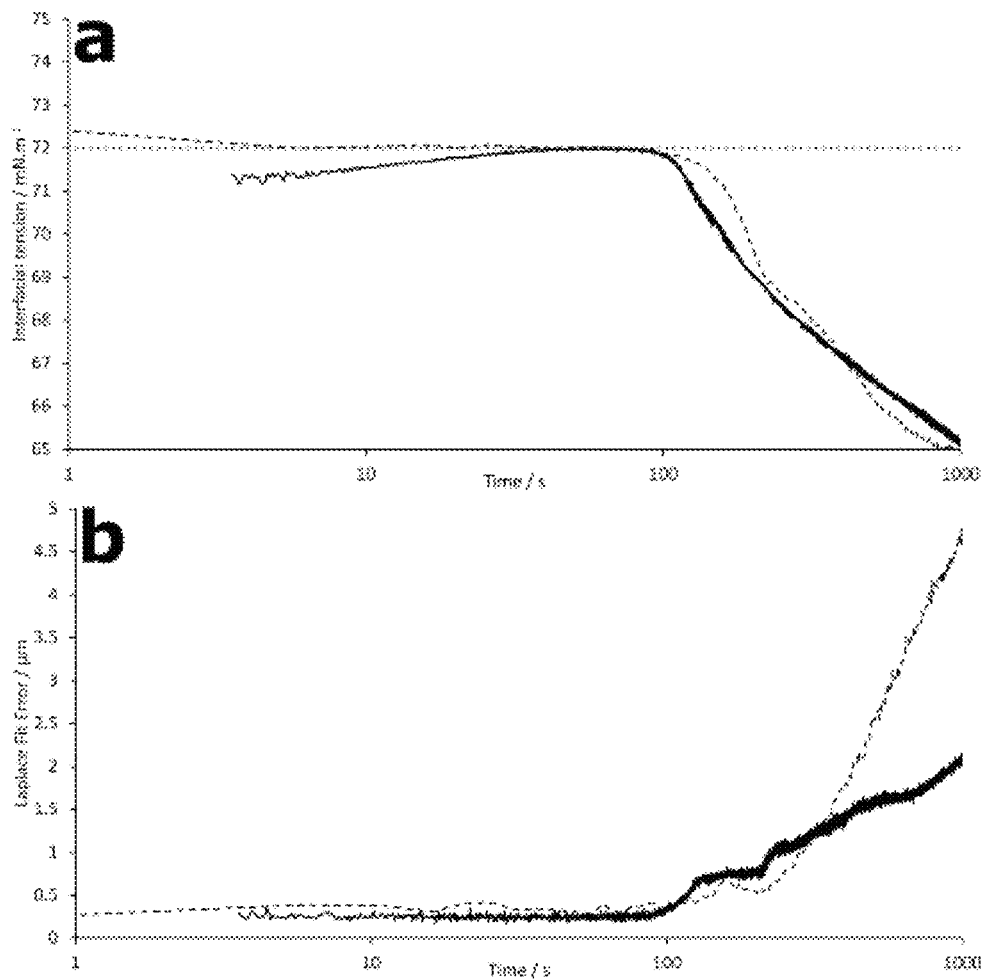
Figure 49:
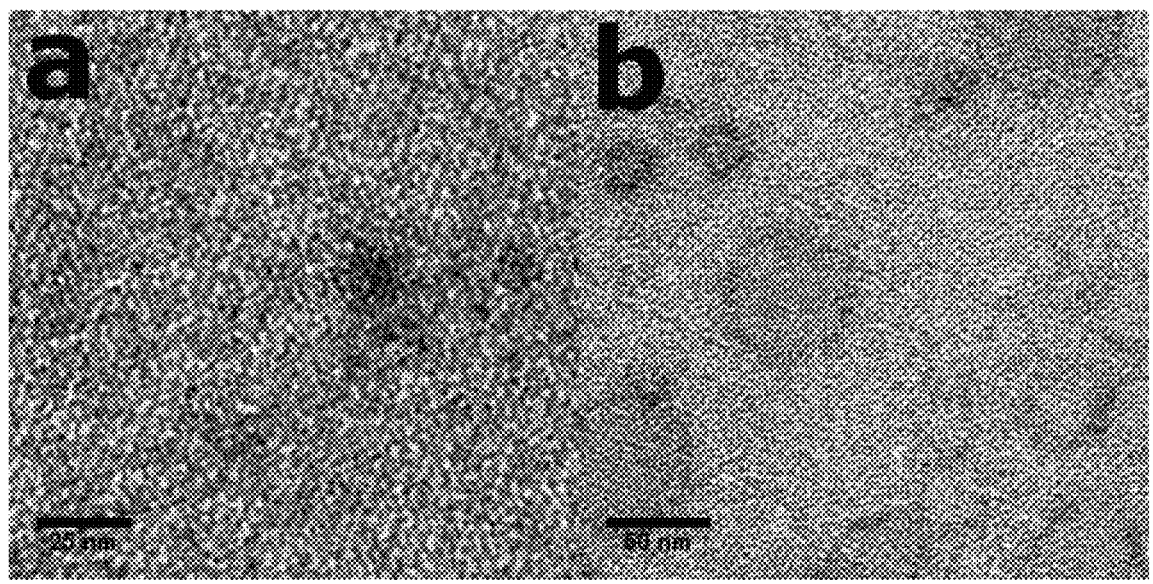
Figure 50:
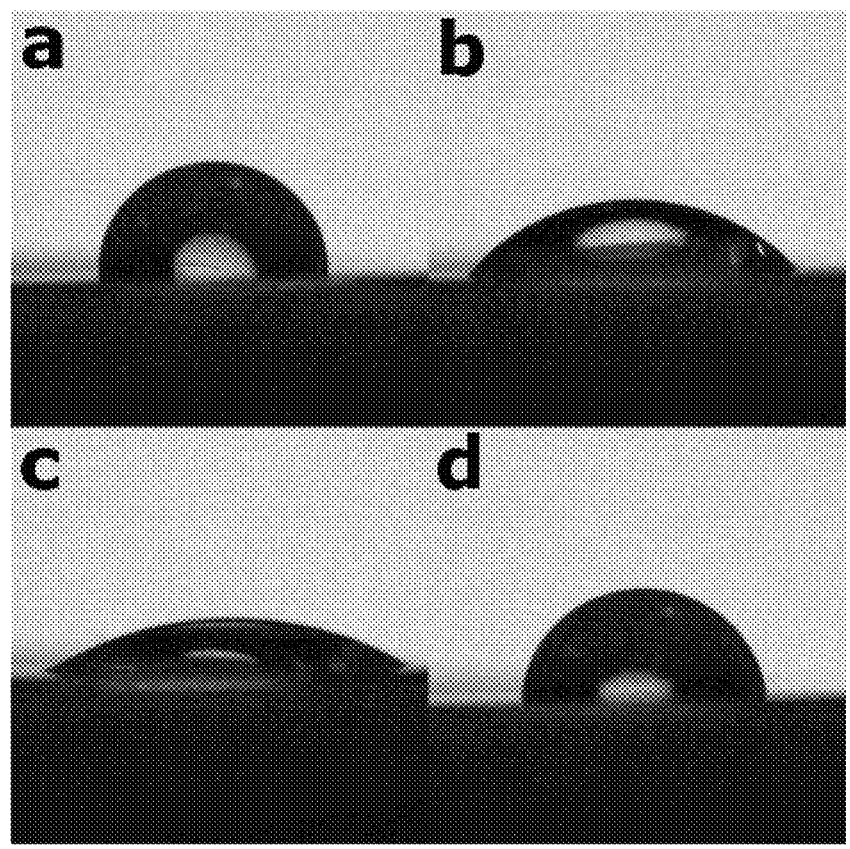
Figure 51:
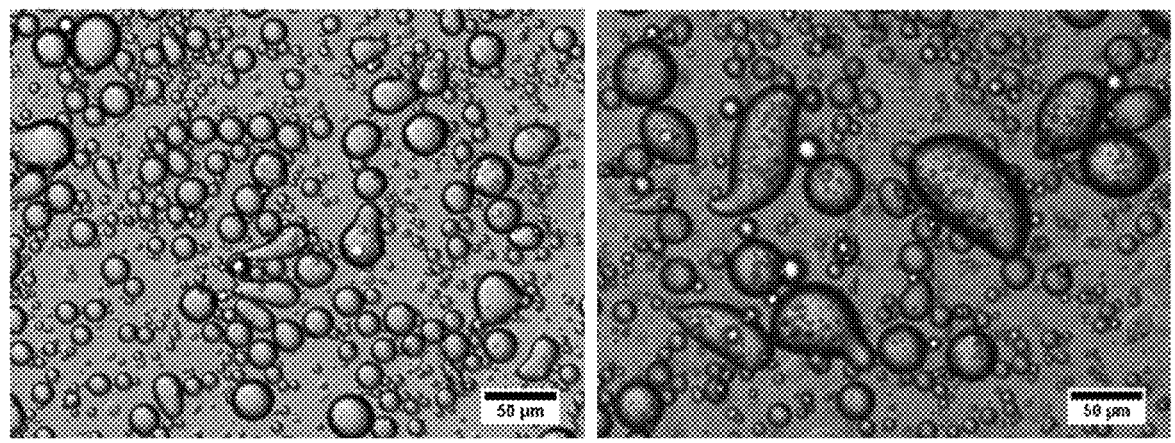
Figure 52:
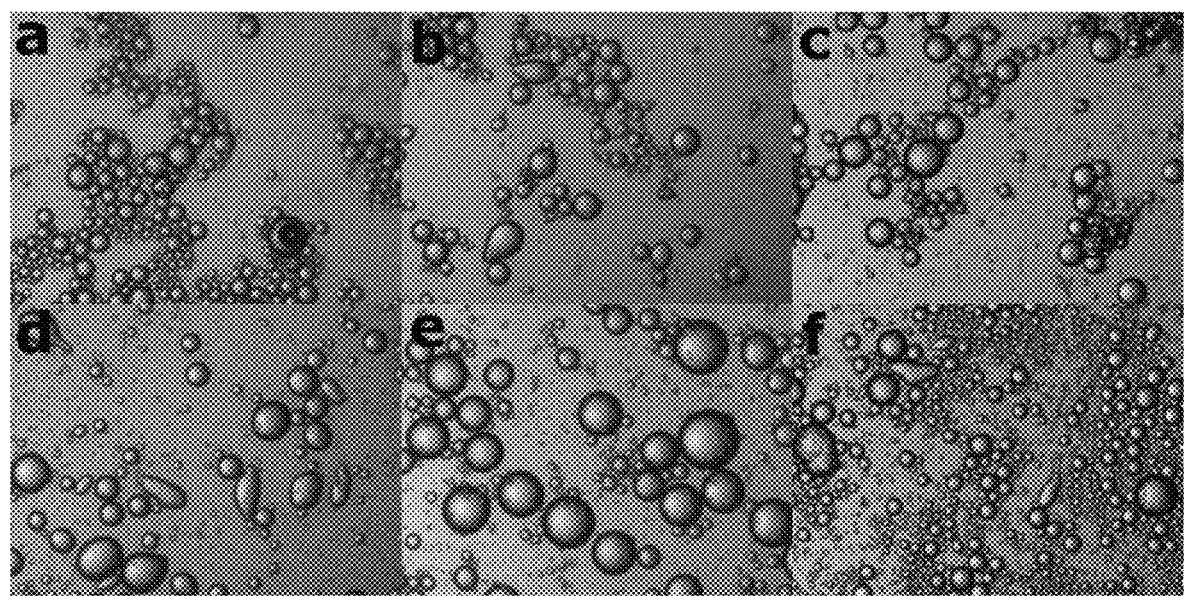
Figure 53:
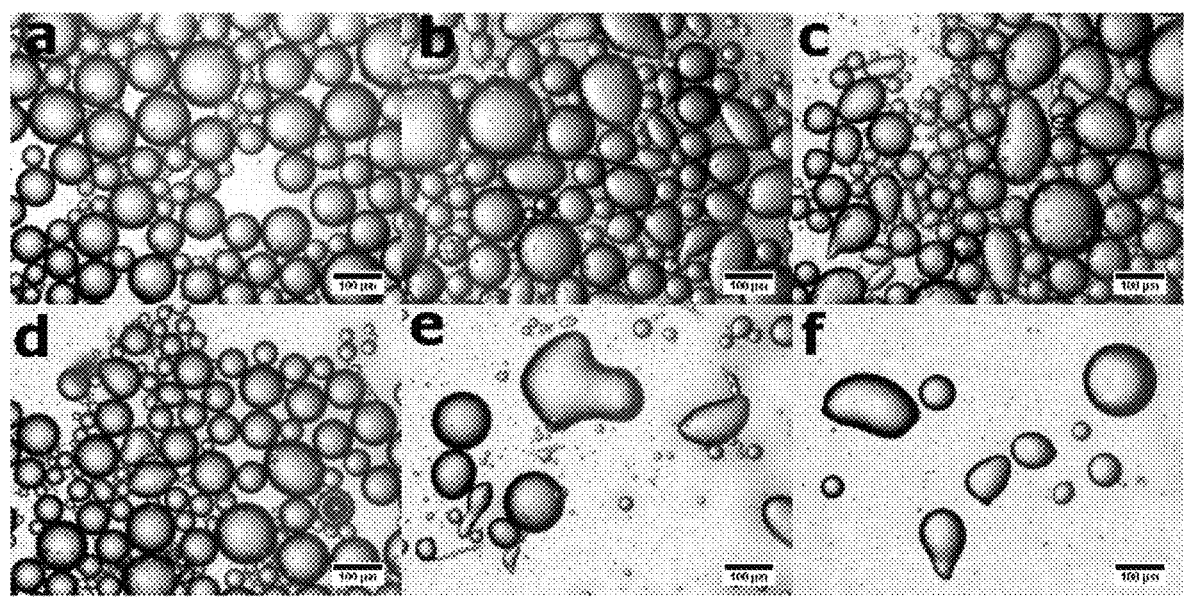
Figure 54:
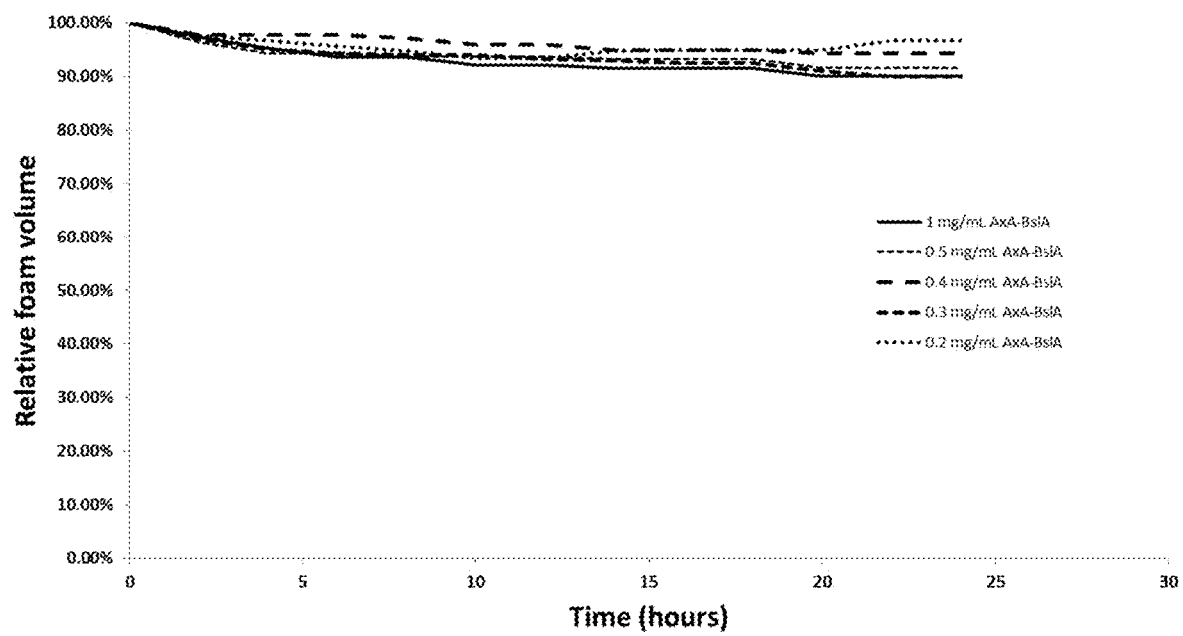
Figure 55:
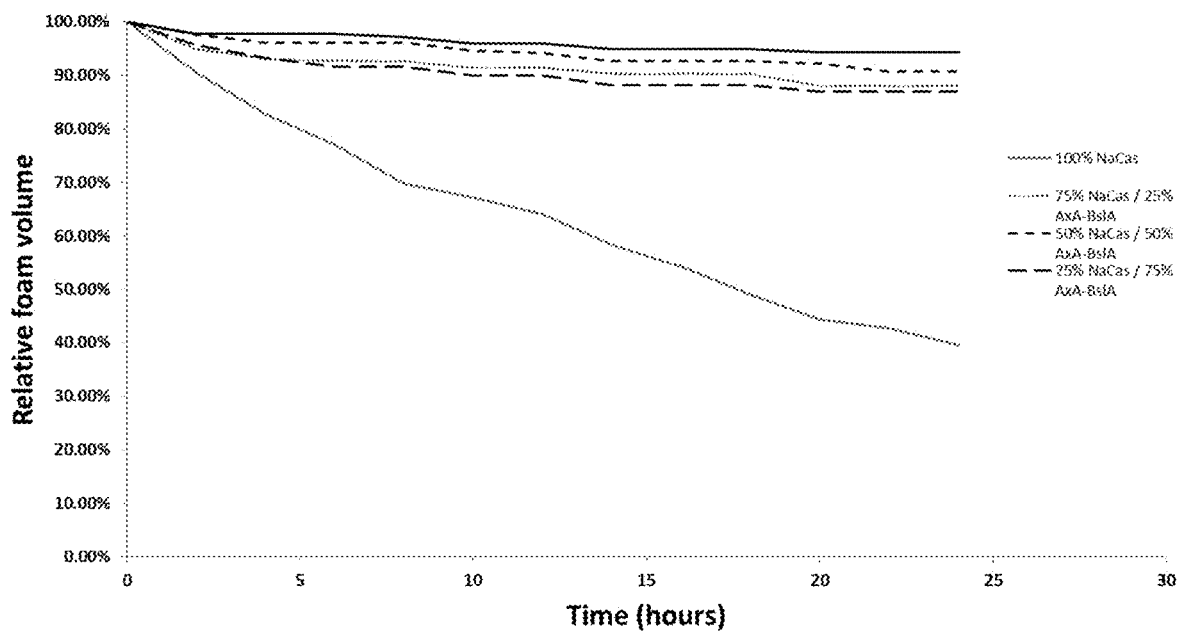
Figure 56:
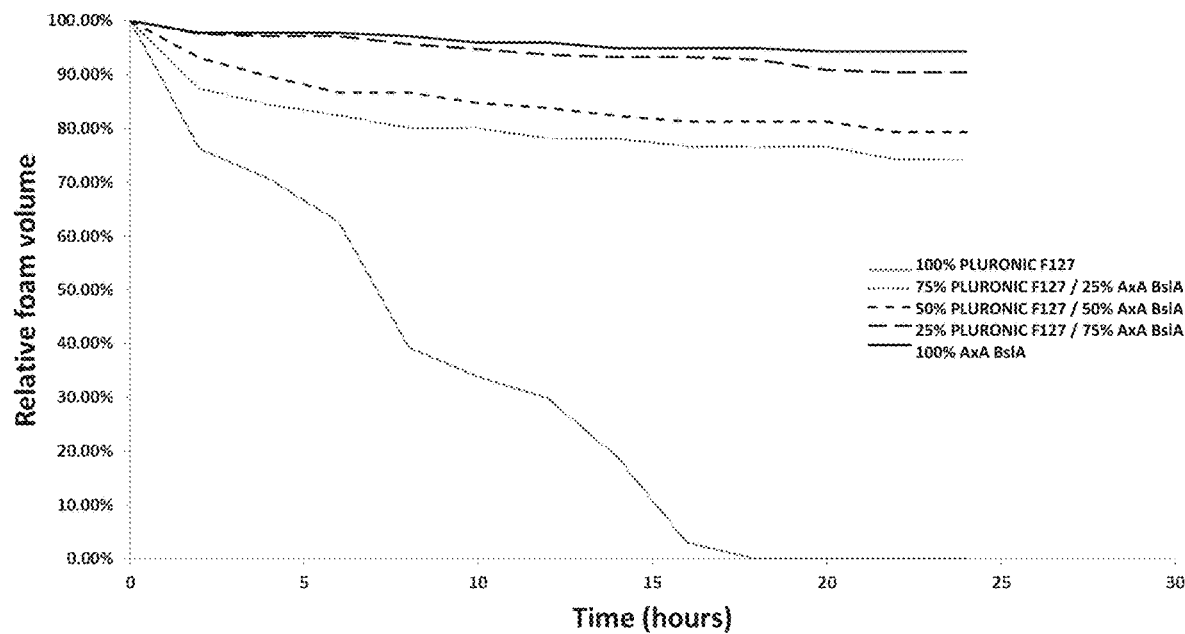
Figure 57:
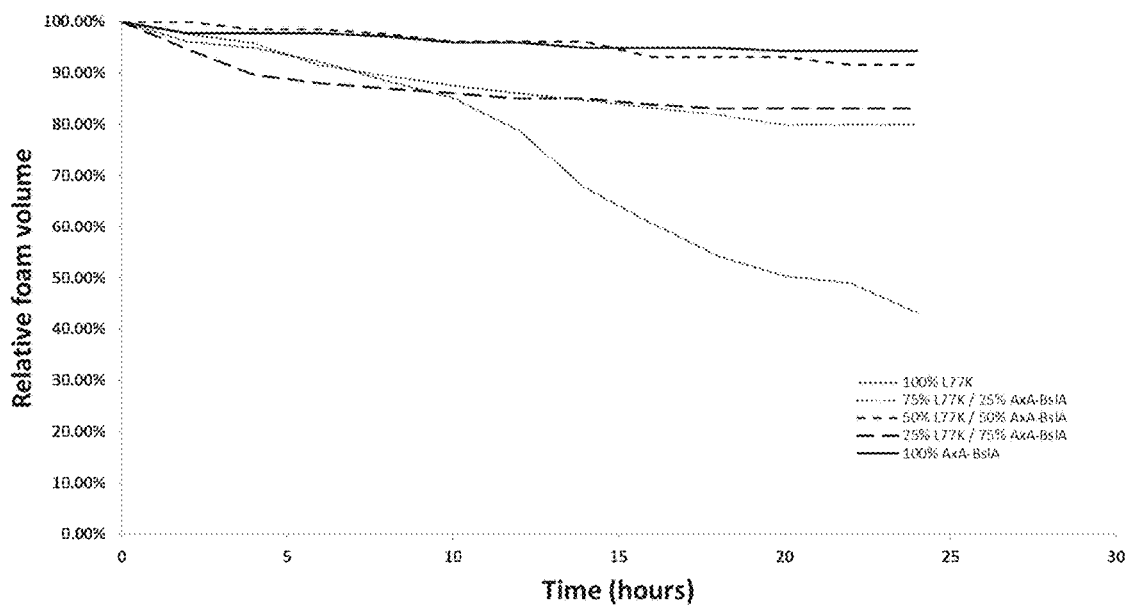
Figure 58:
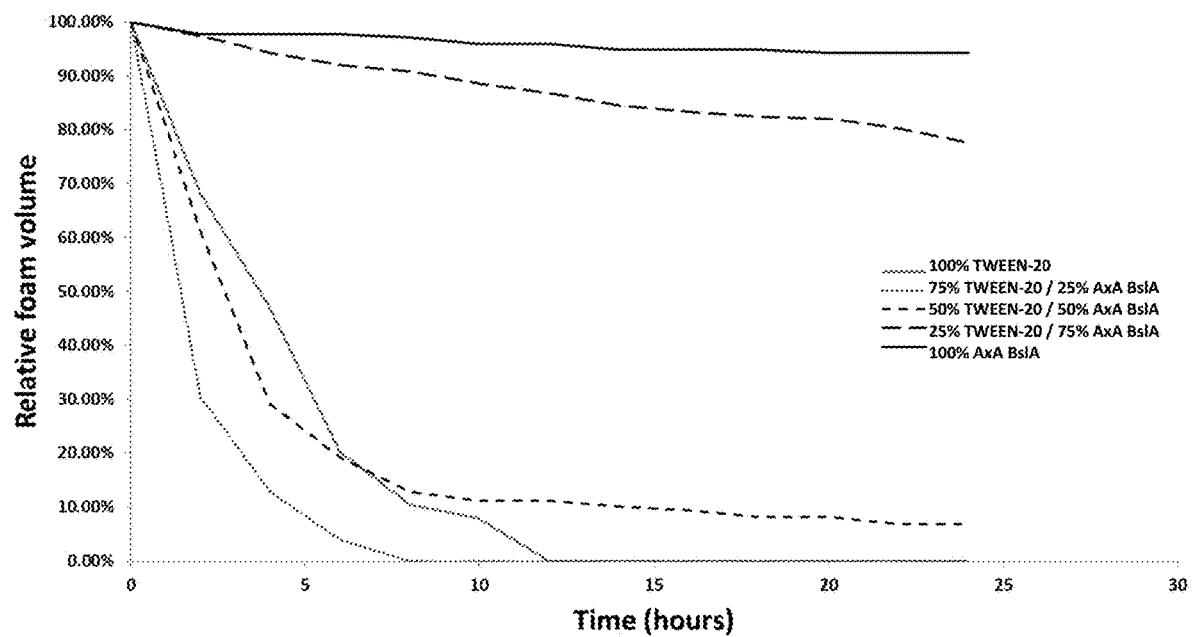
Figure 59:
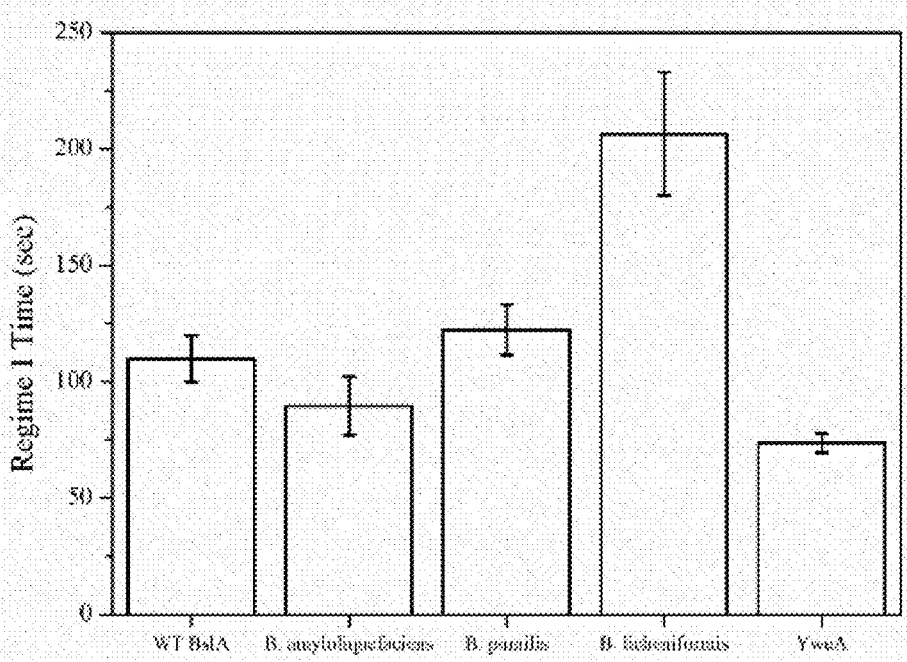
Figure 60:
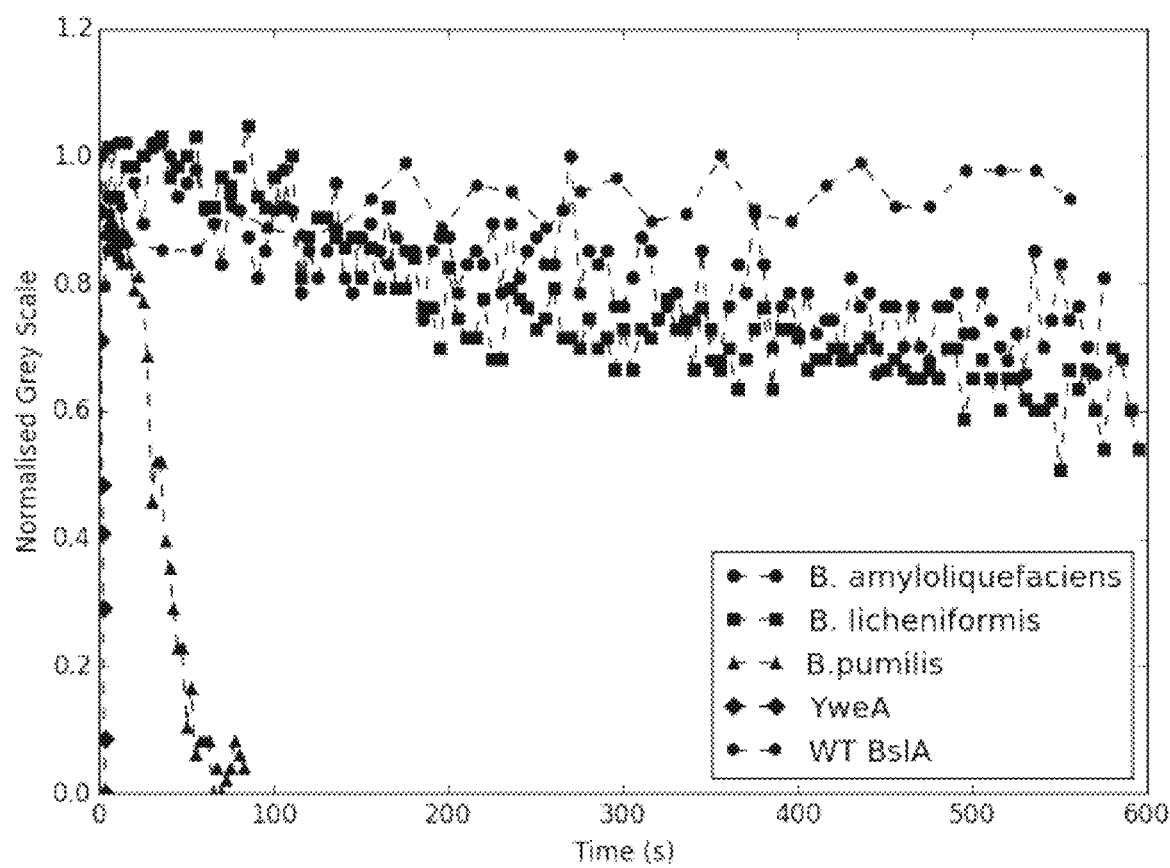
Figure 61:
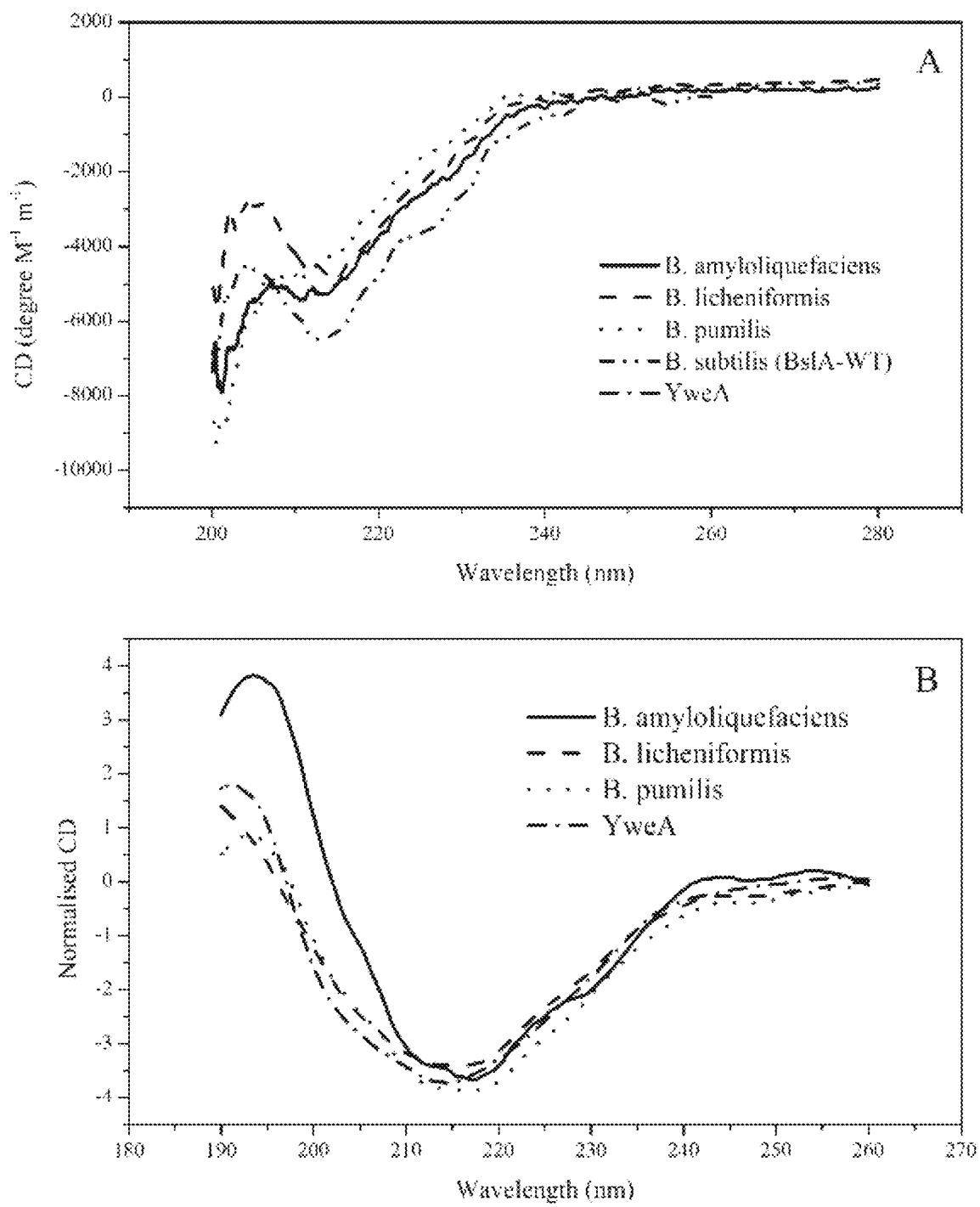

The raw data is presented as semi-transparent dotted lines, whereas data smoothed using Savitzky-Golay smoothing is represented by solid lines;

FIG. 4 shows TEM images of (a) WT-BslA and (b) BslA-L77K stained with uranyl acetate. Scale bar=100 nm. Insets: FFTs of (i) The entire TEM image, (ii) the selected square area in each image. The numbers in (a)(ii) correspond to the Miller indices of the 2D lattice structure;

FIG. 5 shows (a) the entire BslA decamer from the crystal structure with chains A-H displayed in light grey and chains I and J displayed in dark grey. The hydrophobic caps are displayed as surface representations, while the rest of the chains are displayed as cartoon backbone representations. (b) A depiction of the hydrophobic core of the decamer with the hydrophobic caps of chains A-H in light grey and the hydrophobic caps of chains I and J in dark grey. The hydrophobic caps comprise residues 75-81 (CAP1), 119-126 (CAP2), and 153-155 (CAP3). (c) A depiction of chain C, showing the hydrophobic residues (black) oriented outwards as opposed to (d) chain I, in which the hydrophobic residues have no particular orientation. Images were generated using Visual Molecular Dynamics[26] with PDB file 4BHU[1];

FIG. 6 is a schematic of BslA adsorption. When unbound (U), the conformation of the hydrophobic cap of WT-BslA orients the hydrophobic residues away from the aqueous medium, slowing the rate of adsorption (indicated by a small arrow). The L77K mutation removes the adsorption barrier by exposing some or all of the hydrophobic residues within the hydrophobic cap, increasing the rate of adsorption (indicated by a bold arrow). Once adsorbed onto the interface, the surface-bound WT-BslA (S) refolds to a conformation rich in β-sheet and is able to form strong lateral interactions with adjacent molecules, forming an organised lattice (S*) that under normal circumstances will not be removed from the interface (indicated by the crossed arrow). Surface bound BslA-L77K (S) forms a less well-organised lattice and can be removed from the interface with only minimal energy, such as droplet compression;

FIG. 7 shows a the percentage of spherical droplets that are observed when WT-BslA is co-emulsified with other surfactants (both BslA and surfactant at 0.1 mg/mL), where a low percentage of spherical droplets is indicative of the presence of BslA at the droplet interface;

FIG. 8 is a bar chart showing the percentage of spherical droplets remaining in emulsions made with 0.1 mg/mL of an alternative surfactant and then re-emulsified with 1 mg/mL WT-BslA;

FIG. 9 is a bar chart showing the percentage of spherical droplets remaining in emulsions made with WT-BslA and mixed with an alternative surfactant;

FIG. 10 is a bar chart showing the percentage of spherical droplets remaining in emulsions made with WT-BslA and re-emulsified with an alternative surfactant;

FIG. 11 shows a series of images of emulsions prepared by emulsifying decane in the presence of WT-BslA and re-emulsified in the presence of excess (a) CTAB, (b) SDS, (c) PLURONIC F127, (d) TWEEN-20, (e) Sodium caseinate and (f) Whey protein isolate. Scale bars=100 μm;

FIG. 12 shows an image of a water in oil (sunflower oil) emulsion made using WT-BslA;

FIG. 13 shows multiple emulsion droplets stabilised by emulsification of sunflower oil with WT-BslA in a single step in a rotor-stator. Note the asphericity of the droplets;

FIG. 14 shows emulsions after addition of (a) CTAB or (b) SDS at high (>10 mg/mL) concentrations, the asphericity of the emulsion droplets disappears, indicating that both CTAB and SDS were able to bind to the outer oil-water interface. However, the inner water-oil droplets remained, demonstrating that multiple emulsions created by stabilisation with WT-BslA are stable against the presence of competitive surfactants;

FIG. 15 shows (a) Decane and (b) sunflower oil emulsions stabilised by BslA-L77K;

FIG. 16 shows BslA stabilised foam prepared using 0.4 mg/mL WT-BslA at 0, 1, 12 and 25 hours;

FIG. 17 shows foam stabilised by WT-BslA and sodium caseinate with a total concentration of surfactant of 0.4 mg/mL at 0, 1, 12 and 25 hours: (a) 75% WT-BslA, 25% sodium caseinate; (b) 50% WT-BslA, 50% sodium caseinate; (c) 25% WT-BslA, 75% sodium caseinate; (d) 100% sodium caseinate;

FIG. 18 shows the relative volume of foams formed with varying ratios of WT-BslA to sodium caseinate over time;

FIG. 19 shows foam stabilised by WT-BslA and PLURONIC F127 with a total concentration of surfactant of 0.4 mg/mL at 0, 1, 12 and 25 hours: (a) 75% WT-BslA, 25% PLURONIC F127; (b) 50% WT-BslA, 50% PLURONIC F127; (c) 25% WT-BslA, 75% PLURONIC F127; (d) 100% PLURONIC F127;

FIG. 20 shows the relative volume of foams formed with varying ratios of WT-BslA to PLURONIC F127 over time;

FIG. 21 shows foam stabilised by WT-BslA and TWEEN-20 with a total concentration of surfactant of 0.4 mg/mL at 0, 1, 12 and 25 hours: (a) 75% WT-BslA, 25% TWEEN-20; (b) 50% WT-BslA, 50% TWEEN-20; (c) 25% WT-BslA, 75% TWEEN-20; (d) 100% TWEEN-20;

FIG. 22 shows the relative volume of foams formed with varying ratios of WT-BslA to TWEEN-20 over time;

FIG. 23 shows foam stabilised by WT-BslA and CTAB with a total concentration of surfactant of 0.4 mg/mL at 0, 1, 5 and 10 hours: (a) 75% WT-BslA, 25% CTAB; (b) 50% WT-BslA, 50% CTAB; (c) 25% WT-BslA, 75% CTAB; (d) 100% CTAB;

FIG. 24 shows foam stabilised by WT-BslA and SDS with a total concentration of surfactant of 0.4 mg/mL at 0, 1, 5 and 10 hours: (a) 75% WT-BslA, 25% SDS; (b) 100% SDS;

FIG. 25 shows foam stabilised by WT-BslA and BslA-L77K with a total concentration of surfactant of 0.4 mg/mL at 0, 1, 12 and 25 hours: (a) 75% WT-BslA, 25% BslA-L77K; (b) 50% WT-BslA, 50% BslA-L77K; (c) 25% WT-BslA, 75% BslA-L77K; (d) 100% BslA-L77K;

FIG. 26 shows the relative volume of foams formed with varying ratios of WT-BslA to BslA-L77K over time;

FIG. 27 shows foams stabilised by WT-BslA, A, 0.05 mg/mL; B, 0.1 mg/mL; C, 0.2 mg/mL; D, 0.3 mg/mL; E, 0.4 mg/mL; and F, 1 mg/mL. G shows a graph of relative foam volume against time for the foams from 0.2 mg/mL to 1 mg/mL;

FIG. 28 Left, ice cream mix aged with TWEEN 60 (0.3 wt %) for four hours at 4° C. Right, the same mix after heating to 38° C. for 10 minutes;

FIG. 29 Left, ice cream mix aged with TWEEN 60 (0.3 wt %) and WT-BslA (0.5 mg/mL) for four hours at 4° C. Right, the same mix after heating to 38° C. for 10 minutes;

FIG. 30 Left, ice cream mix aged with TWEEN 60 (0.03 wt %) for 18 hours at 4° C. Right, the same mix after heating to 38° C. for 10 minutes;

FIG. 31 Left, ice cream mix aged with WT-BslA (0.5 mg/mL) (no TWEEN-60) for 18 hours at 4° C. Right, the same mix after heating to 38° C. for 10 minutes;

FIG. 32 Left, ice cream mix aged with TWEEN 60 (0.03 wt %) and WT-BslA (0.5 mg/mL) for 18 hours at 4° C. Right, the same mix after heating to 38° C. for 10 minutes;

FIG. 33 Height of foams produced from four different ice cream mix compositions at different incubation times. Samples were incubated in a rotating wheel at 4° C.;

FIG. 34 The same air stability experiment as performed in FIG. 34, except the vessel size and thus air reservoir size was considerably smaller, increasing the longevity of the bubbles;

FIG. 35 Left, a representative cryoSEM image of ice cream without BslA, imaged on the same day as it was prepared. The image on the right is the same with highlighted regions which outline the measured ice crystals (or ice crystal cross-sectional areas). Measurements were made on five images at a magnification of 250×;

FIG. 36 A representative cryoSEM image of ice cream without BslA, imaged after 28 days of storage at −20° C. As is expected of an Ostwald ripened system, there are very few small ice crystals (<1000 µm$^2$) compared to the same sample after 0 days (FIG. 35). Measurements were made on eight images at a magnification of 250×;

FIG. 37 A representative cryoSEM image of ice cream containing BslA at 0.05 wt %, imaged on the same day as it was prepared. Measurements were made on five images at a magnification of 250×;

FIG. 38 A representative cryoSEM image of ice cream containing BslA at 0.05 wt %, imaged after 28 days of storage at −20° C.;

FIG. 39 Size distribution histograms of measured ice crystal cross-sectional areas for ice creams with and without BslA after 0 days and 28 days stored at −20° C.;

FIG. 40 A) Arithmetic mean of ice cream samples with and without BslA after 0 and 28 days. B) Geometric mean of ice cream samples with and without BslA after 0 and 28 days;

FIG. 41 A representative cryoSEM image of ice cream containing no BslA, imaged after 24 hours of storage at −20° C.;

FIG. 42 A representative cryoSEM image of ice cream containing no BslA, imaged after 24 hours of storage at −5° C.;

FIG. 43 A representative cryoSEM image of ice cream containing BslA at 0.05 wt %, imaged after 24 hours of storage at −20° C.;

FIG. 44 A representative cryoSEM image of ice cream containing BslA at 0.05 wt %, imaged after 24 hours of storage at −5° C.;

FIG. 45 Size distributions of ice crystal cross-sectional areas in (top left) −BslA ice cream stored at −20° C., (top right) −BslA ice cream stored at −5° C., (bottom left)+BslA ice cream stored at −20° C. and (bottom right)+BslA ice cream stored at −5° C.;

FIG. 46 Top, Arithmetic mean of ice crystal cross-sectional area in ice cream samples with and without BslA stored for 24 hours at −20° C. and −5° C. Bottom, Geometric mean of ice crystal cross-sectional area in ice cream samples with and without BslA stored for 24 hours at −20° C. and −5° C.;

FIG. 47 CD spectra of 0.1 mg/ml solutions of AxA-BslA (solid black line) and WT-BslA (dashed black line);

FIG. 48 Typical data from pendant drop tensiometry experiments on unfractionated AxA-BslA (solid black line) and monomeric WT-BslA (dashed black line) droplets in air. The concentration used in each experiment was 0.03 mg/ml. (a) IFT curves. The dotted grey line is a marker to indicate 72 mN/m. (b) Laplace fit error curves corresponding to the IFT curves in (a);

FIG. 49 TEM images of the rectangular lattice structure formed by (a) WT-BslA and (b) AxA-BslA;

FIG. 50 Contact angle images of a 5 µL droplet of water on (a) a hydrophobically functionalised, (b) unfractionated WT-BslA modified, (c) unfractionated AxA-BslA modified and (d) sodium caseinate modified glass cover slips;

FIG. 51 Left, AxA-BslA single emulsion prepared with decane. Right, AxA-BslA double emulsion prepared with glyceryl trioctanoate;

FIG. 52 Co-emulsification of 0.1 mg/mL (a,b,c) CTAB and (d,e,f) SDS with 0.1 mg/mL (a,d) AxA-BslA, (b,e) dimeric WT-BslA and (c,f) monomeric WT-BslA (dimeric WT-BslA incubated in 1 mM DTT overnight). These images represent columns 2, 3, and 4 in Table 4. Scale: Each image is 400 µm in width;

FIG. 53 Emulsions prepared by emulsifying 10% decane into AxA-BslA (0.1 mg/mL) mixed with 0.1 mg/mL of (a) CTAB, (b) SDS, (c) PLURONIC F127, (d) TWEEN-20, (e) Sodium caseinate, and (f) Whey protein isolate. Scale: Each image is 400 µm in width;

FIG. 54 Stability of AxA-BslA control foams over 24 hours;

FIG. 55 Stability of AxA-BslA/sodium caseinate composite foams over 24 hours;

FIG. 56 Stability of AxA-BslA/PLURONIC F127 composite foams over 24 hours;

FIG. 57 Stability of AxA-BslA/L77K-BslA composite foams over 24 hours;

FIG. 58 Stability of AxA-BslA/TWEEN-20 composite foams over 24 hours;

FIG. 59 Regime I Times for BslA Orthologues;

FIG. 60 Relaxation of BslA Orthologue Elastic Films. *B. amyloliquefaciens* (circles), *B. licheniformis* (squares), *B. pumilis* (triangles), YweA (diamonds), WT-BslA (hexagon), and L77K BslA (stars); and FIG. 61 Circular Dichroism of BslA orthologues. (A) Solution state circular dichroism spectra of BslA orthologues: *B. amyloliquefaciens, B. licheniformis, B. pumilus,* YweA, and WT-BslA. (B) Circular dichroism spectra of RIMEs: *B. amyloliquefaciens, B. licheniformis, B. pumilis,* and YweA. The spectra of YweA and the orthologues produced by *B. licheniformis* and *B. pumilus* are consistent with large scale β-sheet structure. However, the orthologue produced by *B. amyloliquefaciens* dimers from the other samples and has a double minimum at 213 and 217 nm. Comparing (A) and (B), it is clear that all the orthologues undergo a structural transition when bound to an interface. Note since the determination of amount of protein present within the RIME is undetermined, we have normalised the spectra by the HT value at 218 nm.

SPECIFIC DESCRIPTION OF EMBODIMENTS OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Expression of WT-BslA and BslA-L77K

The method of expressing a truncated form of WT-BslA (SEQ ID NO:2) and the BslA mutant BslA-L77K is described in Hobley et al.[1] which is incorporated herein by reference. References to "WT-BslA" in the examples given below refer to the truncated form of the wild type BslA minus a signal sequence (also known as BslA$_{42-181}$). References to BslA-L77K in the examples given below refer to the truncated form of the wild-type BslA minus a signal sequence and comprising a point mutation (at position 77, numbered relative to the full length BslA sequence).

The nucleotide sequences used to encode the various BslA proteins are given below.

BslA Reduces the Surface Tension of Water

Figure 1:
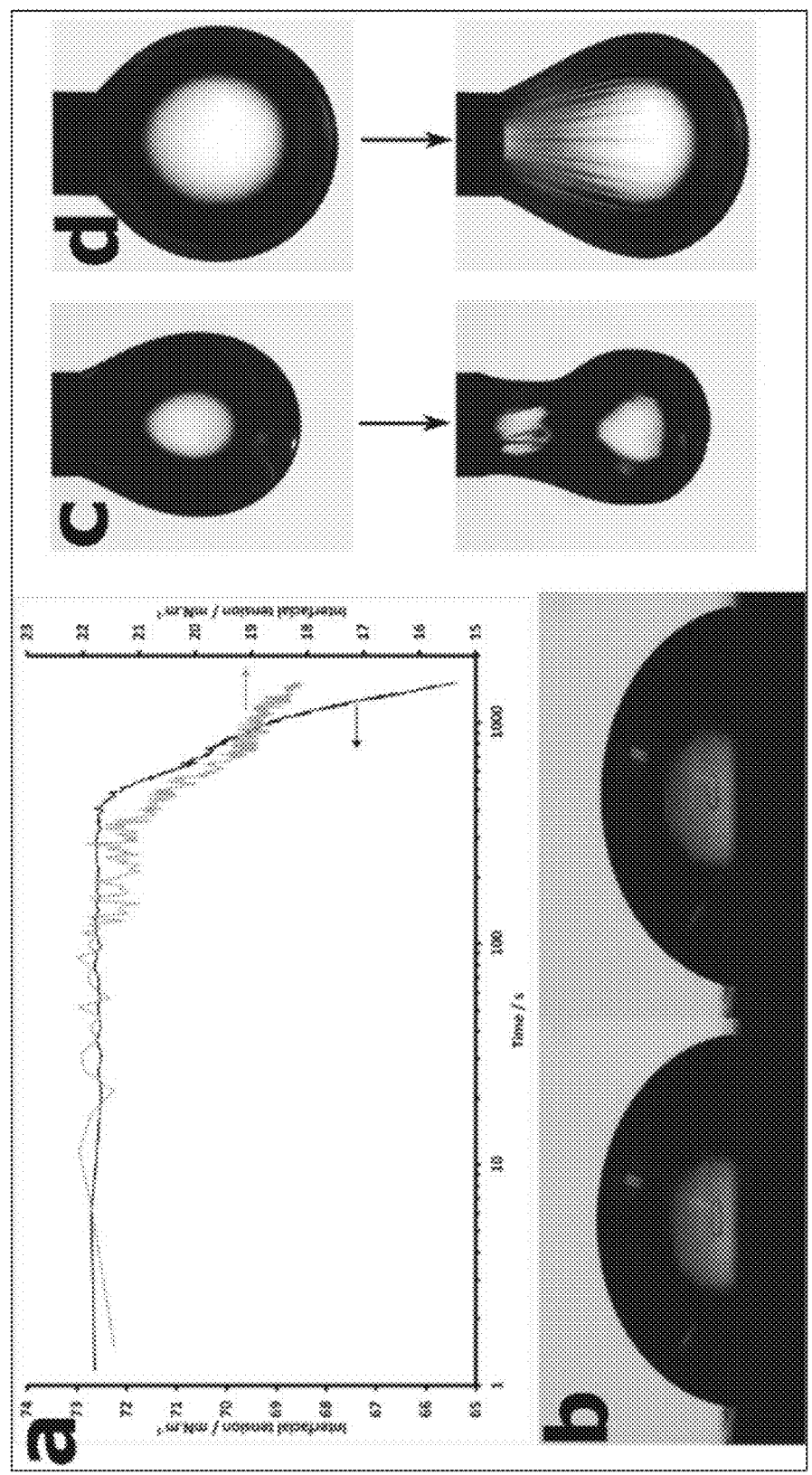
FIG. 1 (a) Interfacial tension profiles of a droplet WT-BslA (0.02 mg·mL$^{-1}$) in air (black line) and in a glyceryl trioctanoate (grey line). (b) A 50 μL droplet of WT-BslA (0.03 mg·mL$^{-1}$) on HOPG after 0 (left) and 30 (right) minutes (c) A 25 μL droplet of WT-BslA (0.02 mg·mL$^{-1}$) in air before and after compression, (d); A 40 μL droplet of WT-BslA (0.2 mg·mL$^{-1}$) in oil (triglyceride) before and after compression.

Pendant drop tensiometry was performed on aqueous droplets of BslA to observe the change in interfacial tension over time. In this technique, the shape of a drop is fitted to the Young-Laplace equation to measure the interfacial tension (IFT) at the droplet surface[27, 28], which usually decreases as the interface is populated by surface active species.[29] An increase in the error of the fit to the Young-Laplace equation indicates that a viscoelastic film has formed at the interface, and since a solid layer now separates the two liquid phases the concept of interfacial tension no longer applies. FIG. 1a shows the change in IFT of droplets of WT-BslA suspended in air and in oil. Typically, the interfacial tension of the water-air or water-oil interface drops after a lag period during which the population of protein at the interface is increasing. The magnitude of the decrease in IFT caused by BslA was consistently smaller than the typical drop in IFT observed for the class II fungal hydrophobin HFBII at similar concentrations and time scales.[30] For example, at 0.02 mg·mL$^{-1}$ and 300 s, BslA decreases the apparent IFT to 70.8±1 mN·m$^{-1}$, whereas HFBII decreases the IFT to ~56 mN·m$^{-1}$ under the same conditions.[30] However, despite this comparatively small decrease in IFT, the increase in the error of the Laplace fit indicates that a BslA film has already formed by 300 s, whereas HFBII must lower the IFT to at least 50 mN·m$^{-1}$ before the error of the Laplace fit increases.[30]

WT-BslA does not deform sessile drops at 0.01, 0.03 and 0.1 mg·mL$^{-1}$ after thirty minutes, even though visual inspection confirmed the formation of a viscoelastic film in each case (FIG. 1b). The formation of such a film was additionally confirmed at water-air or water-oil interfaces by the appearance of persistent wrinkles on the surface of pendant drops following compression.[1] FIG. 1c shows a WT-BslA droplet suspended in air before and after compression, while the WT-BslA droplet depicted in FIG. 1d was suspended in triglyceride oil. Taken together our results indicate that BslA forms interfacial films at lower protein densities than the class II fungal hydrophobins, and that the resulting films, while very stable, can form without causing a significant deformation in droplet shape.

Pendant drop tensiometry with drop shape analysis was performed on BslA solutions at concentrations between 0.01 and 0.1 mg·mL$^{-1}$. At low protein concentrations, the IFT initially remains unchanged for a lag time that is designated "Regime I"[31, 32] (FIG. 1a). During this period the interface becomes occupied by protein to a critical surface coverage above 50%,[31] and provides a measure of the rate at which the protein partitions to the interface. During Regime II, the IFT decreases steeply until the interface is saturated with adsorbed protein. Following saturation, the IFT levels off (Regime III), although a shallow gradient often indicates rearrangement of the protein layer. Although these characteristics can be seen in typical BslA dynamic interfacial tension response curves, the fit error of the Young Laplace equation to the droplet increased at some point during most experiments, indicating the formation of a viscoelastic layer.[30]

The time (t) it takes for a particle to adsorb onto an interface via diffusion can be predicted by Equation 1[33]:

$$\Gamma(t) = 2C_b \sqrt{\frac{Dt}{\pi}} \tag{1}$$

where $\Gamma$ is surface concentration, $C_b$ is bulk concentration and D is the diffusion coefficient of the particle. Equation 1 assumes that $C_b$ is unchanging and that there is no back diffusion from the interface.[33] We can estimate $\Gamma_{max}$ (for 100% surface coverage) to be 1.57 mg·m$^{-2}$ from TEM images of the BslA 2D lattice (FIG. 4a), while D was measured to be 9.87×10$^{-7}$ cm$^2$·s$^{-1}$ for monomeric BslA using dynamic light scattering (DLS). In cases where the error of the Laplace fit increased before a decrease in IFT was observed, then the onset time of any increase in the error of the Laplace fit was used.

WT-BslA vs BslA-L77K

Figure 2:
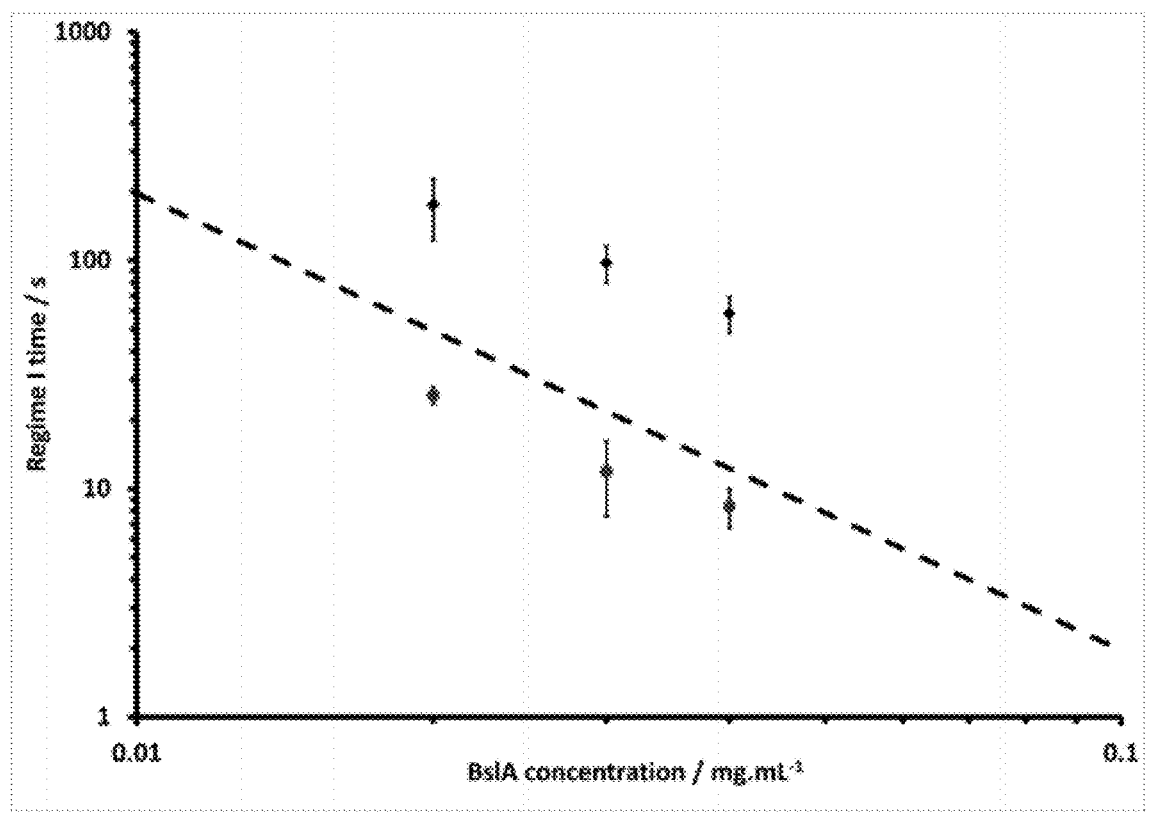
FIG. 2 is a plot of Regime I times versus concentration of WT-BslA (black diamonds) and BslA-L77K (circles). The dashed line represents the predicted time to reach a surface coverage of 1.57 mg·m$^{-2}$ for monomers with a diffusion coefficient of $9.87 \times 10^{-7}$ cm$^2$·s$^{-1}$ using Equation 1.

FIG. 2 shows a plot of Regime I time against BslA concentration for WT-BslA (black diamonds) and BslA-L77K (black circles) as well as the "ideal" Regime I times calculated from Equation 1 (dashed line). The results clearly demonstrate that WT-BslA takes more time to decrease the interfacial tension of a droplet (or increase the error of Laplace fit) in air than would be expected for a system that did not exhibit an adsorption barrier or back diffusion. In contrast, the BslA-L77K mutant reduced the interfacial tension of the droplet within the maximum calculated time for particles of equivalent size with no adsorption barrier. Under diffusion-limiting conditions, as determined by Equation 1, BslA at a concentration of 0.03 mg·mL$^{-1}$ should take 22 s to reach a surface concentration of 1.57 mg·m$^{-2}$. As the IFT will begin to decrease at a surface coverage below 100%, BslA should require less than 22 s to reduce the IFT of a droplet. At 0.03 mg·mL$^{-1}$ the Regime I time for WT-BslA was 97±18 s, compared to 12±4 s for BslA-L77K, confirming that BslA-L77K adsorption is purely diffusion-limited, whereas WT-BslA faces an additional barrier to adsorption. As the protein concentration was increased or decreased, the corresponding Regime I times followed the power law predicted by Equation 1.

Figure 3A:
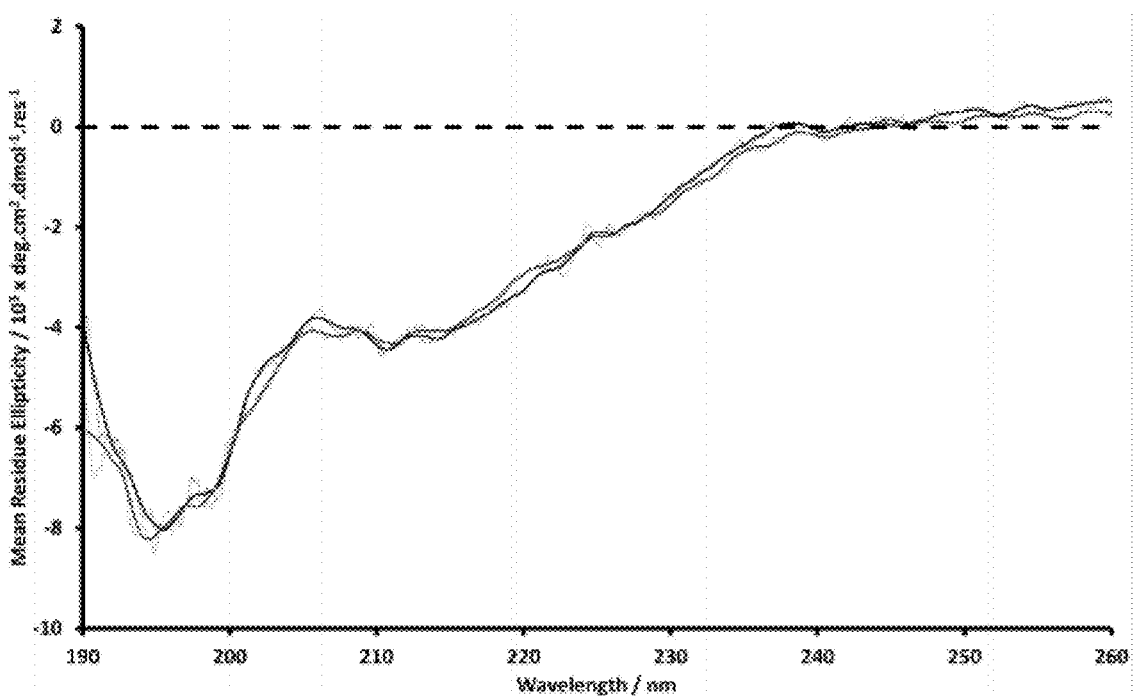
FIG. 3 (a) CD spectra of WT-BslA (black line) and BslA-L77K (grey line) in 25 mM phosphate buffer (pH 7). (b) CD spectra of refractive index matched emulsions stabilised by WT-BslA (black line) and BslA-L77K (grey line).
Figure 3B:
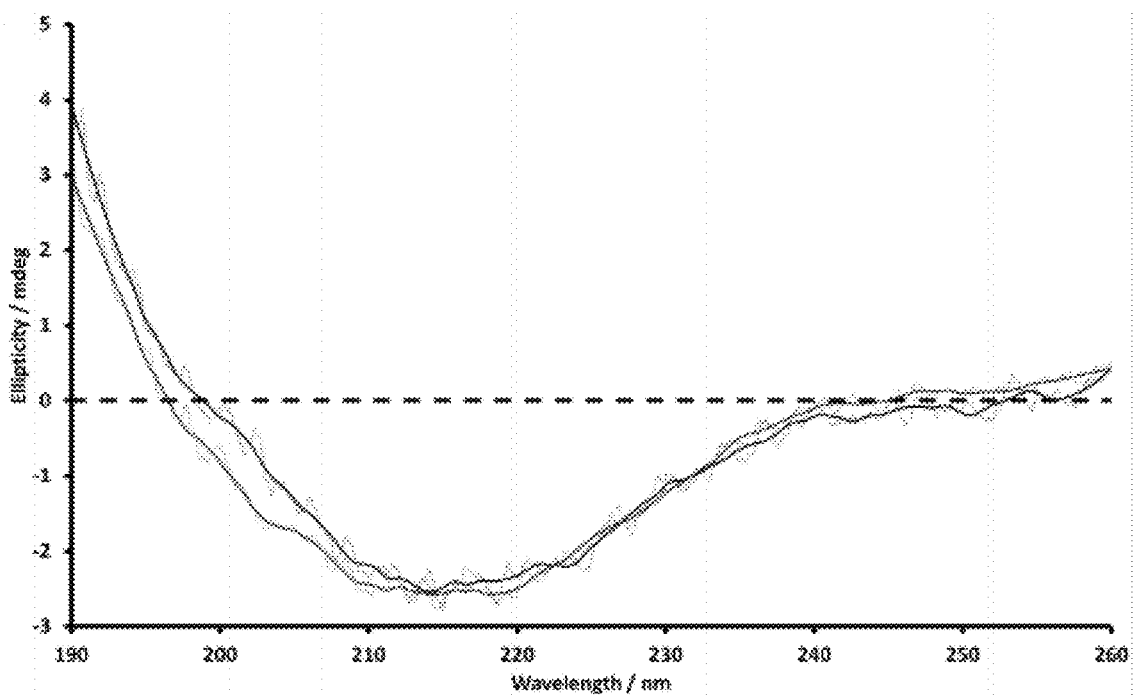

BslA Undergoes Conformational Change at Interface to a Structure Enriched in Beta-Sheet (CD Data) WT+L77K To study the conformation of BslA in aqueous solution and at an oil-water interface, circular dichroism (CD) spectroscopy of WT-BslA and the L77K mutant was performed in refractive index matched emulsions (RIMEs).[34] Refractive index matching enables the generation of oil-in-water emulsions without the light scattering that interferes with spectroscopic measurements. The folding of WT-BslA and BslA-L77K was very similar at pH 7 in phosphate buffer, with both curves exhibiting a maximum at ~205 nm, a minimum at ~212 nm and a shoulder at ~226 nm (FIG. 3a). The minimum at ~212 nm is consistent with some β-sheet structure, whereas the minimum at <200 nm suggests a significant contribution from random coil. On binding to the interface of decane-water emulsions, the CD spectra of both WT-BslA and BslA-L77K are altered substantially (FIG.

3b), exhibiting a positive signal below 200 nm and a minimum at 215-218 nm. Such features indicate a structural change to a form enriched in β-sheet conformation.[35]

BslA Forms Uniform Rectangular Lattice (TEM Data) WT Vs L77K

Figure 4A:
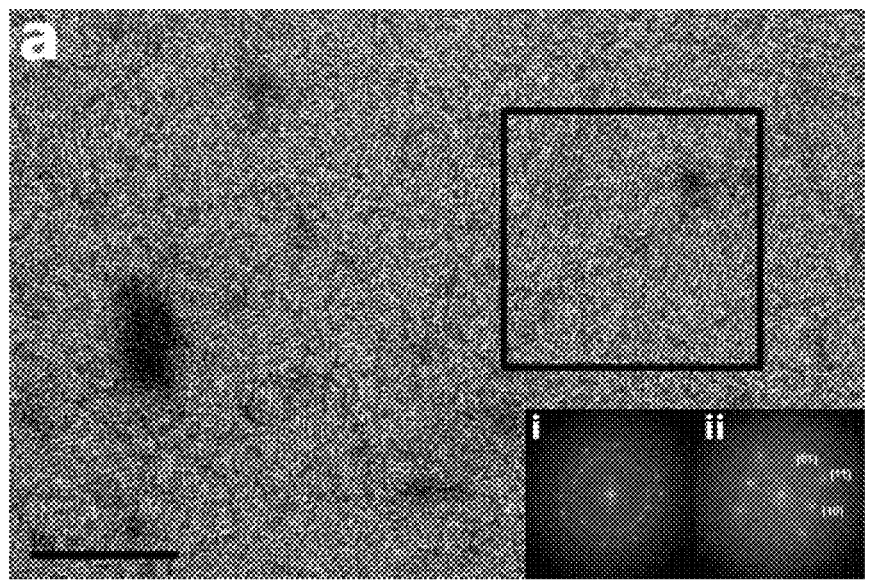
Figure 4B:
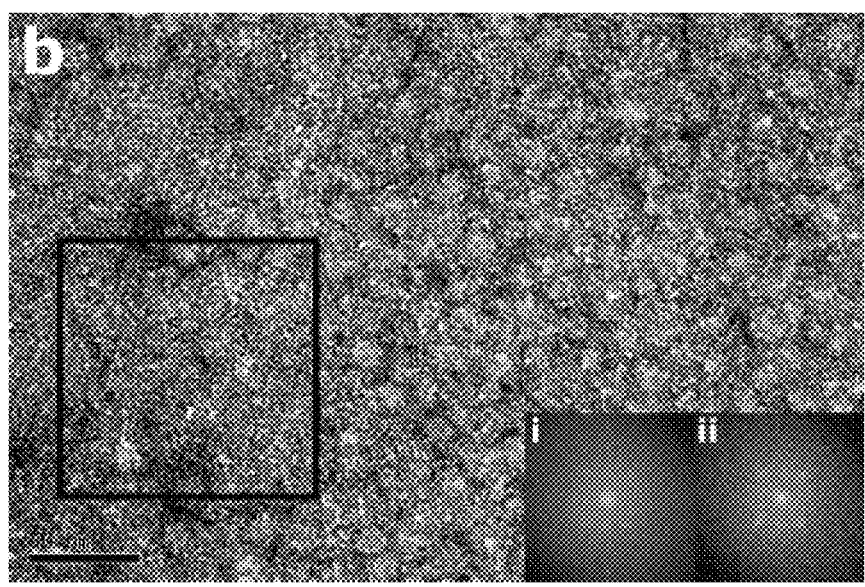

Transmission electron microscopy (TEM) of WT-BslA stained with uranyl acetate indicates that the protein forms a highly ordered rectangular lattice (FIG. 4a). Multiple domains of the WT-BslA lattice could be observed in any location on the grid. The observed domain areas varied from as small as 1000 nm$^2$ (~50 BslA molecules) up to 200000 nm$^2$ (>10000 BslA molecules). Less ordered "inter-domain" areas were also observed. Performing a Fast Fourier Transform (FFT) on TEM images of WT-BslA (FIG. 4a, insets) revealed a rectangular lattice ($\alpha=\beta=90°$, a≠b) with dimensions of d(10)=3.9 nm and d(01)=4.3 nm. TEM images of BslA-L77K revealed a predominantly disorganised arrangement of protein, which nonetheless contained patches of rectangular packed protein (FIG. 4b). The largest BslA-L77K domain size observed was approximately 20000 nm$^2$ (1250 BslA molecules). FFT on ordered domains of BslA-L77K revealed that the lattice parameters (d(10)=3.9 nm, d(01)=4.3 nm, $\alpha=\beta=90°$) were identical to the WT-BslA lattice (FIG. 4b, insets).

Crystal Structure Shows Two Distinct Forms

Although the crystal structure of WT-BslA features a large hydrophobic cap that allows the molecule to become anchored to a hydrophobic interface, kinetic measurements using the pendant drop method indicated that WT-BslA must overcome an energy barrier prior to or during adsorption (FIG. 2). The fact that WT-BslA exhibits an adsorption barrier suggests that the hydrophobic residues in the cap region are not optimally oriented outwards in solution. Moreover, CD spectroscopy indicates a secondary structure change between the stable, monomeric form of the protein in aqueous solution, and the protein self-assembled at an interface. Analysis of the X-ray crystal structure[1] reveals two substantially different cap configurations in the decameric repeat unit. Eight of the ten subunits are positioned with their caps in close proximity to each other in a micelle-like arrangement. In these proteins, the cap regions are in a β-sheet configuration with the hydrophobic residues oriented outwards from the protein (FIG. 5c), creating the oily core of the micelle. The remaining two subunits (chains I and J) are further away from the centre of the decamer (FIG. 5a-b) and the cap regions are in a random coil configuration with many of the hydrophobic residues oriented inwards towards the protein (FIG. 5d). This difference highlights the ability of the cap region to undergo substantial rearrangement in different solvent environments. The introduction of a positively charged amine would hinder this shielding mechanism as the lysine would orient outwards, forcing neighbouring hydrophobic residues to be exposed at the surface.

Emulsion Formation and Stability

WT-BslA stabilised and alternative surfactant (CTAB, SDS, PLURONIC F127, TWEEN-20, sodium caseinate or whey protein isolate) stabilised emulsions were prepared by placing 900 μL of 0.1 mg/mL WT-BslA or 0.1 mg/mL surfactant and 100 μL of decane in a vial before mixing the two phases using a rotor-stator at Level 6 (~30000 rpm) for 20 seconds. Emulsions prepared by co-emulsifying in the presence of two stabilisers (WT-BslA and each of the six surfactants, each at a concentration of 0.1 mg/mL) were mixed by vortexing 180 μL of aqueous phase and 20 μL of decane at top speed for 30 seconds. Re-emulsification of WT-BslA stabilised emulsions was performed via vortexing in the presence of an excess concentration (≥2 mg/mL) of each of the six surfactants mentioned above. Re-emulsification of surfactant stabilised emulsions in WT-BslA was performed via vortexing in the presence of 1 mg/mL WT-BslA.

Images and video recordings (not included here) were captured using an Olympus optical microscope and QCapture Pro software.

WT-BslA

Creating emulsions using WT-BslA as a stabiliser results in the formation of a population of aspherical droplets within the emulsion. The emulsification method used changes the proportion of aspherical droplets and also the extent of asphericity. The two methods used were the rotor-stator method and the vortexing method. WT-BslA stabilised emulsions prepared using a rotor-stator have fewer examples of anisotropic droplets and the extent of anisotropy is less than observed using the vortexing method.

WT-BslA stabilised emulsions were assessed by mixing and vortexing with surfactant additives. The surfactants chosen were CTAB (positively charged small molecule surfactant), SDS (negatively charged small molecule surfactant), PLURONIC F-127, TWEEN-20 (both non-ionic, polymeric surfactants), sodium caseinate and whey protein isolate (protein and protein mixture commonly used as surfactants in food). If the anisotropic morphology of the droplets was removed (i.e. the droplets became spherical), then it was concluded that the surfactant had adsorbed onto the droplet interface and potentially displaced the WT-BslA surface layer, although the experiments performed here do not provide direct evidence of BslA displacement. Videos of WT-BslA stabilised emulsion droplets becoming exposed to high concentrations of each of the six surfactants were recorded. Addition of CTAB and SDS caused the emulsion droplets to become spherical, whereas addition of PLURONIC F-127, TWEEN-20, sodium caseinate and whey protein isolate had no effect on droplet morphology.

When WT-BslA stabilised emulsions were re-emulsified by vortexing in the presence of an excess concentration of CTAB or SDS, all droplets became isotropic. Although most droplets became isotropic and spherical upon re-emulsification with non-ionic surfactants, examples of anisotropic droplets were still present. Re-emulsification in the presence of the protein samples sodium caseinate and whey protein isolate did not result in the formation of a large proportion of isotropic droplets.

In addition to assessing the stability of WT-BslA stabilised emulsions, emulsions were prepared in the presence of both WT-BslA and a surfactant additive at a 1:1 mass ratio. FIG. 7 shows the percentage of droplets in the emulsion that were spherical, and anisotropic droplets could be identified in all samples. The proportion of spherical droplets observed in the CTAB and SDS samples was higher than observed in the other four samples.

Examples of non-spherical droplets is shown in FIG. 9 for emulsions prepared by co-emulsifying decane in the presence of a 1:1 mass ratio of WT-BslA and an additional surfactant.

Emulsions stabilised by each of the six surfactants were prepared and re-emulsified in the presence of 1 mg·mL$^{-1}$ WT-BslA (FIG. 8). In every case, examples of non-spherical droplets were observed, indicating that WT-BslA could bind to the oil-water interface despite the presence of surfactant at the interface. This does not mean that WT-BslA could actively displace the surfactant. Instead, it is most likely that co-adsorption occurred due to WT-BslA binding to freshly exposed oil-water interface during emulsification. Furthermore, the presence of non-spherical droplets means that some sort of elastic film has formed at the interface.

Creating a WT-BslA stabilised emulsion with sunflower oil using a rotor-stator creates a multiple (water-in-oil-in-water) emulsion (FIG. 10). Despite the presence of internal droplets, the outer droplets are still often anisotropic. When mixed with excess CTAB or SDS (>100:1 mass ratio), the outer droplets became spherical, indicating that as with the single emulsions, the CTAB or SDS replaced (or coadsorbed with) the WT-BslA at the interface (FIG. 11). However, the surfactants did not disrupt the internal droplets, which remained present even after the outer droplets had become spherical. This property suggests that WT-BslA could be utilised to introduce stable internal droplets even when surfactants that remove WT-BslA from the interface are present.

BslA-L77K

BslA-L77K is a point mutant of WT-BslA that exhibits different interfacial properties to the wildtype. Specifically, the BslA-L77K interfacial film is able relax after compression, unlike WT-BslA. This is likely due to reduced level of 2D lattice formation observed in BslA-L77K samples relative to WT-BslA. Despite the ability of the film to relax, emulsions stabilised by BslA-L77K have the same properties as emulsions stabilised by WT-BslA—droplets are aspherical and multiple emulsions can be formed in a single step by emulsification of sunflower oil (FIG. 12).

As an example, of the stability of emulsions formed using WT-BslA, a mixture of glyceryl trioctanoate and water stabilised by WT-BslA was observed to be stable for up to 18 months. In comparison, a mixture of glyceryl trioctanoate and water stabilised by BslA-L77K had fully separated out into the constituent phases after 18 months, thereby showing that WT-BslA is the superior emulsion stabiliser over the mutant, and is an effective emulsion stabiliser over long time scales.

Foam Formation and Stability

Preparation of Foams

To form foams, 500 µL of "foaming solution" (0.4 mg/mL total surfactant containing 0-100% WT-BslA and 0-100% co-surfactant, in water) was placed in 1×1 cm cuvette. In a separate experiment, discussed below, foams were prepared using solutions of WT-BslA at concentrations between 0.05 mg/mL and 1 mg/mL.

A modified 25 gauge needle was connected to a 60 mL syringe and placed through a small hole at the bottom of the cuvette. The syringe was placed in a syringe pump and air was pumped through the "foaming solution". The syringe pump was set to pump at a rate of 5 mL/min. Once enough air had been passed through the foaming solution to form a foam, a cap was placed on top of the cuvette and wrapped in Parafilm. The needle was removed from the base of the cuvette and the hole was sealed with hot candle wax.

Imaging of Foams

The foams were placed in an incubator at 22° C. and imaged at a rate of 12 frames per hour for 25 hours. Foam volume was measured using ImageJ software by measuring foam height, while accounting for any cavities that developed within the foam.

Foams containing 0, 25, 50 and 75% WT-BslA and 100, 75, 50 and 25% surfactant respectively were created by injection of air into the foaming solution (500 µL) via a fine needle. The total concentration of subphase surfactants (including BslA) was 0.4 mg·mL$^{-1}$. The lifetime of the foams was monitored by imaging every five minutes for 10 hours or longer.

FIG. 13 shows a WT-BslA control foam at 0 hours, 1 hour, 12 hours and 25 hours. WT-BslA foams did not collapse or disproportionate significantly within the timeframe of the experiment (25 hours).

Mixed Surfactant Foam Data

Mixed WT-BslA/sodium caseinate foams are shown in FIGS. 14 and 15, the foams having, 75% WT-BslA, 25% sodium caseinate (a); 50% WT-BslA, 50% sodium caseinate (b); 25% WT-BslA, 75% sodium caseinate (c); 100% sodium caseinate (d). The foams are shown at 0 hours, 1 hour, 12 hours and 25 hours. The sodium caseinate control foam (100% sodium caseinate) had mostly collapsed after 25 hours. In contrast, all of the foams that contained WT-BslA did not collapse beyond what was observed in the WT-BslA control foam. However, increased disproportionation and/or coalescence was observed with increasing sodium caseinate concentration.

As well as enhancing the stability of protein (sodium caseinate) foams, the stability of non-ionic surfactant foams (PLURONIC F127 and TWEEN-20) was also improved by the addition of WT-BslA (FIGS. 16 and 17 for PLURONIC F127, FIGS. 18 and 19 for TWEEN-20). Control PLURONIC F127 and TWEEN-20 foams had collapsed by 10 hours and 5 hours respectively. The mixed 25/75 WT-BslA/PLURONIC F127 foam remained stable for significantly longer than the control PLURONIC F127 foam and had not completely collapsed by the end of the experiment (25 hours). The foams containing a higher WT-BslA content (50 and 75%) collapsed earlier than the foam containing only 25% WT-BslA, despite the onset of disproportionation occurring later.

Mixed WT-BslA/TWEEN-20 foams with 50 or 75% WT-BslA remained stable for far longer than the control TWEEN-20, but the 25/75 WT-BslA/TWEEN-20 foam had collapsed after 4 hours, earlier than the control TWEEN-20 foam.

Foams prepared using the positively charged surfactant CTAB were not enhanced by the presence of WT-BslA. In the experiments shown in FIG. 20, the presence of WT-BslA destabilised CTAB foams.

As SDS crystallises with phosphate buffer, WT-BslA was dialysed into pure water for foaming experiments with CTAB and SDS. WT-BslA in pure water does not foam, due to the low ionic strength. Despite this, the 75/25 WT-BslA/SDS mixture did create a foam that remained stable for 10 hours (FIG. 21), more than 10 times longer than the control SDS foam. 50/50 and 25/75 WT-BslA/SDS mixtures did not foam.

As BslA-L77K lacks a barrier to adsorption and reduces surface tension more readily than WT-BslA, it foams more effectively. FIGS. 22 and 23 shows mixed WT-BslA/BslA-L77K foams and a control BslA-L77K foam. The 75/25 and 50/50 WT-BslA/BslA-L77K foams were not formed effectively, but the foams remained relatively stable for the duration of the experiment (25 hours). Some of the shrinkage was observed in those foams may have been due to drying. The 25/75 WT-BslA/BslA-L77K and the BslA-L77K control foams were formed well and although they had not completely collapsed by the end of the experiment, significant collapse and disproportionation had begun in both samples.

BslA as Sole Surfactant, Foam Data

As mentioned above, experiments were undertaken to analyse the effect of concentration of BslA on foaming and foam stability, where BslA was the sole surfactant. This complements the data discussed above in which BslA was assessed in combination with co-surfactants.

Foams were prepared using 500 μL of "foaming solution", i.e. a solution of WT-BslA in water at concentrations from 0.05 mg/mL to 1 mg/mL (0.005 wt % to 0.1 wt %). The same foaming procedure and other experimental protocols as discussed above were used.

FIG. 28 shows the results of this experiment, with A (0.05 mg/mL) and B (0.1 mg/mL) showing essentially no foam formation, C (0.2 mg/mL) and D (0.3 mg/mL) demonstrating good foam formation, and E (0.4 mg/mL) and F (1 mg/mL) demonstrating excellent foam formation. The data shows that a stable foam could be formed at 0.2 mg/mL (0.02 wt %), but not at 0.1 mg/mL (0.01 wt %). At lower concentrations of BslA, e.g. up to 0.3 mg/mL, relatively large bubbles were formed within the foam, and this would suggest that higher concentrations of BslA are required to stabilise the bubbles quickly enough to keep them from coalescing to some extent during foam formation. At higher concentrations, e.g. 0.4 mg/mL and 1 mg/mL, much smaller bubbles, and hence a much finer foam, was formed, with the foam at 1 mg/ml being both very fine and highly consistent.

FIG. 28G shows a graph of relative foam volume (i.e. volume compared with time 0) against time for the foams from 0.2 mg/mL to 1 mg/mL BslA. All of the foams demonstrated significant stability over 24 hours. A foam formed with BslA at 1 mg/mL (0.1 wt %) was extremely stable.

Air Bubbles Stabilised by BslA

Air bubbles stabilised by BslA were formed by vigorously shaking, by hand, a 2 mg/ml solution of wt-BslA in 25 mM phosphate buffer for 90 seconds. The sample was then placed on a glass cover slip and imaged using an optical microscope. The morphology of the resulting air bubbles is typically non-spherical. The stability of BslA stabilised air bubbles were mixed in the presence of co-surfactants by applying an excess of six different surfactants: CTAB, SDS, PLURONIC F-127, TWEEN-20, Sodium Caseinate, and Whey Protein Isolate. The stability of the BslA stabilised air bubbles was determined by observing whether the air bubbles transformed from non-spherical to spherical in the presence of the co-surfactant.

Frozen Multiphase Products

Ice Cream Composition and Preparation

The composition of the ice creams prepared in each experiment reported here is as follows:
14 wt % coconut oil (melted)
12 wt % skimmed milk powder (SMP: 50% lactose, 35% milk proteins)
14 wt % sucrose
60 wt % water
Optional additives used:
 0.03 wt % TWEEN 60 (standard) or 0.3 wt % TWEEN 60
 0.05 wt % WT-BslA As the ice cream composition is identical in all experiments apart from the two additives, the following shorthand was used to describe the samples:
 −TWEEN-60, −BslA=no additives
 +TWEEN-60=only TWEEN-60 added
 +BslA=only BslA added
 +TWEEN-60, +BslA=both additives present To prepare the ice cream, SMP and sucrose were dissolved in water and melted coconut oil was pipetted on top of the solution. The mix was then sheared using a rotor-stator for 30 seconds. At this stage, the mix was split into four parts and any additives required (Tween and/or BslA) were added. Each aliquot was then re-homogenised three to four times in the rotor-stator for 20 seconds with 20 second pauses in between cycles. This homogenisation process was adjusted for the air stabilisation experiment to reduce the time between homogenising the first and last aliquots. In that experiment, the initial mix was homogenised four times for 30 seconds with a 30 second pause between cycles. The aliquots were then re-homogenised in the presence of additives for 30 seconds.

After the homogenisation step, the mixture was aged for sixteen hours (unless stated otherwise) at 4° C. in a slowly rotating wheel. After aging, the samples were placed in a Perspex insert in an aluminium bowl at −20° C. and manually stirred for 5 minutes. This simultaneously froze and aerated the mix, creating ice cream. In each experiment, the sample mass, freezing onset time and total "churn time" were monitored and recorded.

Measurement of Fat Droplet Stability

To demonstrate that BslA had successfully adsorbed onto the surface of the fat droplets in an ice cream mix, aged mixes, in which the fat droplets had partially coalesced, were first imaged using an optical microscope. The samples on the slide were then warmed to 38° C. to melt the fat. The samples were imaged again using optical microscopy to identify whether the partially coalesced droplets had retained their morphology. Retention of morphology demonstrated that BslA was present and stabilising the partially coalesced structure.

Measurement of Air Bubble Stability

To measure the stability of air bubbles in ice cream, the mixes were studied before the aging and freezing processes. As the mixing process incorporates some air into the ice cream mixture (prior to the simultaneous freezing and aeration step), it is possible to determine the longevity of those air bubbles in the mixture. Simply allowing the mix to cream and monitoring the stability of the resultant foam does not work as the aqueous phase quickly drains away, leaving a solid fat stabilised foam. Instead the mixtures were incubated at 4° C. on a rotating wheel (to prevent creaming). At various time points, the samples were removed from the rotating wheel and allowed to cream. The height of the foam was then imaged and measured to establish the air content of the sample at that moment in time. The samples were then returned to the rotating wheel to continue incubation. This process was repeated to gather data at several time points.

Measurement of Ice Crystal Stability

CryoSEM was used to study ice crystal stability against long term storage (4 weeks) at −20° C. and against temperature abuse (1 day stored at ~−5° C.). To ensure that ice cream samples loaded onto the cryoSEM sample stage had not melted, the samples were cut out using a narrow straw to produce a cylindrical "core" of ice cream. The cylinder of ice cream was placed onto a dab of cooled Tissue-Tek glue on a cooled sample stage. The stage and adhered ice cream were then immediately plunged into nitrogen slush (−210° C.) and subsequently placed into a precooled prechamber (−170° C.) attached to the SEM instrument. Maintenance of the cylindrical shape indicated the ice cream had not melted. A scalpel built in to the prechamber was used to fracture the ice cream cylinders revealing the structural features of the ice cream interior. At this stage, the prechamber was warmed to −90° C. for 10 minutes to etch the ice crystals embedded into the protein-sugar matrix. After re-cooling to −170° C., the samples were sputter-coated in gold-palladium before the sample was inserted into the cryoSEM chamber, which was also held at −170° C.

Results
Stabilisation of Partially Coalesced Fat Droplets

To improve the stability of ice cream, milk protein stabilised emulsions are aged for four hours at 4° C. in the presence of an "emulsifier" such as TWEEN 60. By undergoing this process, the emulsion droplets begin to partially coalesce as a result of fat crystallisation and TWEEN 60 weakening the droplet interface. FIG. 28 shows a typical ice cream mix with a high concentration of TWEEN 60 (0.3 wt %) after incubation at 4° C. for four hours. The presence of anisotropic droplets indicated that partial coalescence had occurred. After heating this solution to 38° C., the coconut oil (MP=24° C.) melted and the partially coalesced droplets returned to a spherical shape. Addition of WT-BslA (0.5 mg/mL) to the ice cream mix did not prevent partial coalescence of the droplets due to the action of TWEEN 60. However, after heating to 38° C., the anisotropic partially coalesced droplets were left intact as BslA at the interface formed a rigid film, preventing droplet relaxation (FIG. 29).

This experiment was repeated with samples that allowed the partial coalescence to proceed further. In certain cases, it was possible to image the same partially coalesced regions before and after heating. Without BslA present, the large partially coalesced structures melted into large spherical oil droplets (FIG. 30). The overall structure of the partially coalesced aggregates was retained, although the individual fat droplets appeared to coalesce after melting (FIG. 31 and FIG. 32). Interestingly, FIG. 31 demonstrates that BslA can help to instigate partial coalescence even without an emulsifier such as TWEEN-60 present, although partial coalescence was limited compared to TWEEN-60 samples. These images also show how partially coalesced droplets can surround and stabilise air bubbles in the mix.

Stabilisation of Air Phase

Four ice cream mixes containing either no additives, "TWEEN-60", "BslA" and "TWEEN-60+BslA" were foamed using a rotor-stator. The lifetime of the air bubbles was studied as described in the Experimental. From the data shown in FIG. 33, it is clear that addition of BslA stabilises the air bubbles as the sample still produced a foam after two hours incubating whereas the addition of TWEEN-60 in the absence of BslA caused almost immediate destabilisation of the bubbles. BslA helped to stabilise bubbles in the presence of TWEEN-60 although bubbles in the absence of both BslA and TWEEN survived a little longer. Performing the same experiment on samples in smaller vessels (with a much smaller air reservoir) caused both BslA-stabilised and control bubbles to survive for over 20 hours (FIG. 34). The disparity in survival time is likely a consequence of the mechanism of bubble destruction—disproportionation—which is accelerated in the presence of a large air reservoir. The addition of TWEEN-60 introduces a different form of destabilisation called coalescence. Coalescence is not possible in ice cream as the air bubbles are static, meaning that BslA should stabilise air bubbles in ice cream, even in the presence of an emulsifier.

Stabilisation of Ice Phase

CryoSEM was utilised to monitor ice crystal coarsening in ice creams with and without BslA. The ice creams studied in this section all contained TWEEN-60.

Samples were prepared for cryoSEM by cutting out a cylindrical section of ice cream and placing the cylinder onto cold Tissue-Tek glue on a chilled sample stage. The stage and sample were then immediately plunged into nitrogen "slush" at −210° C., freezing the sample onto the stage. The stage was then quickly transferred into a cold (−180° C.) prechamber under vacuum. At this point, visual inspection of the ice cream shape confirmed that the sample had not melted. The cylinder was then fractured using a scalpel (built into the prechamber) and the sample was "etched" by heating to −90° C. for 10 minutes. Then, the fractured and etched sample was coated in gold and platinum in preparation for imaging. At this point, the sample was moved into the main SEM chamber and imaging could begin.

CryoSEM Imaging of Ice Cream

The fractured sample morphologies revealed three primary distinctive structures: Ice crystals, air bubbles and the sugar-protein matrix. Ice crystals were identified by the presence of a flat surface at the bottom of a basin. This pitting is caused by the etching process, which causes sublimation of the ice. Air bubbles were observed as inward or outward facing large spherulites. The matrix was the material in between the ice crystals and air bubbles. Some oversized fat droplets could be seen embedded in the matrix and on the surface of air bubbles.

Ice crystals were identified by the flat surface at the bottom of the feature. The cross-sectional area was measured using ImageJ software. In instances where it was not clear whether the feature was an air bubble cavity or an ice crystal depression, the feature was ignored. Ice crystals were also ignored if they overlapped with the edge of the image. All of the samples were imaged at 250× magnification. The ice crystal areas were analysed by plotting the data as histograms and also taking the arithmetic and geometric means.

Two separate types of experiment were performed to study whether BslA had an effect on ice crystal coarsening during storage. In the first experiment, ice cream samples were studied under cryoSEM when fresh (on the same day as freezing and aeration occurred) and also after 28 days of being stored in a freezer at −20° C. In the second experiment, fresh ice cream samples were stored overnight at either −20° C. or at approximately −5° C. By "temperature-abusing" the sample, the rate of ice crystal coarsening is increased.

Effect of Storage at −20° C.

Analysis of cryoSEM images of fractured ice creams (FIG. 35-FIG. 38) revealed that the size distribution of ice crystals, which are measured as ice crystal cross-sectional areas, increases with storage time as Ostwald ripening of the ice occurs through the viscous, liquid sugar-rich matrix. After 28 days, the size distribution of ice crystals increased in both "−BslA" and "+BslA" samples compared to the same samples imaged at 0 days (FIG. 39). However, the coarsening was limited by the presence of BslA, as indicated by a comparison of both the arithmetic (Table 1 and FIG. 40, Right) and geometric means (Table 1 and FIG. 40, Left). The geometric mean limits the effect of large outliers in the data, so the relative values are not as affected by limited statistical analysis.

Data Summary

The average size and standard deviations of the data sets were:

TABLE 1

Summary of average crystal sizes in ice creams with and without BslA stored at −20° C. for 0 and 28 days.

| Minus BslA | | | Plus BslA | | |
| --- | --- | --- | --- | --- | --- |
| Age (days) | Arithmetic mean ($\mu m^2$) | Geometric mean ($\mu m^2$) | Age (days) | Arithmetic mean ($\mu m^2$) | Geometric mean ($\mu m^2$) |
| 0 | 1273.62 | 1010.61 | 0 | 1299.14 | 897.17 |
| 28 | 2380.53 | 1683.57 | 28 | 1838.58 | 1359.97 |

"Temperature Abused" Ice Creams

In this experiment, two ice cream samples with TWEEN-60 were prepared with and without BslA. The ice cream samples were split into two parts, with one part being stored at −20° C. overnight and the second part being stored at approximately −5° C. overnight. Analysis of cryoSEM images (FIG. 41-FIG. 44) revealed the size distribution of the ice crystals in both temperature abused increased markedly in comparison to the control samples stored at −20° C. (FIG. 45). Significantly, the ice crystals in the BslA-containing ice cream coarsened less than in the control sample both when comparing the arithmetic mean and the geometric mean (Table 2 and FIG. 46).

Data Summary

TABLE 2

Summary of average crystal sizes in ice creams with and without BslA stored for 24 hours at −20° C. and −5° C.

| | Minus BslA | | Plus BslA | |
| --- | --- | --- | --- | --- |
| Temperature (° C.) | Arithmetic mean ($\mu m^2$) | Geometric mean ($\mu m^2$) | Arithmetic mean ($\mu m^2$) | Geometric mean ($\mu m^2$) |
| −20 | 1156.10 | 836.45 | 1206.90 | 877.38 |
| −5 | 2663.39 | 1887.02 | 2268.78 | 1580.39 |

"AxA" Mutant BslA

Although BslA has a hydrophobic cap that is resistant to self-assembly in aqueous media, the C-terminal region contains two cysteine (C) residues at residue positions 178 and 180 that are capable of forming intermolecular disulfide bonds, thus allowing dimers, tetramers, hexamers and potentially higher order oligomers to form. Although dimers can still stabilise an air-water or oil-water interface, tensiometry experiments demonstrated that they bind via only one cap, leaving the second cap pendant in the aqueous phase. Thus, the presence of dimers will alter the surface chemistry of BslA-stabilised emulsions and foams and also reduce the effective concentration of adsorbable BslA in solution. By adding a reducing agent (e.g. 2-mercaptoethanol or dithiothreitol), it is possible to reduce WT-BslA dimers into its constituent monomers, but such reducing agents won't be usable in every application. To avoid the use of reducing agents while maintaining a functional, monomeric BslA solution, a mutant was developed that replaced the cysteine residues with alanine (A) residues. The mutations were carried out using primers such as SEQ ID NO:12-17. The resultant double mutant is given the shorthand name "AxA", as WT-BslA would be "CxC". The "x" represents any amino acid, although it is an alanine (A) in the experiments performed in this work. The results in this section demonstrate that a solution of unfractionated AxA-BslA functions in exactly the same way as a solution of monomeric WT-BslA, except the ability to cross-link into dimers has been removed.

AxA-BslA Forms a Stable, Monomeric Solution in Aqueous Media

When WT-BslA solutions are passed through a size-exclusion column, two peaks can clearly be resolved that multiangle laser light scattering confirms are attributed to a mixed population of monomers and dimers. Applying the same separation technique to the AxA mutant reveals only one peak that corresponds to a pure population of monomers. Performing SDS-PAGE chromatography on WT-BslA and AxA-BslA yields the same result—AxA-BslA exists as a pure population of monomers.

The Conformation of AxA-BslA is the Same as WT-BslA in Solution and at an Interface Circular dichroism spectroscopy (CD) confirmed that AxA-BslA is conformationally identical to WT-BslA in solution (25 mM phosphate buffer, pH 7), exhibiting the same maximum at ~205 nm, a minimum at ~212 nm and a shoulder at ~226 nm (FIG. 47). Upon binding to an oil-water interface, both WT-BslA and AxA-BslA undergo a folding change to a conformation richer in β-sheet. This was confirmed by measuring the CD spectra of WT-BslA and AxA-BslA when adsorbed to an oil-water interface in a refractive index matched emulsion. In each case, a positive at or below 200 nm was observed as well as a minimum between 215-218 nm.

The Kinetics to AxA-BslA Binding to an Air-Water Interface is Identical to WT-BslA Monomers Pendant drop tensiometry was used to study how long it takes for WT-BslA and AxA-BslA to bind to an air-water interface. In this case, the lag time ("Regime I time") before the interfacial tension (IFT) begins to drop was monitored and compared between monomeric WT-BslA and AxA-BslA samples at 0.03 mg/mL. The average Regime I time for monomeric WT-BslA was 97 s, whereas the average Regime I time for AxA-BslA was 102 s. FIG. 48a shows typical IFT curves for monomeric WT-BslA and AxA-BslA. In addition, the lag times before an increase in Laplace fit error in each sample were very similar (FIG. 48b) indicating that the viscoelastic films formed at the air-water interface at the same time (~100 s).

Both WT-BslA and AxA-BslA Form a Rectangular Lattice Upon Binding to an Interface Transmission electron microscopy of monomeric WT-BslA and AxA-BslA adsorbed onto a carbon film revealed that there is no difference in the two-dimensional arrangement of BslA molecules on the substrate (FIG. 49). Further, the lattice spacing of WT-BslA and AxA-BslA films was very similar, with d(10)=3.9 nm and d(01)=4.1-4.3 nm.

Wrinkles Formed by Both WT-BslA and AxA-BslA Film Compression do not Relax

Once a film has formed around a pendant drop of BslA solution submerged in oil, withdrawing a small amount (5 μL) of the droplet (total initial volume=40 μL) causes the film to compress and wrinkles to form. WT-BslA is known to form wrinkles that are incapable of relaxing as the WT-BslA molecules cannot be removed from the interface by such compression. Wrinkles formed in AxA-BslA films were also found to be incapable of relaxing as the wrinkles did not dissipate after formation due to compression.

Unfractionated AxA-BslA can Modify the Surface Hydrophilicity of a Hydrophobic Surface More Efficiently than Unfractionated WT-BslA Coating a surface with BslA can reverse the surface's hydrophobicity. To demonstrate this, Circular glass cover slips (diameter=10 mm) were first cleaned in 2% Hellmanex for 3 hours, before rinsing in Milli-Q water. They were then further cleaned in 1M HCl (in 50% ethanol) for 3 hours and then thoroughly rinsed in Milli-Q water again. The clean cover slips were then incubated in octadecyltrimethoxysilane for 24 hours before being cleaned in acetone, then ethanol and finally Milli-Q water. The hydrophobic cover slips were then dried at 50° C. for 1 hour.

The hydrophobic cover slips were coated in three different protein samples (unfractionated WT-BslA, unfractionated AxA-BslA and sodium caseinate) using the Langmuir-Blodgett technique. Briefly, hydrophobic cover slips were submerged in 0.05 mg/mL adsorbent solutions for five minutes and withdrawn vertically through air-water interface at a withdrawal rate of 5 mm/min. Excess solution was wicked from the edge of the cover slips, which were then left to dry on filter paper. Imaging and contact angle measurements were performed using a Krüss EasyDrop tensiometer.

Contact angle experiments revealed the contact angle of a 5 µL droplet of Milli-Q water against the cover slip surface. FIG. 21 shows images of the droplets of water against each glass cover slip. Table 3 summarises the measured contact angles after two minutes equilibration.

TABLE 3

Contact angles measured on each different surface.

| Cover slip type | Contact angle/° |
|---|---|
| Hydrophobic control | 96.6 |
| Unfractionated WT-BslA | 48.6 |
| Unfractionated AxA-BslA | 33.8 |
| Sodium caseinate | 86.8 |

The contact angle against the hydrophobic control cover slip was 96.6°. Functionalising with unfractionated WT-BslA, a mixture of monomers and dimers, reduced the contact angle to 48.6°. A further reduction in contact angle to 33.8° was achieved by using an unfractionated solution of AxA-BslA, which cannot form disulfide bridged dimers due to a lack of cysteine residues. FIG. 50 shows the images of the water drops against each cover slip. Sodium caseinate only reduced the contact angle to 86.8°, demonstrating the reversal of hydrophobicity achieved by BslA is not a general effect of binding proteins to hydrophobic surfaces.

AxA-BslA Emulsions

Just like observed with WT-BslA previously, AxA-BslA will make a single emulsion when prepared with decane and a double emulsion when prepared with a triglyceride oil like glyceryl trioctanoate (FIG. 51). These emulsions were prepared using an AxA-BslA concentration of 0.2 mg/mL at an oil volume fraction of 0.2 using a rotor-stator.

Resistance of Emulsions to Surfactants

The behaviour of AxA-BslA stabilised emulsions against the effect of surfactants is very similar to WT-BslA. The primary difference was the observation that AxA-BslA (purely monomeric BslA) is resistant to displacement by sodium dodecyl sulfate (SDS), whereas it was previously observed that WT-BslA was not. This is likely due to the presence of dimers in the latter sample, as resistance to SDS could be recovered by the addition of dithiothreitol (DTT) to the primarily dimeric WT-BslA solution, reducing the dimers to monomers.

Another difference between AxA-BslA and dimeric WT-BslA was the observation that emulsions stabilised with dimeric WT-BslA were resistant to displacement by cetyl trimethylammonium bromide (CTAB) during co-emulsification, whereas the purely monomeric AxA-BslA was not. Previously, it was noted that WT-BslA was not resistant to CTAB, presumably as it contained a mixture of monomers and dimers. The overall conclusion is that BslA monomers (either WT or AxA) can maintain a presence at the interface in the presence of SDS, but not CTAB, whereas WT-BslA dimers can remain at the interface in the presence of CTAB, but not SDS. The observations regarding resistance to SDS and CTAB are summarised in Table 4 and FIG. 52.

TABLE 4

Summary of emulsion drop shapes after co-emulsification between BslA and CTAB or SDS (all at 0.1 mg/mL). The "S" denotes that all droplets were spherical, indicating that BslA had no influence on drop morphology. "NS" denotes that non-spherical droplets were present, confirming that BslA was at the interface and causing the trapped anisotropic droplet shapes.

| | WT-BslA (previous) | AxA-BslA | WT-BslA dimers | WT-BslA dimers + DTT |
|---|---|---|---|---|
| CTAB | S | S | NS | S |
| SDS | S | NS | S | NS |

Co-Emulsification of AxA-BslA and Surfactants

Co-emulsified emulsions were prepared by vortexing AxA-BslA (90 uL, 0.2 mg/mL), surfactant (90 uL, 0.2 mg/mL) and decane (20 uL) in a PCR tube for 1 minute. Non-spherical emulsion droplets were observed in all co-emulsified samples except for the AxA-BslA/CTAB emulsion (FIG. 52).

Addition of Excess Surfactant to BslA Emulsions

The stability of preformed AxA-BslA emulsions to a high concentration of surfactant (5 mg/mL) was monitored by gently mixing the surfactant solution (10 mg/mL) at a 1:1 volume ratio with a vortexed AxA-BslA emulsion prepared using 0.1 mg/mL AxA-BslA. The results were similar to WT-BslA, except SDS (as with co-emulsification) was unable to displace AxA-BslA from the oil-water interface with gentle mixing (FIG. 53).

Stability of AxA-BslA Foams and AxA-BslA-Surfactant Composite Foams

AxA-BslA foams behaved similarly to the WT-BslA foams studied previously. The composite foams prepared with BslAL77K, sodium caseinate, PLURONIC F127 and TWEEN-20 also demonstrated similar stability. The concentration of AxA-BslA and the surfactants in the composite foams was 0.4 mg/ml. They were mixed at different ratios to provide the different compositions. Foams were created by pushing air from a syringe through a fine hole (<100 µm diameter) into 1 mL of BslA and/or surfactant solution. The time course graphs for each foam are shown in FIGS. 54-58.

Hydrophobic Sand

Hydrophobic sand was produced in house by functionalising sand with dichloro-dimethyl silane. The hydrophobised sand was then incubated in a 0.2 mg/ml WT-BslA solution overnight. The following day, the sand was placed in a drying oven at 50° C. and allowed to dry for 2 hours. The sand was placed in a thin layer on a cavity slide. A 20 µL sessile drop of MilliQ water was placed on the layer of sand and imaged using the Krüss Easy Drop.

The drop of water was observed to sit on top of the layer of hydrophobic sand, but was adsorbed into the layer of hydrophobic sand that had been treated with WT-BslA. Accordingly, this result showed that the treatment of the hydrophobic sand with BslA increased the hydrophilicity of the hydrophobic sand such that the water was able to wet the sand and thereby be absorbed by it.

BslA Orthologues

We performed pendant drop tensiometry on BslA orthologues produced by three different organisms: *B. amyloliquefaciens*, *B. licheniformis*, and *B. pumilis* along with the protein YweA (*B. subtilis*). Samples were prepared by diluting each protein in phosphate buffer to a concentration of 0.03 mg ml$^{-1}$. Droplets were expelled in air and the interfacial tension was measured using standard techniques. As was the case with BslA produced by *B. subtilis*, once an elastic film forms around the droplet the measured interfacial tension becomes a meaningless quantity. A good indication of when the film forms is by monitoring the fit error. Regime I times were then extracted one of two ways: (1) the transition time between regimes I and II when the fit error was still low (<0.4 µm); or (2) when the fit error increased to a threshold value (>0.75 µm). Each reported Regime I time is the average of 4 experiments. The results can be found in FIG. 59. We find that the Regime I times of *B. amyloliquefaciens* BslA and *B. pumilus* BslA are within error of *B. subtilis* BslA. However, the Regime I time of *B. licheniformis* BslA is nearly twice as long as the other samples. The Regime I time for YweA was faster by ~25%.

glycerol solution. The addition of the glycerol index matches the emulsion droplets allowing for light to pass through the sample. We measure CD spectra using a 0.01 cm path length quartz cuvette. The results are shown in FIG. 61B. Comparing FIG. 60A to FIG. 61B, it is clear that the orthologues undergo a structural transition when adsorbed to the interface. The spectra of YweA and the orthologues produced by *B. licheniformis* and *B. pumilus* are consistent with large scale β-sheet structure and is very similar to what we observe for WT-BslA. However, the orthologue produced by *B. amyloliquefaciens* differs from the other samples and has a double minimum at 213 and 217 nm.

TABLE 5

|  | BslA | *B. licheniformis* | *B. amyloliquifaciens* | *B. pumilus* | YweA |
|---|---|---|---|---|---|
| Regime I | WT | Slow | WT | WT | Fast |
| Film Relaxation | WT | WT | WT | Fast | Very Fast |
| Solution CD | WT | WT | Weak min. | No min. | WT |
| RIMES CD | β-sheet | β-sheet | α-helix? | β-sheet | β-sheet |
| TEM | crystal | crystal | crystal domains | crystal domains | crystal |

We also measured the relaxation of the elastic films formed by the orthologues. Samples were diluted to a concentration of 0.2 mg ml$^{-1}$ in phosphate buffer. A droplet (40 µL) was then expelled into glyceryl trioctanoate and allowed to equilibrate for 30 minutes. After equilibration, the droplet was compressed by retraction of 5 µL. A video (2 fps for 10 minutes) was recorded of the wrinkles formed in the elastic film. Film relaxation was measured by loss of wrinkles as measured by the reduction in normalised grey scale values. The results are shown in FIG. 60. We find that *B. amyloliquefaciens* and *B. licheniformis* BslA exhibit very similar behaviour, showing very slow relaxation over the time window of the experiment. In contrast, YweA relaxes extremely rapidly in less than 5 seconds; *B. pumilus* BslA relaxes within a minute. For comparison, YweA relaxes more quickly than L77K BslA (FIG. 60).

Circular dichroism (CD) spectroscopy was used to study the conformation of the BslA orthologues in aqueous solution and at an oil-water interface. Solution state CD measurement were performed on samples diluted to a concentration of 0.03 mg ml$^{-1}$ and measured in a 1 cm path length quartz cuvette. Results are shown in FIG. 61A. Qualitatively, the spectra are reminiscent of the solution state CD spectrum for WT-BslA. One distinction can be found for the orthologue produced by *B. pumilus* where there is no apparent minimum between 210-218 nm, as can be found for the other proteins.

In order to investigate the conformation of the proteins at an interface we performed Circular Dichroism (CD) on oil in water emulsions made from the orthologues. Typically, emulsions would be opaque and strongly scatter light in the far UV. To solve this problem we use refractive indexed matched emulsions (RIMEs) to obtain the spectra. We make a standard water in oil emulsion using a protein solution of 0.5 mg ml$^{-1}$ mixed with a 20% decane (by volume). The emulsions are prepared by rotor stator for 5 minutes. The emulsions are allowed to cream and we introduce a washing step in order to remove any protein still present in solution by removing the supernatant and replacing it with fresh buffer. The sample is then emulsified and allowed to cream again. We remove supernatant and replace it with glycerol to a final amount of 59% by mass. Finally, we emulsify this Sequences Relevant to Present Invention Full length WT-BslA (SEQ ID NO: 1)

MKRKLLSSLA ISALSLGLLV SAPTASFAAE STSTKAHTES

TMRTQSTASL FATITGASKT EWSFSDIELT YRPNTLLSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPCGC N

WT-BslA truncated, BslA$_{42-181}$ (SEQ ID NO: 2)

MRTQSTASL FATITGASKT EWSFSDIELT YRPNTLLSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPCGC N

Full length BslA-L77K (SEQ ID NO: 3)

MKRKLLSSLA ISALSLGLLV SAPTASFAAE STSTKAHTES

TMRTQSTASL FATITGASKT EWSFSDIELT YRPNTLKSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPCGC N

BslA-L77K truncated (SEQ ID NO: 4)

MRTQSTASL FATITGASKT EWSFSDIELT YRPNTLKSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPCGC N

DNA sequence used by *Bacillus subtilis* to encode full length wild type BslA protein.

(SEQ ID NO: 5)
ATGAAACGCAAATTATTATCTTCTTTGGCAATTAGTGCATTAAGTCTCGG

GTTACTCGTTTCTGCACCTACAGCTTCTTTCGCGGCTGAATCTACATCAA

CTAAAGCTCATACTGAATCCACTATGAGAACACAGTCTACAGCTTCATTG

TTCGCAACAATCACTGGCGCCAGCAAAACGGAATGGTCTTTCTCAGATAT

CGAATTGACTTACCGTCCAAACACGCTTCTCAGCCTTGGCGTTATGGAGT

TTACATTGCCAAGCGGATTTACTGCAAACACGAAAGACACATTGAACGGA

AATGCCTTGCGTACAACACAGATCCTCAATAACGGGAAAACAGTAAGAGT

TCCTTTGGCACTTGATTTGTTAGGAGCTGGCGAATTCAAATTAAAACTGA

ATAACAAAACACTTCCTGCCGCTGGTACATATACTTTCCGTGCGGAGAAT

AAATCATTAAGCATCGGAAATAAATTTTACGCAGAAGCCAGCATTGACGT

GGCTAAGCGCAGCACTCCTCCGACTCAGCCTTGCGGTTGCAACTAA

GST-TEV-BslA Construct Sequences

These are the sequences of constructs used to express and then purify BslA (BslA$_{42-181}$, truncated form) and the L77K variant from *E. coli*.

Key:
Precision Recognition Site
TEV Site
BslA 42-181
GST Sequence from pGEX 6P-1
Added Stop Site Nucleotide sequence (SEQ ID NO: 6):
<u>ATGTCCCCTATACTAGGTTATTGGAAAATTAAGGGCCTTGTGCAACCCACTCGACTTCTTTTGGAATA</u>

<u>TCTTGAAGAAAATATGAAGAGCATTTGTATGAGCGCGATGAAGGTGATAAATGGCGAAACAAAAAGT</u>

<u>TTGAATTGGGTTTGGAGTTTCCCAATCTTCCTTATTATATTGATGGTGATGTTAAATTAACACAGTCT</u>

<u>ATGGCCATCATACGTTATATAGCTGACAAGCACAACATGTTGGGTGGTTGTCCAAAAGAGCGTGCAGA</u>

<u>GATTTCAATGCTTGAAGGAGCGGTTTTGGATATTAGATACGGTGTTTCGAGAATTGCATATAGTAAAG</u>

<u>ACTTTGAAACTCTCAAAGTTGATTTTCTTAGCAAGCTACCTGAAATGCTGAAAATGTTCGAAGATCGT</u>

<u>TTATGTCATAAAACATATTTAAATGGTGATCATGTAACCCATCCTGACTTCATGTTGTATGACGCTCT</u>

<u>TGATGTTGTTTTATACATGGACCCAATGTGCCTGGATGCGTTCCCAAAATTAGTTTGTTTTAAAAAAC</u>

<u>GTATTGAAGCTATCCCACAAATTGATAAGTACTTGAAATCCAGCAAGTATATAGCATGGCCTTTGCAG</u>

<u>GGCTGGCAAGCCACGTTTGGTGGTGGCGACCATCCTCCAAAATCGGAT</u><u>CTGGAAGTTCTGTTCCAGGG</u>

<u>GCCCCTGGGATCC</u><u>GAAAATTTATATTTTCAA</u>ATGAGAACACAGTCTACAGCTTCATTGTTCGCAACAA

TCACTGGCGCCAGCAAAACGGAATGGTCTTTCTCAGATATCGAATTGACTTACCGTCCAAACACGCTT

CTCAGCCTTGGCGTTATGGAGTTTACATTGCCAAGCGGATTTACTGCAAACACGAAAGACACATTGAA

CGGAAATGCCTTGCGTACAACACAGATCCTCAATAACGGGAAAACAGTAAGAGTTCCTTTGGCACTTG

ATTTGTTAGGAGCTGGCGAATTCAAATTAAAACTGAATAACAAAACACTTCCTGCCGCTGGTACATAT

ACTTTCCGTGCGGAGAATAAATCATTAAGCATCGGAAATAAATTTTACGCAGAAGCCAGCATTGACGT

GGCTAAGCGCAGCACTCCTCCGACTCAGCCTTGCGGTTGCAACTAA

Protein sequence-BslA (42-181 truncated form) linked to GST (SEQ ID NO: 7):
<u>MSPILGYWKIKGLVQPTRLLLEYLEEKYEEHLYERDEGDKWRNKKFELGLEFPNLPYYIDGDVKLTQS</u>

<u>MAIIRYIADKHNMLGGCPKERAEISMLEGAVLDIRYGVSRIAYSKDFETLKVDFLSKLPEMLKMFEDR</u>

<u>LCHKTYLNGDHVTHPDFMLYDALDVVLYMDPMCLDAFPKLVCFKKRIEAIPQIDKYLKSSKYIAWPLQ</u>

<u>GWQATFGGGDHPPKSD</u><u>LEVLFQGPLGS</u><u>ENLYFQ</u>MRTQSTASLFATITGASKTEWSFSDIELTYRPNTL

LSLGVMEFTLPSGFTANTKDTLNGNALRTTQILNNGKTVRVPLALDLLGAGEFKLKLNNKTLPAAGTY

TFRAENKSLSIGNKFYAEASIDVAKRSTPPTQPCGCN

GST-TEV-BslA (L77K) construct sequences (SEQ ID NO: 8).
<u>ATGTCCCCTATACTAGGTTATTGGAAAATTAAGGGCCTTGTGCAACCCACTCGACTTCTTTTGGAATA</u>

<u>TCTTGAAGAAAATATGAAGAGCATTTGTATGAGCGCGATGAAGGTGATAAATGGCGAAACAAAAAGT</u>

<u>TTGAATTGGGTTTGGAGTTTCCCAATCTTCCTTATTATATTGATGGTGATGTTAAATTAACACAGTCT</u>

<u>ATGGCCATCATACGTTATATAGCTGACAAGCACAACATGTTGGGTGGTTGTCCAAAAGAGCGTGCAGA</u>

<u>GATTTCAATGCTTGAAGGAGCGGTTTTGGATATTAGATACGGTGTTTCGAGAATTGCATATAGTAAAG</u>

-continued

ACTTTGAAACTCTCAAAGTTGATTTTCTTAGCAAGCTACCTGAAATGCTGAAAATGTTCGAAGATCGT

TTATGTCATAAAACATATTTAAATGGTGATCATGTAACCCATCCTGACTTCATGTTGTATGACGCTCT

TGATGTTGTTTTATACATGGACCCAATGTGCCTGGATGCGTTCCCAAAATTAGTTTGTTTTAAAAAAC

GTATTGAAGCTATCCCACAAATTGATAAGTACTTGAAATCCAGCAAGTATATAGCATGGCCTTTGCAG

GGCTGGCAAGCCACGTTTGGTGGTGGCGACCATCCTCCAAAATCGGATCTGGAAGTTCTGTTCCAGGG

GCCCCTGGGATCCGAAAATTTATATTTTCAAATGAGAACACAGTCTACAGCTTCATTGTTCGCAACAA

TCACTGGCGCCAGCAAAACGGAATGGTCTTTCTCAGATATCGAATTGACTTACCGTCCAAACACGCTT

AAAAGCCTTGGCGTTATGGAGTTTACATTGCCAAGCGGATTTACTGCAAACACGAAAGACACATTGAA

CGGAAATGCCTTGCGTACAACACAGATCCTCAATAACGGGAAAACAGTAAGAGTTCCTTTGGCACTTG

ATTTGTTAGGAGCTGGCGAATTCAAATTAAAACTGAATAACAAAACACTTCCTGCCGCTGGTACATAT

ACTTTCCGTGCGGAGAATAAATCATTAAGCATCGGAAATAAATTTTACGCAGAAGCCAGCATTGACGT

GGCTAAGCGCAGCACTCCTCCGACTCAGCCTTGCGGTTGCAACTAATAA

The nucleotides encoding the L to K substitution are in underlined

```
Protein sequence-BslA-L77K (42-181 truncated form) linked
to GST (SEQ ID NO: 9):
MSPILGYWKIKGLVQPTRLLLEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFETLKVDFLSKLPEMLFMFEDR

LCHKTYLNGDHVTHPDFMLYDALDVVLYMDPMCLDAFPKLVCFKKRIEAIPQIDKYLKSSKYIAWPLQ

GWQATFGGGDHPPKSDLEVLFQGPLGSENLYFQMRTQSTASLFATITGASKTEWSFSDIELTYRPNTLK

SLGVMEFTLPSGFTANTKDTLNGNALRTTQILNNGKTVRVPLALDLLGAGEFKLKLNNKTLPAAGTY

TFRAENKSLSIGNKFYAEASIDVAKRSTPPTQPCGCN
```

The L to K substitution is in underlined.

Primers

```
L77K
                                  (SEQ ID NO: 10)
CCGTCCAAACACGCTTAAAAGCCTTGGCGTTATGG
```

```
L77K
                                  (SEQ ID NO: 11)
CCATAACGCCAAGGCTTTTAAGCGTGTTTGGACGG
```

```
C178A NSW1906
                                  (SEQ ID NO: 12)
TCCTCCGACTCAGCCTgcaGGTTGCAACTAATAAC
```

The region for mutation of the DNA is in lower case.

```
C178A NSW1907
                                  (SEQ ID NO: 13)
GTTATTAGTTGCAACCtgcAGGCTGAGTCGGAGGA
```

The region for mutation of the DNA is in lower case.

```
C180A NSW1908
                                  (SEQ ID NO: 14)
GACTCAGCCTTGCGGTgcaAACTAATAACTCGAGC
```

The region for mutation of the DNA is in lower case.

```
C180A NSW1909
                                  (SEQ ID NO: 15)
GCTCGAGTTATTAGTTtgcACCGCAAGGCTGAGTC
```

The region for mutation of the DNA is in lower case.

```
C178A NSW1910
                                  (SEQ ID NO: 16)
TCCGACTCAG CCTgcaGGTg caAACTAAT AACTCG
```

The region for mutation of the DNA is in lower case.

```
C178A NSW1911
                                  (SEQ ID NO: 17)
CGAGTTATTAGTTtgcACCtgcAGGCTGAGTCGGA
```

The region for mutation of the DNA is in lower case.

```
Full length BsIA mutant
                                  (SEQ ID NO: 18)
MKRKLLSSLA ISALSLGLLV SAPTASFAAE STSTKAHTES

TMRTQSTASL FATITGASKT EWSFSDIELT YRPNTLLSLG

VMEFTLPSGF TANTKDTLNG NALRTTQILN NGKTVRVPLA
```

```
-continued
LDLLGAGEFK LKLNNKTLPA AGTYTFRAEN KSLSIGNKFY

AEASIDVAKR STPPTQPXGX N
```
X is a non-sulfur containing residue.

```
BsIA mutant truncated
                                     (SEQ ID NO: 19)
MRTQSTASL FATITGASKT EWSFSDIELT YRPNTLLSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPXGX N
```
X is a non-sulfur containing residue.

```
Full length AxA-BsIA mutant
                                     (SEQ ID NO: 20)
MKRKLLSSLA ISALSLGLLV SAPTASFAAE STSTKAHTES

TMRTQSTASL FATITGASKT EWSFSDIELT YRPNTLLSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPAGA N
```
C to A substitution is underlined.

```
AxA-BsIA truncated
                                     (SEQ ID NO: 21)
MRTQSTASL FATITGASKT EWSFSDIELT YRPNTLLSLG

VMEFTLPSGF TANTKDTLNG NALRTTQILN NGKTVRVPLA

LDLLGAGEFK LKLNNKTLPA AGTYTFRAEN KSLSIGNKFY

AEASIDVAKR STPPTQPAGA N
```
C to A substitution is underlined.

```
Truncated (amino acids 40-179) B. licheniformis
BsIA
                                     (SEQ ID NO: 22)
YRPAASASLY SVITGASKQE WSFSDIELTY RPNSILALGT

VEFTLPSGFS ATTKDTVNGR ALTTGQILNN GKTVRLPLTI

DLLGIAEFKL VLANKTLPAA GKYTFRAENR VLGLGSTFYA

ESSIEVQKRA TPPTQPCNCK

Truncated (amino acids 42-181) B. amyloliqu-
faciens BsIA
                                     (SEQ ID NO: 23)
MSTKATATLF AKYTGASQQE WSFSDIELTY RPNTILSLGV

MEFTLPSGFA ATTKDTVNGH ALRERQILNN GKTVRLPLNI

DLLGAAEFKL SLNNKTLPAA GTYKFRAENK SLSIGSKFYA

EDTIVVQKRS TPPTQPCNCK

Truncated (amino acids 37-177) B. pumilus BsIA
                                     (SEQ ID NO: 24)
STNARPAELY AKITGTSKQE WSFSDIELTY RPNSVLSLGA

IEFTLPAGFQ ATTKDIFNGK ALKDSYILNS GKTVRIPARL

DLLGISQFKL QLSHKVLPAA GTYTFRAENR ALSIGSKFYA

EDTLDIQTRP VVVTPPDPCG C

Full length B. licheniformis BsIA
                                     (SEQ ID NO: 25)
MKMKHKFFST VMASLFGLVL LLSLPTASFA AESSSTVHEP

EMSTKATATL FAKYTGASQQ EWSFSDIELT YRPNTILSLG

VMEFTLPSGF TATTKDTVNG HALRERQILN NGKTVRLPLN

IDLIGAAEFK LSLNNKTLPA AGTYKFRAEN KSLSIGSKFY

AEDTIVVQKR STPPTQPCNC K

Full length B. amyloliquefaciens BsIA
                                     (SEQ ID NO: 26)
MLKRMYRSKL SILAVSLVMM VSIFLPSFQA SAQTTKTESV

YRPAANASLY ATITGASKQE WSFSDIELTY RPNSILALGT

VEFTLPSGFS ATTKDTVNGR ALTTGQILNN GKTVRLPLTI

DLLGIAEFKL VLANKTLPAA GKYTFRAENR VLGLGSTFYA

ESSIEVQKRA TPPTQPCNCK

Full length B. pumilus BsIA
                                     (SEQ ID NO: 27)
MKKTWTMIMM GMLTLVMALS VPIAASAEGA TQEGKASTNA

RPAELYAKIT GTSKQEWSFS DIELTYRPNS VLSLGAIEFT

LPAGFQATTK DIFNGKALKD SYILNSGKTV RIPARLDLLG

ISQFKLQLSH KVLPAAGTYT FRAENRALSI GSKFYAEDTL

DIQTRPVVVT PPDPCGC

Full length B. subtilis YweA
                                     (SEQ ID NO: 28)
MLKRTSFVSS LFISSAVLLS ILLPSGQAHA QSASIEAKTV

NSTKEWTISD IEVTYKPNAV LSLGAVEFQF PDGFHATTRD

SVNGRTLKET QILNDGKTVR LPLTLDLLGA SEFDLVMVRK

TLPRAGTYTI KGDVVNGLGI GSFYAETQLV IDPR

Truncated B. subtilis YweA
                                     (SEQ ID NO: 29)
QSASIEAKTV NSTKEWTISD IEVTYKPNAV LSLGAVEFQF

PDGFHATTRD SVNGRTLKET QILNDGKTVR LPLTLDLLGA

SEFDLVMVRK TLPRAGTYTI KGDVVNGLGI GSFYAETQLV IDPR
```

REFERENCES

1. Hobley L et al. (2013) BslA is a self-assembling bacterial hydrophobin that coats the *Bacillus subtilis* biofilm. *Proceedings of the National Academy of Sciences of the United States of America* 110:13600-13605.
2. Smith & Waterman, Adv. Appl. Math. 2:482, 1981.
3. Needleman & Wunsch, J. Mol. Biol. 48:443, 1970.
4. Pearson & Lipman, Proc. Nat. Acad. Sci. USA 85:2444, 1988.
5. Higgins & Sharp, Gene, 73:23744, 1988.
6. Higgins & Sharp, CABIOS 5:151-3, 1989.
7. Corpet et al., Nuc. Acids Res. 16:10881-90, 1988.
8. Huang et al., Computer Appls. in the Biosciences 8, 155-65, 1992.
9. Pearson et al., Meth Mol. Bio. 24:307-31, 1994.
10. Altschul et al., J. Mol. Biol. 215:403-10, 1990.
11. Hancock and Armstrong, Comput. Appl. Biosci. 10:67-70, 1994.
12. Current Protocols in Molecular Biology (Ausubel, 2000, Wiley and son Inc, Library of Congress, USA);

13. Molecular Cloning: A Laboratory Manual, Third Edition, (Sambrook et al, 2001, Cold Spring Harbor, N.Y.: Cold Spring Harbor Laboratory Press);
14. Oligonucleotide Synthesis (M. J. Gait ed., 1984);
15. U.S. Pat. No. 4,683,195;
16. Nucleic Acid Hybridization (Harries and Higgins eds. 1984);
17. Transcription and Translation (Hames and Higgins eds. 1984);
18. Culture of Animal Cells (Freshney, Alan R. Liss, Inc., 1987);
19. Immobilized Cells and Enzymes (IRL Press, 1986);
20. Perbal, A Practical Guide to Molecular Cloning (1984);
21. the series, Methods in Enzymology (Abelson and Simon, eds. -in-chief, Academic Press, Inc., New York), specifically, Vols. 154 and 155 (Wu et al. eds.) and Vol. 185, "Gene Expression Technology" (Goeddel, ed.);
22. Gene Transfer Vectors For Mammalian Cells (Miller and Calos eds., 1987, Cold Spring Harbor Laboratory);
23. Immunochemical Methods in Cell and Molecular Biology (Mayer and Walker, eds., Academic Press, London, 1987);
24. Handbook of Experimental Immunology, Vols. I-IV (Weir and Blackwell, eds., 1986);
25. Manipulating the Mouse Embryo, (Cold Spring Harbor Laboratory Press, Cold Spring Harbor, N.Y., 1986).
26. Humphrey W, Dalke A, Schulten K (1996) VMD: visual molecular dynamics. *Journal of Molecular Graphics* 14:33-38.
27. Andreas J M, Hauser E A, Tucker W B (1938) Boundary Tension by Pendant Drops. *Journal of Physical Chemistry* 42:1001-1019.
28. Stauffer C E (1965) The Measurement of Surface Tension by the Pendant Drop Technique. *Journal of Physical Chem* 69:1933-1938.
29. Rosen M J (2004) *Surfactants and interfacial phenomena* (J. Wiley & Sons, Hoboken, N.J.). 3rd Ed.
30. Alexandrov N A et al. (2012) Interfacial layers from the protein HFBII hydrophobin: dynamic surface tension, dilatational elasticity and relaxation times. *Journal of Multiphase system and Interface Science* 376:296-306.
31. Tripp B C, Magda J J, Andrade J D (1995) Adsorption of globular protein at air/water interface as measured by dynamic surface tension: Concentration dependence, mass-transfer considerations, and adsorption kinetics. *Journal of Multiphase system and Interface Science* 173: 16-27.
32. Beverung C J, Radke C J, Blanch H W (1999) Protein adsorption at the oil/water interface: characterization of adsorption kinetics by dynamic interfacial tension measurements. *Biophysical Chemistry* 81:59-80.
33. Ward A F H, Tordai L (1946) Time-Dependence of Boundary Tensions of Solutions I. The Role of Diffusion in Time-Effects. *The Journal of Chemical Physics* 14:453.
34. Husband F A, Garrood M J, Mackie A R, Burnett G R, Wilde P J (2001) Adsorbed Protein Secondary and Tertiary Structures by Circular Dichroism and Infrared Spectroscopy with Refractive Index Matched Emulsions.pdf. 859-866.
35. Towell III J F, Manning M C (1994) in *Analytical Applications of Circular Dichroism*, eds Purdie N, Brittain H G (Elsevier, New York), pp 175-205.
36. Jarzynski C (1997) Nonequilibrium Equality for Free Energy Differences. *Physical Review Letters* 78:2690-2693.

---

The invention in which an exclusive property or privilege is claimed is defined as follows:

1. A synthetic multiphase product comprising from 0.005 to 0.2 wt % of an isolated biofilm surface layer protein A (BslA), wherein the BslA has the amino acid sequence set forth in SEQ ID NO: 28 or an amino acid sequence that is at least 80% identical to SEQ ID NO: 28, and wherein the synthetic multiphase product further comprises at least one co-surfactant.

2. The synthetic multiphase product of claim 1, wherein the synthetic multiphase product is a multiphase food product.

3. The synthetic multiphase product of claim 1, wherein the synthetic multiphase product is a personal care product.

4. The synthetic multiphase product of claim 1 comprising at least three or more intimately mixed phases of matter.

5. The synthetic multiphase product of claim 4, wherein the synthetic multiphase product comprises a pharmaceutical active agent.

6. A frozen synthetic multiphase product comprising from 0.005 to 0.2 wt % of an isolated BslA, wherein the BslA has the amino acid sequence set forth in SEQ ID NO: 28 or a variant thereof that is at least 80% identical to SEQ ID NO: 28, and wherein the synthetic multiphase product further comprises at least one co-surfactant.

7. The frozen synthetic multiphase product of claim 6, wherein the at least one co-surfactant is a protein surfactant.

8. The frozen synthetic multiphase product of claim 6 comprising one or more additional components, wherein the one or more additional components comprises one or more of milk proteins, sugars, carbohydrates, egg proteins and fats.

* * * * *